United States Patent
Edwards et al.

(10) Patent No.: US 10,000,561 B2
(45) Date of Patent: Jun. 19, 2018

(54) THYMIC STROMAL LYMPHOPOIETIN (TSLP)-BINDING MOLECULES AND METHODS OF USING THE MOLECULES

(71) Applicant: NOVARTIS AG, Basel OT (CH)

(72) Inventors: Matthew John Edwards, Horsham (GB); Jean-Michel Rene Rondeau, Rixheim (FR); Danforth Miller, San Carlos, CA (US); Daniel Huang, Palo Alto, CA (US); Hans-Peter Knopf, Schallstadt (DE); Gino Anselmus Van Heeke, Upper Beeding (GB); Rene Hemmig, Basel (CH); Kapil Gupta, Concord, MA (US); Nicole Haubst, Munich (DE); Barbara Andlauer, Planegg (DE)

(73) Assignee: NOVARTIS AG, Basel (CH)

(*) Notice: Subject to any disclaimer, the term of this patent is extended or adjusted under 35 U.S.C. 154(b) by 0 days. days.

(21) Appl. No.: 15/258,683

(22) Filed: Sep. 7, 2016

(65) Prior Publication Data

US 2017/0066823 A1 Mar. 9, 2017

Related U.S. Application Data

(60) Provisional application No. 62/216,050, filed on Sep. 9, 2015, provisional application No. 62/342,511, filed on May 27, 2016.

(51) Int. Cl.
| | |
|---|---|
| C07K 16/24 | (2006.01) |
| A61K 39/395 | (2006.01) |
| A61K 9/00 | (2006.01) |
| A61K 45/06 | (2006.01) |
| A61K 9/16 | (2006.01) |
| A61K 39/00 | (2006.01) |

(52) U.S. Cl.
CPC ............ *C07K 16/24* (2013.01); *A61K 9/0075* (2013.01); *A61K 9/1617* (2013.01); *A61K 9/1623* (2013.01); *A61K 39/3955* (2013.01); *A61K 45/06* (2013.01); *C07K 16/244* (2013.01); *A61K 9/0043* (2013.01); *A61K 2039/505* (2013.01); *A61K 2039/544* (2013.01); *A61K 2039/545* (2013.01); *C07K 2317/21* (2013.01); *C07K 2317/33* (2013.01); *C07K 2317/34* (2013.01); *C07K 2317/55* (2013.01); *C07K 2317/76* (2013.01); *C07K 2317/92* (2013.01); *C07K 2317/94* (2013.01)

(58) Field of Classification Search
CPC .................................................... C07K 16/24
See application file for complete search history.

(56) References Cited

U.S. PATENT DOCUMENTS

| | | | |
|---|---|---|---|
| 7,304,144 B2 | 12/2007 | Sims et al. | |
| 9,284,372 B2 | 3/2016 | Comeau et al. | |
| 2005/0014199 A1 | 1/2005 | Reche-Gallardo | |
| 2006/0039910 A1 | 2/2006 | Comeau et al. | |
| 2006/0171943 A1 | 8/2006 | Comeau et al. | |
| 2007/0020262 A1 | 1/2007 | De Waal Malefyt et al. | |
| 2007/0048781 A1 | 3/2007 | Bazan et al. | |
| 2007/0071675 A1 | 3/2007 | Wu et al. | |
| 2007/0218523 A1 | 9/2007 | Lyman et al. | |
| 2008/0152620 A1 | 6/2008 | Mattson et al. | |
| 2009/0238823 A1* | 9/2009 | Comeau ............... | C07K 16/244 424/133.1 |
| 2012/0190829 A1 | 7/2012 | Mehlin et al. | |
| 2013/0096028 A1 | 4/2013 | Hirasawa et al. | |

FOREIGN PATENT DOCUMENTS

| | | |
|---|---|---|
| EP | 1797902 A2 | 6/2007 |
| EP | 2213682 A1 | 8/2010 |
| WO | 0029581 A1 | 5/2000 |
| WO | 2006023226 A2 | 3/2006 |
| WO | 2007024715 A2 | 3/2007 |
| WO | 2007096149 A1 | 8/2007 |
| WO | 2007112146 A2 | 10/2007 |
| WO | 2008076321 A1 | 6/2008 |
| WO | 2008155365 A1 | 12/2008 |
| WO | 2009035577 A1 | 3/2009 |
| WO | 2009100324 A1 | 8/2009 |
| WO | 2009124090 A1 | 10/2009 |
| WO | 2010111490 A2 | 9/2010 |
| WO | 2011056772 A1 | 5/2011 |
| WO | 2011070970 A1 | 6/2011 |
| WO | 2012007495 A1 | 1/2012 |
| WO | 2012074842 A2 | 6/2012 |
| WO | 2013063062 A2 | 5/2013 |
| WO | 2013067051 A1 | 5/2013 |
| WO | 2014031718 A1 | 2/2014 |
| WO | 2014162007 A2 | 10/2014 |
| WO | 2015009996 A1 | 1/2015 |

OTHER PUBLICATIONS

Reche et al., "Human thymic stromal lymphopoietin preferentially stimulates myeloid cells," J Immunol. Jul. 1, 2001;167 (1)336-43.
Gauvreau et al., "Effects of an anti-TSLP antibody on allergen-induced asthmatic responses," N Engl J Met May 29, 2014;370(22):2102-10.
Edwards, "Therapy directed against thymic stromal lymphopoietin," Drug News Perspect. Jul.-Aug. 2008;21(6):312-6.
International Search Report and Written Opinion for International Application No. PCT/IB2016/055336, dated Dec. 12, 2016 (15 pages).

* cited by examiner

*Primary Examiner* — Jessica H Roark
(74) *Attorney, Agent, or Firm* — Adam Poulin-Kerstien

(57) ABSTRACT

The invention provides molecules, e.g., antibodies or antibody fragments, that specifically bind thymic stromal lymphopoietin (TSLP), compositions comprising these molecules, and methods of using and producing these molecules.

31 Claims, 11 Drawing Sheets

Fig. 1A

EVQLVESGGGLVKPGGSLRLSCAASGFTFSDYWMHWVRQAPGKGLEWVGRIKSKTDAGTTDYAAPVK
GRFTISRDDSKNTLYLQMNSLKTEDTAVYYCARRIYYYAFDSWGQGTLVTVSSASTKGPSVFPLAPS
SKSTSGGTAALGCLVKDYFPEPVTVSWNSGALTSGVHTFPAVLQSSGLYSLSSVVTVPSSSLGTQTY
ICNVNHKPSNTKVDKRVEPKSC (SEQ ID NO: 22)

Fig. 1B

SYELTQPLSVSVALGQTARITCSGDNIGSKYVHWYQQKPGQAPVLVIYKDNERPSGIPERFSGSNSGNTATLTIS
RAQAGDEADYYCQAADWVDFYVFGGGTKLTVLGQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS (SEQ ID NO: 25)

Fig. 2

```
                                                    11            21      28
                                                  MGSSHHHHHH LEVLFQSP
 29   33          41              51              61            71           81
 YD   FTNCDFEKIK  AAYLSTISKD  LITYMSGTKS  TEFNNTVSCS  NRPHCLTEIQ  SLTFNPTAGC 91            101           111         121          131         141
 ASLAKEMFAM  KTKAALAIWC  PGYSETQINA  TQAMKKRRKR  KVTTNKCLEQ  VSQLQGLWRR 151        158
 FNRPLLKQQ (SEQ ID NO: 38)
```

Fig. 11A
Fig. 11B
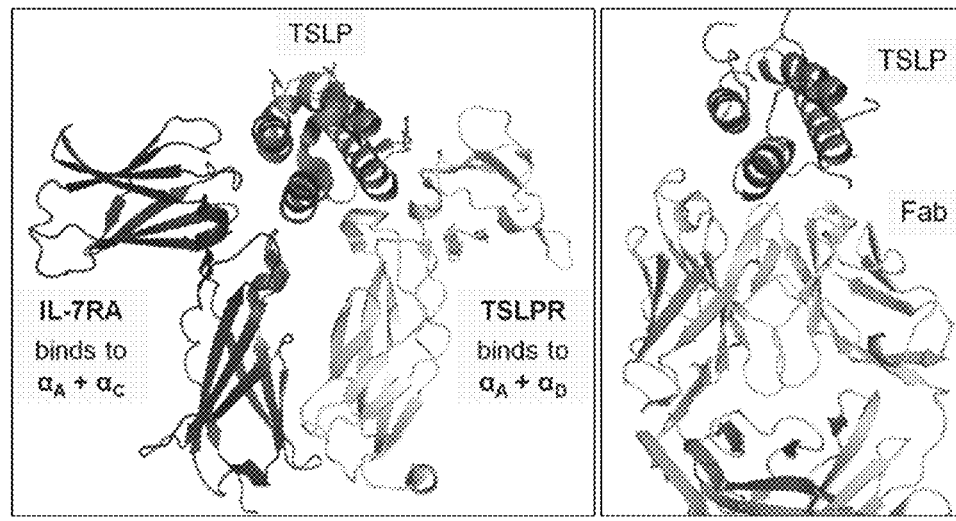
Fig. 11C
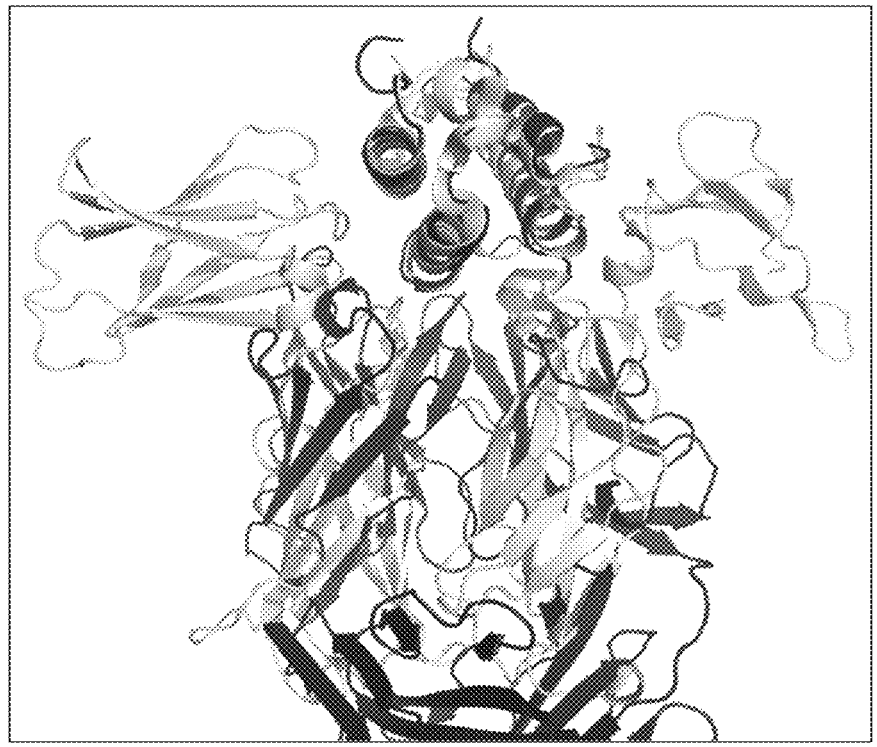

THYMIC STROMAL LYMPHOPOIETIN (TSLP)-BINDING MOLECULES AND METHODS OF USING THE MOLECULES

This application claims priority to U.S. Provisional Application No. 62/216,050, filed Sep. 9, 2015, U.S. Provisional Application No. 62/215,904, filed Sep. 9, 2015, and U.S. Provisional Application No. 62/342,511, filed May 27, 2016, all of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Aug. 23, 2016, is named PAT057035-WO-PCT_SL.txt and is 46,696 bytes in size.

TECHNICAL BACKGROUND

The present invention provides molecules, e.g., antibodies or antibody fragments, that specifically bind thymic stromal lymphopoietin (TSLP), compositions comprising these molecules, and methods of using and producing these molecules.

BACKGROUND

Thymic stromal lymphopoietin (TSLP) is a cytokine that signals through a heterodimeric receptor consisting of the IL-7Rα subunit and TSLP-R, a unique component with homology to the common γ-receptor-like chain (Pandey et al., Nat. Immunol. 2000, 1(1):59-64). TSLP is expressed by epithelial cells in the thymus, lung, skin, intestine, and tonsils, as well as airway smooth muscle cells, lung fibroblasts, and stromal cells (Edwards, 2008, Drug news & perspectives 21, 312-316; He and Geha, 2010, Annals of the New York Academy of Sciences 1183, 13-24; Reche et al., 2001, Journal of immunology 167, 336-343). These cells produce TSLP in response to proinflammatory stimuli, and TSLP drives allergic inflammatory responses through its activity on a number of innate immune cells, including dendritic cells (Soumelis et al., 2002, Nature immunology 3, 673-680), monocytes (Reche et al., 2001, Journal of immunology 167, 336-343), and mast cells (Allakhverdi et al., 2007, The Journal of Experimental Medicine 204, 253-258). The cell populations with the highest known expression of both TSLP-R and IL-7Rα are myeloid dendritic cells (Reche et al., 2001, Journal of immunology 167, 336-343).

TSLP can promote proliferation of naive T cells and drive their differentiation into Th2 cells expressing high levels of IL-4, IL-5, and IL-13 (Omori and Ziegler, 2007, Journal of immunology 178, 1396-1404). High level of TSLP expression has been found in asthmatic lung epithelial cells and chronic atopic dermatitis lesions, suggesting a role for TSLP in allergic inflammation (Ziegler and Artis, 2010, Nature immunology 11, 289-293). More recent evidence implicates TSLP in the differentiation of Th17 cells and Th17-driven inflammatory processes (Hartgring et al., 2011, Arthritis and rheumatism 63, 1878-1887; Tanaka et al., 2009, Clinical and experimental allergy: Journal of the British Society for Allergy and Clinical Immunology 39, 89-100; Wu et al., 2014, Journal of molecular and cellular cardiology 76, 33-45). Chronic allergic (atopic) asthma is often characterized by Th2-type inflammation, while non-allergic asthmatic inflammation is predominately neutrophilic with a mixed Th1 and Th17 cytokine milieu. The consequences of chronic inflammation in asthma include bronchial hyper-reactivity (BHR), mucus overproduction, airway wall remodeling and airway narrowing (Lambrecht and Hammad, 2014, Nature immunology 16, 45-56). TSLP was shown to be involved in the initiation and maintenance/enhancement of the allergic asthmatic response (Wang et al., 2006, Immunity 24, 827-838). More recently, TSLP signaling was also found to be required for the recall response of memory T-cells to local antigen challenge (Wang et al., 2015, The Journal of allergy and clinical immunology 135, 781-791 e783).

SUMMARY OF THE INVENTION

In one aspect, provided herein are molecules, e.g., monoclonal antibodies or antibody fragments thereof such as Fab, Fab', F(ab')2, scFv, minibody, or diabody, that specifically bind human thymic stromal lymphopoietin (TSLP). In some embodiments, the TSLP-binding molecules can comprise: a heavy chain complementarity determining region 1 (HCDR1) comprising the amino acid sequence of SEQ ID NO: 4; a heavy chain complementarity determining region 2 (HCDR2) comprising the amino acid sequence of SEQ ID NO: 2; a heavy chain complementarity determining region 3 (HCDR3) comprising the amino acid sequence of SEQ ID NO: 3; a light chain complementarity determining region 1 (LCDR1) comprising the amino acid sequence of SEQ ID NO: 11; a light chain complementarity determining region 2 (LCDR2) comprising the amino acid sequence of SEQ ID NO: 12; and a light chain complementarity determining region 3 (LCDR3) comprising the amino acid sequence of SEQ ID NO: 13. In some embodiments, the TSLP-binding molecules can comprise: a molecule that comprises: a HCDR1 comprising the amino acid sequence of SEQ ID NO: 5; a HCDR2 comprising the amino acid sequence of SEQ ID NO: 6; a HCDR3 comprising the amino acid sequence of SEQ ID NO: 3; a LCDR1 comprising the amino acid sequence of SEQ ID NO: 14; a LCDR2 comprising the amino acid sequence of SEQ ID NO: 15; and a LCDR3 comprising the amino acid sequence of SEQ ID NO: 16.

In some specific embodiments, the molecule comprises an antibody fragment that binds human TSLP and comprises a HCDR1 comprising the amino acid sequence of SEQ ID NO: 4; a HCDR2 comprising the amino acid sequence of SEQ ID NO: 2; a HCDR3 comprising the amino acid sequence of SEQ ID NO: 3; a LCDR1 comprising the amino acid sequence of SEQ ID NO: 11; a LCDR2 comprising the amino acid sequence of SEQ ID NO: 12; and a LCDR3 comprising the amino acid sequence of SEQ ID NO: 13. In other specific embodiments, the molecule comprises an antibody fragment that binds human TSLP and comprises a HCDR1 comprising the amino acid sequence of SEQ ID NO: 5; a HCDR2 comprising the amino acid sequence of SEQ ID NO: 6; a HCDR3 comprising the amino acid sequence of SEQ ID NO: 3; a LCDR1 comprising the amino acid sequence of SEQ ID NO: 14; a LCDR2 comprising the amino acid sequence of SEQ ID NO: 15; and a LCDR3 comprising the amino acid sequence of SEQ ID NO: 16.

In some embodiments, the TSLP-binding molecules can comprise: a heavy chain variable region comprising the amino acid sequence of SEQ ID NO: 7, and a light chain variable region comprising the amino acid sequence of SEQ ID NO: 17.

In some embodiments, the TSLP-binding molecules can comprise: a heavy chain comprising the amino acid sequence of SEQ ID NO: 22, and a light chain comprising the amino acid sequence of SEQ ID NO: 25. In some embodiments, the TSLP-binding molecules can comprise: a heavy chain comprising the amino acid sequence of SEQ ID NO: 9, and a light chain comprising the amino acid sequence of SEQ ID NO: 19.

In some embodiments, the TSLP-binding molecules can comprise a paratope comprising at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or all of the following residues: Thr28, Asp31, Tyr32, Trp33, Asp56, Glu101, Ile102, Tyr103, Tyr104, Tyr105 of a heavy chain sequence of SEQ ID NO:22 or Gly28, Ser29, Lys30, Tyr31, Tyr48, Asp50, Asn51, Glu52, Asn65, and Trp92 of a light chain sequence of SEQ ID NO:25.

In some embodiments, provided herein are molecules that specifically bind an epitope in human TSLP, wherein the epitope comprises at least one, at least two, at least three, at least four, at least five, at least six, at least seven, at least eight, at least nine, at least 10, at least 11, at least 12, at least 13, at least 14, at least 15, or all of the following residues: Lys38, Ala41, Leu44, Ser45, Thr46, Ser48, Lys49, Ile52, Thr53, Ser56, Gly57, Thr58, Lys59, Lys101, Gln145, and Arg149 of SEQ ID NO: 38. In some embodiments, such molecules bind an epitope comprising at least one of the following sets of residues of SEQ ID NO: 38: (a) Lys49 and Ile52, (b) Gly57 and Lys59, (c) Lys101, or (d) Gln145 and Arg149.

In some embodiments, the TSLP-binding molecules are human immunoglobulins that specifically bind human TSLP. In some embodiments, the TSLP-binding molecules are monoclonal antibodies or a fragment of antibody selected from a Fab, Fab', F(ab')2, scFv, minibody, or diabody. In some embodiments, the TSLP-binding molecules are Fabs, e.g., human or humanized Fabs, that specifically bind human TSLP.

In some embodiments, the molecules described herein bind human TSLP with a dissociation constant ($K_D$) of less than 100 pM. In some embodiments, the molecules described herein bind human TSLP with a dissociation constant ($K_D$) of less than 10 pM.

In another aspect, provided herein are pharmaceutical compositions comprising at least one TSLP-binding molecule described herein and at least one pharmaceutically acceptable excipient. In some embodiments, the excipient: TSLP-binding molecule mass ratio is greater than 0.5. In some embodiments, the TSLP-binding molecule is about 5% to about 95%, or about 10% to about 90%, or about 15% to about 85%, or about 20% to about 80%, or about 25% to about 75%, or about 30% to about 70%, or about 40% to about 60%, or about 40-50% (w/w) of the pharmaceutical composition. In some embodiments, the pharmaceutical compositions comprise a shell-forming agent, such as trileucine or leucine. In some embodiments, the trileucine or leucine is about 10-75% (w/w) of the composition. In some embodiments, the trileucine is about 10-30% (w/w) of the composition. In other embodiment, the leucine is about 50-75% (w/w) of the composition. In some embodiments, the pharmaceutical compositions comprise at least one glass-forming excipient, wherein the glass-forming excipient is selected from histidine, trehalose, mannitol, sucrose, or sodium citrate. In some embodiments, at least one glass-forming excipient is trehalose or a mixture of trehalose and mannitol. In some embodiments, the glass-forming excipient is about 15-35% (w/w) of the composition. In some embodiments, the pharmaceutical compositions comprise a buffer, such as a histidine, glycine, acetate, or phosphate buffer. In some embodiments, the buffer is about 5-13% of the composition.

In some embodiments, the pharmaceutical compositions provided herein are formulated as a dry powder formulation, e.g., a dry powder formulation suitable for inhalation.

In some embodiments, the pharmaceutical compositions provided herein comprise spray-dried particles comprising a shell and a core, wherein the shell comprises trileucine or leucine, and the core comprises: (i) the TSLP-binding molecule, trehalose, mannitol and a buffer; or (ii) the TSLP-binding molecule, trehalose, buffer, and HCl. The buffer can be a histidine, glycine, acetate, or phosphate buffer.

In some embodiments, the pharmaceutical compositions provided herein comprise spray-dried particles comprising: (i) a shell comprising trileucine or leucine; and (ii) a core comprising trehalose, mannitol, histidine, and a TSLP-binding molecule, or a core comprising trehalose, histidine, HCl, and a TSLP-binding molecule, wherein the TSLP-binding molecule is an antibody Fab fragment comprising: either (a) a HCDR1 comprising the amino acid sequence of SEQ ID NO: 4; a HCDR2 comprising the amino acid sequence of SEQ ID NO: 2; a HCDR3 comprising the amino acid sequence of SEQ ID NO: 3; a LCDR1 comprising the amino acid sequence of SEQ ID NO: 11; a LCDR2 comprising the amino acid sequence of SEQ ID NO: 12; and a LCDR3 comprising the amino acid sequence of SEQ ID NO: 13; or (b) a HCDR1 comprising the amino acid sequence of SEQ ID NO: 5; a HCDR2 comprising the amino acid sequence of SEQ ID NO: 6; a HCDR3 comprising the amino acid sequence of SEQ ID NO: 3; a LCDR1 comprising the amino acid sequence of SEQ ID NO: 14; a LCDR2 comprising the amino acid sequence of SEQ ID NO: 15; and a LCDR3 comprising the amino acid sequence of SEQ ID NO: 16.

In some embodiments, the pharmaceutical compositions provided herein comprise:

(a) 40% (w/w) TSLP-binding molecule, 25% (w/w) trileucine, 30% (w/w) combined weight of trehalose and mannitol, and 5% (w/w) histidine;

b) 50% (w/w) TSLP-binding molecule, 15% (w/w) trileucine, 2.6% (w/w) HCl, 5.6% (w/w) histidine, and 26.8% (w/w) combined weight of trehalose and a base; or c) 50% (w/w) TSLP-binding molecule, 15% (w/w) trileucine, 19.4% (w/w) trehalose, 13.04% (w/w) histidine, and 2.56% (w/w) HCl.

Also provided herein are nucleic acids encoding any TSLP-binding molecule described herein, vectors comprising such nucleic acids, and host cells comprising the nucleic acid or the vector.

Also provided are methods of producing the TSLP-binding molecule described herein. Such methods can include (a) culturing a host cell expressing a nucleic acid encoding the molecule; and (b) collecting the molecule from the culture medium.

In another aspect, provided herein are kits comprising at least one TSLP-binding molecule or pharmaceutical composition described herein, and a device for delivering the molecule or pharmaceutical composition to a subject. In some embodiments, the device can deliver the molecule or pharmaceutical composition in an aerosolized form. In some embodiments, the device is a dry powder inhaler.

In another aspect, provided herein are methods of treating a TSLP-related condition in a subject in need thereof, e.g., a human patient, by administering to the subject a therapeutically effective amount of any TSLP-binding molecule or pharmaceutical composition described herein. Also provided are molecules or pharmaceutical compositions as described herein for use in treating a TSLP-related condition in a subject in need thereof. Use of the TSLP-binding molecules or pharmaceutical composition described herein to treat a TSLP-related condition in a subject in need thereof is also included. The present disclosure also includes use of the molecule described herein in the manufacture of a medicament for use in the treatment of a TSLP-related condition in a subject in need thereof.

The TSLP-related inflammatory condition can be any one of asthma, chronic obstructive pulmonary disease, allergic rhinitis, allergic rhinosinusitis, allergic conjunctivitis, eosinophilic esophagitis, or atopic dermatitis. In some embodiments, the TSLP-related inflammatory condition is asthma. In some embodiments, the TSLP-binding molecule is formulated as a dry powder formulation suitable for inhalation. In some embodiments, the TSLP-binding molecule is administered to the subject orally or intranasally, e.g., in an aerosolized form. In some embodiments, the TSLP-binding molecule is administered to the subject by a dry powder inhaler.

In some embodiments, the methods of treating a TSLP-related condition or uses of the TSLP-binding molecule further include administering a second agent to the subject in need of treatment. The second agent can be a corticosteroid, bronchodilator, antihistamine, antileukotriene, or PDE-4 inhibitor.

In another aspect, provided herein are methods for making a dry powder formulation comprising the TSLP-binding molecule described herein. Such methods can include one or more of the following steps: (a) providing an aqueous solution comprising a TSLP-binding molecule as described herein, trileucine or leucine, a glass forming excipient, and a buffer; (b) spray drying the aqueous solution of step (a) at a temperature between about 120° C. to about 200° C. (inlet) range and 55° C. to about 75° C. (outlet) to produce dry powder particles; and (c) collecting the dry power particles. In some embodiments, the buffer is selected from a histidine, glycine, acetate, or phosphate buffer. In some embodiments, the glass forming excipient is selected from histidine, histidine HCl, trehalose, mannitol, sucrose, or sodium citrate.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1A shows the amino acid sequence of anti-human TSLP Fab1 heavy chain (SEQ ID NO: 22) with the CDRs underlined (as defined by Kabat), and residues located at the antibody-antigen interface labeled with *. FIG. 1B shows the amino acid sequence of anti-human TSLP Fab1 light chain (SEQ ID NO: 25) with the CDRs underlined (as defined by Kabat), and residues located at the antibody-antigen interface labeled with *.

FIG. 2 shows the amino acid sequence of recombinant human TSLP used in crystallography studies (SEQ ID NO: 38), with the secondary structure elements shown below the amino acid sequence. The boxes represent α-helices $α_A$, $α_B$, $α_C$ and $α_D$, and the thick lines represent the loop regions. Mature human TSLP starts from Tyr29. The construct used here had an N-terminal hexahistidine tag (SEQ ID NO: 40) (residues 15-20) followed by a HRV-3C protease (PreScission) recognition site (residues 21-28) and residues 11-14 resulting from cloning. Asn64 and Asn119 are potential N-linked glycosylation sites; and residues 127-130 constitute the furin cleavage site.

FIGS. 11A-11C show the mode of action of anti-TSLP Fab1. FIG. 11A is a view of the mouse extracellular signalling complex, with IL-7Rα in black, and TSLPR in light-grey. FIG. 11B is a view of the human TSLP-Fab1 complex in the same orientation as FIG. 11A. FIG. 11C is the structural overlay of the two complexes, based on the cytokine Cα atoms. The mouse signaling complex is in light grey, the human TSLP-Fab1 complex is in black.

DETAILED DESCRIPTION

Definitions

Figure 3:
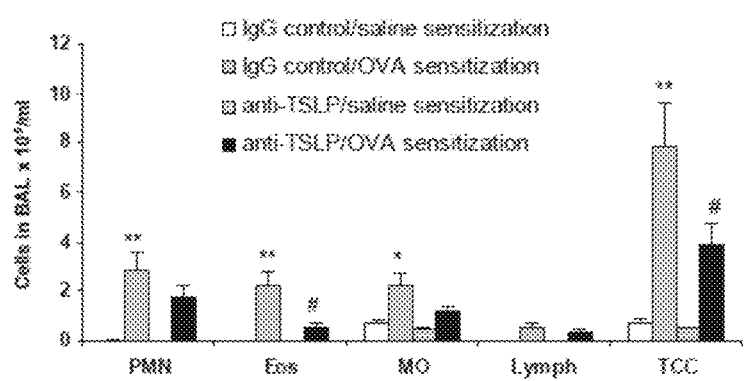
FIG. 3 is a bar graph showing the effect of TSLP neutralization on lung inflammation in ovalbumin-sensitized mice that were challenged with antigen. Mice sensitized with ovalbumin (OVA) or saline plus alum, received an intravenous administration of either antimurine TSLP or isotype control antibody at 1 h prior to sensitizations. All mice were OVA challenged on day 21 and culled at 24 h. Values represent mean±SEM (Standard Error Mean) total and differential cell counts within the BAL. Statistical analysis was performed using an unpaired student's T-test. Significant differences between isotype-treated saline-sensitized and OVA-sensitized mice at $p<0.05$ are denoted by (*) and $p<0.01$ denoted by (**). Differences between isotype and anti-TSLP antibody treated OVA-sensitized mice at the $p<0.05$ are denoted by (#). [PMN: Polymorphonuclear cells (neutrophils); Eos: Eosinophils; MO: monocytes; Lymph: Lymphocytes; TCC: Total Cell Count.]

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely examples and that equivalents of such are known in the art.

As used herein, "TSLP" (also known as "thymic stromal lymphopoietin") refers to a cytokine produced by non-hematopoietic cells in response to proinflammatory stimuli. The human TSLP gene is mapped to chromosomal location 5q22.1, and the genomic sequence of TSLP gene can be found in GenBank at NC_000005.10. Due to alternative splicing, two TSLP isoforms are present in the human. The protein and mRNA sequences for the two human TSLP isoforms are listed in Table 1.

TABLE 1

TSLP amino acid and mRNA sequences

| Species | Isoform | GeneBank Accession No. | Sequence |
|---|---|---|---|
| Homo sapiens | TSLP isoform 1 amino acid | NP_149024.1 | MFPFALLYVLSVSFRKIPILQLVGLVLTYDFTNC DFEKIKAAYLSTISKDLITYMSGTKSTEFNNTVS CSNRPHCLTEIQSLTFNPTAGCASLAKEMFAMK TKAALAIWCPGYSETQINATQAMKKRRKRKVT TNKCLEQVSQLQGLWRRFNRPLLKQQ (SEQ ID NO: 27) |
| Homo sapiens | TSLP isoform 1 mRNA | NM_033035.4 | GCAGCCAGAA AGCTCTGGAG CATCAGGGAG ACTCCAACTT AAGGCAACAG CATGGGTGAA TAAGGGCTTC CTGTGGACTG GCAATGAGAG GCAAAACCTG GTGCTTGAGC ACTGGCCCCT AAGGCAGGCC TTACAGATCT CTTACACTCG TGGTGGGAAG AGTTTAGTGT GAAACTGGGG TGGAATTGGG TGTCCACGTA TGTTCCCTTT TGCCTTACTA TATGTTCTGT CAGTTTCTTT CAGGAAAATC TTCATCTTAC AACTTGTAGG GCTGGTGTTA ACTTACGACT TCACTAACTG TGACTTTGAG AAGATTAAAG CAGCCTATCT CAGTACTATT TCTAAAGACC TGATTACATA TATGAGTGGG ACCAAAAGTA CCGAGTTCAA CAACACCGTC TCTTGTAGCA ATCGGCCACA TTGCCTTACT GAAATCCAGA GCCTAACCTT CAATCCCACC GCCGGCTGCG CGTCGCTCGC CAAAGAAATG TTCGCCATGA AAACTAAGGC TGCCTTAGCT ATCTGGTGCC CAGGCTATTC GGAAACTCAG ATAAATGCTA CTCAGGCAAT GAAGAAGAGG AGAAAAGGA AAGTCACAAC CAATAAATGT CTGGAACAAG TGTCACAATT ACAAGGATTG TGGCGTCGCT TCAATCGACC TTTACTGAAA CAACAGTAAA CCATCTTTAT TATGGTCATA TTTCACAGCA CCAAAATAAA TCATCTTTAT TAAGTAGATG AAACATTAAC TCTAACTGTG ACAAAGAAGA CCACAAATAG TTATCTTTTA ATTACAGAAG AGTTTCTTAA CTTACTTTTG TAAGTTTTTA TTGTGTAAGT TTATAATGCA GGGGAAGTAC TACTCCTCAA ATGTTGAGGG AAGCTTCCAT AACATTGATG ACTGGCTTCA TGGCAGTAAT TCTCGGCTGT AGTTGCATAA GCATTGCTCA AGAGGAAAAT CCAAAAGTGC AGCAGGAGAA CTCTTTTCCC TGAAAAAGGA AAAATATTGA ACTCAATGAT AGCACCTAAA CTTACATTTA AAAGACAGAC ATTCCTTCTA CATGTAATGA CACTTCTTGT GTTAAACTAA AAATTTACAA GAGAAGAAAG TGAAAGCAAA TGGGGTTTCA CAAATAGTTG TAAATATAGT GAAGCAATTT GAAATAATTT TCAAGCAAAG TATTGTGAAA GTATTCTAAG CCAAGTTTTA AATATTATCT AACAGACAAG AGTGGTATAT ACAAGTAGAT CCTGAGAAGT |

TABLE 1-continued

TSLP amino acid and mRNA sequences

| Species | Isoform | GeneBank Accession No. | Sequence |
|---|---|---|---|
| | | | ACCTTTGTTA CAGCTACTAT AAATATACAT<br>ATAAATTATA GAATCTACTT TAATTTATTT<br>TGTGAACACT TTTGAAAATG TACATGTTCC<br>TTTGTAATTG ACACTATATA TTTCTTAATA<br>AAATAATTCT CAAATTTGTT TCTTATGAAT<br>CATCTCTCAA ATCTAGTTAG ACAATTTGCA<br>CACATACTTT TCTAAGGGAC ATTATCTTCC<br>TTCAGGTTTT TACCTCCACT CATCCTTAGA<br>GCCCACTGAC TGCTCCCCTT TATACCTGTT<br>GGCCCTGCCT ATAGGAGAGA ATATTTGGAG<br>ATAGGCAGCT TCAGGATGCA TTGCAATCAT<br>CCTTTTCTTA AATTATGTCA CTAGTCTTTT<br>ATTTTTTCCC CTCTTGAACT TTCCTCACAC<br>CTGGAAGAAA CAAAGTAGGA AAAAGTGAAC<br>AGGGGATGTC AAATCGATTC TTGAATTCCC<br>GCTGCAAGCT AGAGCCGCAG GCACCCTCTC<br>ACTCAATTTC CACTCAGAAC CCTATAAACA<br>CCAGTGGGAA GGGCAACCCA CTGCACGTGG<br>GAATGCACTG ATTTTTCCTA GGAGTAGACA<br>TGTTCCTCTA ATTACTCCCT GAGGGTTAGT<br>TGGGGCTAAA CCATGACAGA AGTGGGGAAG<br>TTCAATGTCC TTAAATCCAT CTTACTTGCC<br>AACAGGTAAG AGGAAGCTTA CATTACATGT<br>CCAGTCCACA TTTAAAGAGC ACTTACTGTG<br>GAACAAGCCT TCAGCCAAAC AATGGGGATA<br>GAAAAGTAGG TAAGACTCAG CCTTTGTCCA<br>GAGAAGCTCA GGGTATAGCT GAATAGGCAG<br>TTTCTTTTGT CCTGAGGAAA ATCAGGACAT<br>GCCTGCTTTC TAAAAATCTT CCTCTGAAGA<br>CCTGACCCAA GCTCTTAAAT GCTATTGTAA<br>GAGAAATTTC TTTGTCTATT AACTCCATTT<br>TAGTAGGGAT TCACTGACTA GATTTTACTG<br>AACTATGAAA ATAAATACAC ATAATTTTTC<br>ACAAAATTTT GGGCCCAATT CCCCTAAAAG<br>AATTGAGGAT TAGGGAGAAA GGAGACAACT<br>CAAAGTCATC CCATTAAGTG CAGTTTCTTT<br>GAATCTTCTG CTTTATCTTT AAAAATTTGT<br>ATAATTTATA TATTTTATTC TATGTGTTCC<br>ATAGATATCT TAATGTAAAA TTAGTCATTT<br>AAATTACACT GTCAATTAAA AGTAATGGGC<br>AAGAGATTGC ATCATACTAA TTTAGTAAGA<br>ACGTTCCCAA ATGTTGTAAC AATGTGGATC<br>ATACATCTCT GGTTTTTTAA ATGTATTGAG<br>GCTTTCTTGG TGGACTAGTA TAGTATACGG<br>TCAGTTATGT CAATGTTTCA TGGTCAATAA<br>AAAGGAAGTT GCAAATTGT<br>(SEQ ID NO: 28) |
| Homo sapiens | TSLP isoform 2 amino acid | NP_612561.2 | MFAMKTKAALAIWCPGYSETQINATQAMKKRR<br>KRKVTTNKCLEQVSQLQGLWRRFNRPLLKQQ<br>(SEQ ID NO: 29) |
| Homo sapiens | TSLP isoform 2 mRNA | NM_138551.4 | ACCCTCGCCA CGCCCCTGCT CCCCCGCGGT<br>TGGTTCTTCC TTGCTCTACT CAACCCTGAC<br>CTCTTCTCTC TGACTCTCGA CTTGTGTTCC<br>CCGCTCCTCC CTGACCTTCC TCCCCTCCCC<br>TTTCACTCAA TTCTCACCAA CTCTTTCTCT<br>CTCTGGTGTT TTCTCCTTTT CTCGTAAACT<br>TTGCCGCCTA TGAGCAGCCA CATTGCCTTA<br>CTGAAATCCA GAGCCTAACC TTCAATCCCA<br>CCGCCGGCTG CGCGTCGCTC GCCAAAGAAA<br>TGTTCGCCAT GAAAACTAAG GCTGCCTTAG<br>CTATCTGGTG CCCAGGCTAT TCGGAAACTC<br>AGATAAATGC TACTCAGGCA ATGAAGAAGA<br>GGAGAAAAAG GAAAGTCACA ACCAATAAAT<br>GTCTGGAACA AGTGTCACAA TTACAAGGAT<br>TGTGGCGTCG CTTCAATCGA CCTTTACTGA<br>AACAACAGTA AACCATCTTT ATTATGGTCA<br>TATTTCACAG CACCAAAATA AATCATCTTT<br>ATTAAGTAGA TGAAACATTA ACTCTAACTG<br>TGACAAAGAA GACCACAAAT AGTTATCTTT<br>TAATTACAGA AGAGTTTCTT AACTTACTTT<br>TGTAAGTTTT TATTGTGTAA GTTTATAATG<br>CAGGGGAAGT ACTACTCCTC AAATGTTGAG<br>GGAAGCTTCC ATAACATTGA TGACTGGCTT |

TABLE 1-continued

TSLP amino acid and mRNA sequences

| Species | Isoform | GeneBank Accession No. | Sequence |
|---|---|---|---|
| | | | CATGGCAGTA ATTCTCGGCT GTAGTTGCAT<br>AAGCATTGCT CAAGAGGAAA ATCCAAAAGT<br>GCAGCAGGAG AACTCTTTTC CCTGAAAAAG<br>GAAAAATATT GAACTCAATG ATAGCACCTA<br>AACTTACATT TAAAAGACAG ACATTCCTTC<br>TACATGTAAT GACACTTCTT GTGTTAAACT<br>AAAAATTTAC AAGAGAAGAA AGTGAAAGCA<br>AATGGGGTTT CACAAATAGT TGTAAATATA<br>GTGAAGCAAT TTGAAATAAT TTTCAAGCAA<br>AGTATTGTGA AAGTATTCTA AGCCAAGTTT<br>TAAATATTAT CTAACAGACA AGAGTGGTAT<br>ATACAAGTAG ATCCTGAGAA GTACCTTTGT<br>TACAGCTACT ATAAATATAC ATATAAATTA<br>TAGAATCTAC TTTAATTTAT TTTGTGAACA<br>CTTTTGAAAA TGTACATGTT CCTTTGTAAT<br>TGACACTATA TATTTCTTAA TAAAATAATT<br>CTCAAATTTG TTTCTTATGA ATCATCTCTC<br>AAATCTAGTT AGACAATTTG CACACATACT<br>TTTCTAAGGG ACATTATCTT CCTTCAGGTT<br>TTTACCTCCA CTCATCCTTA GAGCCCACTG<br>ACTGCTCCCC TTTATACCTG TTGGCCCTGC<br>CTATAGGAGA GAATATTTGG AGATAGGCAG<br>CTTCAGGATG CATTGCAATC ATCCTTTTCT<br>TAAATTATGT CACTAGTCTT TTATTTTTTC<br>CCCTCTTGAA CTTTCCTCAC ACCTGGAAGA<br>AACAAAGTAG GAAAAAGTGA ACAGGGGATG<br>TCAAATCGAT TCTTGAATTC CCGCTGCAAG<br>CTAGAGCCGC AGGCACCCTC TCACTCAATT<br>TCCACTCAGA ACCCTATAAA CACCAGTGGG<br>AAGGGCAACC CACTGCACGT GGGAATGCAC<br>TGATTTTTCC TAGGAGTAGA CATGTTCCTC<br>TAATTACTCC CTGAGGGTTA GTTGGGGCTA<br>AACCATGACA GAAGTGGGGA AGTTCAATGT<br>CCTTAAATCC ATCTTACTTG CCAACAGGTA<br>AGAGGAAGCT TACATTACAT GTCCAGTCCA<br>CATTTAAAGA GCACTTACTG TGGAACAAGC<br>CTTCAGCCAA ACAATGGGGA TAGAAAAGTA<br>GGTAAGACTC AGCCTTTGTC CAGAGAAGCT<br>CAGGGTATAG CTGAATAGGC AGTTTCTTTT<br>GTCCTGAGGA AAATCAGGAC ATGCCTGCTT<br>TCTAAAAATC TTCCTCTGAA GACCTGACCC<br>AAGCTCTTAA ATGCTATTGT AAGAGAAATT<br>TCTTTGTCTA TTAACTCCAT TTTAGTAGGG<br>ATTCACTGAC TAGATTTTAC TGAACTATGA<br>AAATAAATAC ACATAATTTT TCACAAAATT<br>TTGGGCCCAA TTCCCCTAAA AGAATTGAGG<br>ATTAGGGAGA AAGGAGACAA CTCAAAGTCA<br>TCCCATTAAG TGCAGTTTCT TTGAATCTTC<br>TGCTTTATCT TTAAAAATTT GTATAATTTA<br>TATATTTTAT TCTATGTGTT CCATAGATAT<br>CTTAATGTAA AATTAGTCAT TTAAATTACA<br>CTGTCAATTA AAAGTAATGG GCAAGAGATT<br>GCATCATACT AATTTAGTAA GAACGTTCCC<br>AAATGTTGTA ACAATGTGGA TCATACATCT<br>CTGGTTTTTT AAATGTATTG AGGCTTTCTT<br>GGTGGACTAG TATAGTATAC GGTCAGTTAT<br>GTCAATGTTT CATGGTCAAT AAAAAGGAAG<br>TTGCAAATTG T (SEQ ID NO: 30) |
| Cynomolgus monkey | TSLP amino acid | | YDFTNCDFEKIEADYLRTISKDLITYMSGTKSTD<br>FNNTVSCSNRPHCLTEIQSLTFNPTPRCASLAKE<br>MFARKTKATLALWCPGYSETQINATQAMKKRR<br>KRKVTTNKCLEQVSQLLGLWRRFIRTLLKKQ<br>(SEQ ID NO: 31) |
| Cynomolgus monkey | TSLP mRNA | | TACGACTTCACCAACTGCGACTTCGAGAAGAT<br>CGAGGCCGACTACCTGAGAACCATCAGCAAG<br>GACCTGATCACCTACATGAGCGGCACCAAGA<br>GCACCGACTTCAACAACACCGTGTCCTGCAGC<br>AACAGACCCCACTGCCTGACCGAGATCCAGA<br>GCCTGACCTTCAACCCCACCCCCAGATGTGCC<br>AGCCTGGCCAAAGAGATGTTCGCCAGAAAGA<br>CCAAGGCCACCCTGGCCCTGTGGTGTCCCGGC<br>TACAGCGAGACACAGATCAACGCCACACAGG<br>CCATGAAGAAGCGGCGGAAGCGGAAAGTGAC |

TABLE 1-continued

TSLP amino acid and mRNA sequences

| Species | Isoform | GeneBank Accession No. | Sequence |
|---|---|---|---|
| | | | CACCAACAAGTGCCTGGAACAGGTGTCACAG CTGCTGGGGCTGTGGCGGCGGTTCATCCGGAC CCTGCTGAAGAAGCAG (SEQ ID NO: 32) |
| Mus musculus | TSLP isoform 1 amino acid | NP_067342.1 | MVLLRSLFILQVLVRMGLTYNFSNCNFTSITKIY CNIIFHDLTGDLKGAKFEQIEDCESKPACLLKIEY YTLNPIPGCPSLPDKTFARRTREALNDHCPGYPE TERNDGTQEMAQEVQNICLNQTSQILRLWYSF MQSPE (SEQ ID NO: 33) |
| Mus musculus | TSLP isoform 1 mRNA | NM_021367.2 | CACGTTCAGG CGACAGCATG GTTCTTCTCA GGAGCCTCTT CATCCTGCAA GTACTAGTAC GGATGGGGCT AACTTACAAC TTTTCTAACT GCAACTTCAC GTCAATTACG AAAATATATT GTAACATAAT TTTTCATGAC CTGACTGGAG ATTTGAAAGG GGCTAAGTTC GAGCAAATCG AGGACTGTGA GAGCAAGCCA GCTTGTCTCC TGAAAATCGA GTACTATACT CTCAATCCTA TCCCTGGCTG CCCTTCACTC CCCGACAAAA CATTTGCCCG GAGAACAAGA GAAGCCCTCA ATGACCACTG CCCAGGCTAC CCTGAAACTG AGAGAAATGA CGGTACTCAG GAAATGGCAC AAGAAGTCCA AAACATCTGC CTGAATCAAA CCTCACAAAT TCTAAGATTG TGGTATTCCT TCATGCAATC TCCAGAATAA AATTAGCTTT CAGCTTCTGC TATGAAAATC TCTATCTTGG TTTTAGTGGA CAGAATACTA AGGGTGTGAC ACTTAGAGGA CCACTGGTGT TTATTCTTTA ATTACAGAAG GGATTCTTAA CTTATTTTTT GGCATATCGC TTTTTTCAGT ATAGGTGCTT TAAATGGGAA ATGAGCAATA GACCGTTAAT GGAAATATCT GTACTGTTAA TGACCAGCTT CTGAGAAGTC TTTCTCACCT CCCCTGCACA CACCTTACTC TAGGGCAAAC CTAACTGTAG TAGGAAGAGA ATTGAAAGTA GAAAAAAAAA ATTAAAACCA ATGACAGCAT CTAAACCCTG TTTAAAAGGC AAGGATTTTT CTACCTGTAA TGATTCTTCT AACATTCCTA TGCTAAGATT TTACCAAAGA AGAAAATGAC AGTTCGGGCA GTCACTGCCA TGATGAGGTG GTCTGAAAGA AGATTGTGGA ATCTGGGAGA AACTGCTGAG ATCATATTGC AAATCCAGCT GTCAAAGGGT TCAGACCCAG GACAGTACAA TTCGTGAGCA GATCTCAAGA GCCTTGCACA TCTACGAGAT ATATATTTAA AGTTGTAGAT AATGAATTTC TAATTTATTT TGTGAGCACT TTTGGAAATA TACATGCTAC TTTGTAATGA ATACATTTCT GAATAAAGTA ATTCTCAAGT TTGAAAAAAA AAA (SEQ ID NO: 34) |
| Mus musculus | TSLP isoform 2 mRNA | NR_033206.1 | ACTCTTGCCA GGCACCTCCC TCCTGTGGGT TGATTCCGTT TTCCTCTTCT CAACTGACTC TGGATTCTGA TACCAGACAC CTTCCTGGTG TCTTTCCCTC CTATCCCCAT CCCCTTCCCT GTCCCTTTCA TTCAATTTTT AATATCTGGC GGGTTTTTTT TTTTTTTCT CTCTCTCTGA ACTGTGCCGC TTGTGAGCAG CCAGCTTGTC TCCTGAAAAT CGAGTACTAT ACTCTCAATC CTATCCCTGG CTGCCCTTCA CTCCCCGACA AAACATTTGC CCGGAGAACA AGAGAAGCCC TCAATGACCA CTGCCCAGGC TACCCTGAAA CTGAGAGAAA TGACGGTACT CAGGAAATGG CACAAGAAGT CCAAAACATC TGCCTGAATC AAACCTCACA AATTCTAAGA TTGTGGTATT CCTTCATGCA ATCTCCAGAA TAAAATTAGC TTTCAGCTTC TGCTATGAAA ATCTCTATCT TGGTTTTAGT GGACAGAATA CTAAGGGTGT GACACTTAGA GGACCACTGG TGTTTATTCT TTAATTACAG AAGGGATTCT TAACTTATTT TTTGGCATAT CGCTTTTTTC AGTATAGGTG CTTTAAATGG GAAATGAGCA ATAGACCGTT AATGGAAATA TCTGTACTGT TAATGACCAG CTTCTGAGAA GTCTTTCTCA CCTCCCCTGC ACACACCTTA CTCTAGGGCA AACCTAACTG |

TABLE 1-continued

TSLP amino acid and mRNA sequences

| Species | Isoform | GeneBank Accession No. | Sequence |
|---|---|---|---|
| | | | TAGTAGGAAG AGAATTGAAA GTAGAAAAAA<br>AAAATTAAAA CCAATGACAG CATCTAAACC<br>CTGTTTAAAA GGCAAGGATT TTTCTACCTG<br>TAATGATTCT TCTAACATTC CTATGCTAAG<br>ATTTTACCAA AGAAGAAAAT GACAGTTCGG<br>GCAGTCACTG CCATGATGAG GTGGTCTGAA<br>AGAAGATTGT GGAATCTGGG AGAAACTGCT<br>GAGATCATAT TGCAAATCCA GCTGTCAAAG<br>GGTTCAGACC CAGGACAGTA CAATTCGTGA<br>GCAGATCTCA AGAGCCTTGC ACATCTACGA<br>GATATATATT TAAAGTTGTA GATAATGAAT<br>TTCTAATTTA TTTTGTGAGC ACTTTTGGAA<br>ATATACATGC TACTTTGTAA TGAATACATT<br>TCTGAATAAA GTAATTCTCA AGTTTGAAAA<br>AAAAAA (SEQ ID NO: 35) |
| *Rattus norvegicus* | TSLP amino acid | XP_008770274.1 | MVLFRYLFILQVVRLALTYNFSNCNFEMILRIYH<br>ATIFRDLLKDLNGILFDQIEDCDSRTACLLKIDH<br>HTFNPVPGCPSLPEKAFALKTKAALINYCPGY<br>SETERNGTLEMTREIRNICLNQTSQILGLWLSCIQ<br>S (SEQ ID NO: 36) |
| *Rattus norvegicus* | TSLP mRNA | XM_008772052.1 | TCAGGCAACA GCATGGTTCT TTTCAGGTAC<br>CTCTTTATCC TGCAAGTGGT ACGGCTGGCA<br>CTAACTTACA ACTTTTCTAA CTGTAACTTC<br>GAGATGATTT TGAGAATATA TCATGCAACA<br>ATTTTTCGTG ACCTGCTTAA AGATTTGAAT<br>GGGATCTTGT TCGACCAAAT CGAGGACTGT<br>GACAGCAGGA CAGCTTGTCT CCTGAAAATC<br>GACCACCATA CCTTCAATCC TGTCCCTGGC<br>TGCCCGTCAC TCCCCGAGAA AGCGTTCGCT<br>TTGAAAACGA AAGCGGCCCT CATTAACTAC<br>TGCCCAGGCT ACTCTGAAAC TGAGAGAAAT<br>GGTACTCTGG AAATGACACG AGAAATCAGA<br>AACATCTGCC TGAATCAAAC CTCACAAATT<br>CTAGGATTGT GGCTTTCCTG CATTCAATCT<br>TGAAGAAAAA ATTAGCTTTT GGATTATATT<br>ATGAAAATAT ATATCTTGTT TTTAGTAGAT<br>ATAATACTAA GGGTGTGACA CTTAAAAGAA<br>CACTAATGTT TATTCTTTAA TTATAGAAGG<br>GATTCTTAAC TTATTTTTGG CATATCGTTG<br>TTTAGTGTAG GCGCTTTAAA TGGAAAATGA<br>GCATTACCCC TTTAATGGAA ATAACCGTGC<br>TGTTAATGAT TGGCTTCGGC TTCTGAGCAG<br>TCTTTCTCAC CTCACCTGAG ACACTTTACT<br>CTAGGGCAAA CCTAACTGTA GTAGGAAGAA<br>AATCAAAAGT AGAAAAACAG TTGAAACCAA<br>TGACAGGATC TATACTCCAT TTAAAAGGCA<br>AGAATTTTTG TACCTGTAAT GATTCTTCTA<br>ACATTCCTAC GCTAAGATTT TACTAAAGAA<br>GAAAATAACA GCAGAGGAAA GTGTTCAGGC<br>AGTCACTGCC ATGATGAAGC TGTCAGAATC<br>TGAGAGCTAC TGCTGCAACT GATCGTGTAG<br>TAAATCCAGC TGTAAAGGGG ATCTTAACCC<br>ACCACAGTGG GATGCACAGG CAGATCCCCA<br>AGGGCATTGT GCAGCTGTGA GATATATATT<br>TAAAGTTGTA TATAATGATT TTCTAATTTA<br>TTCCGTGAGC ACCTTTGAAA ATATACATGT<br>CGCTGTGTAA CAAATACACT TCTGAATAAA<br>GTAATTCTCA AGTTC (SEQ ID NO: 37) |

The longer TSLP isoform 1, is linked with the development of airway inflammatory disease (Headley et al., 2009, Journal of immunology 182, 1641-1647; Ying et al., 2005, Journal of immunology 174, 8183-8190). The term "TSLP" as used herein refers to TSLP isoform 1. As used herein, human TSLP protein also encompasses proteins that have over its full length at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with the amino acid sequence of GenBank accession number NP_149024.1. A human TSLP nucleic acid sequence has over its full length at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with the nucleic acid sequence of GenBank accession number NM_033035.4. The sequences of murine, cyno, and other animal TSLP proteins are known in the art (see, for example, Table 1).

The term "antibody," as used herein, refers to a protein, or polypeptide sequence derived from an immunoglobulin molecule that specifically binds to an antigen. Antibodies can be polyclonal or monoclonal, multiple or single chain, or intact immunoglobulins, and may be derived from natural sources or from recombinant sources. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody can be a monoclonal antibody, human antibody, humanized antibody, camelised antibody, or chimeric antibody. The antibodies can be of any isotype (e.g., IgG, IgE, IgM, IgD, IgA and IgY), class (e.g., IgG1, IgG2, IgG3, IgG4, IgA1 and IgA2) or subclass.

The terms "antibody fragment," "antigen-binding fragment", "antigen-binding fragment thereof," "antigen binding portion" of an antibody, and the like, as used herein, refer to one or more fragments of an intact antibody that retain the ability to specifically bind to a given antigen (e.g., TSLP). Antigen binding functions of an antibody can be performed by fragments of an intact antibody. Examples of binding fragments encompassed within the term "antigen binding portion" of an antibody include a Fab fragment, a monovalent fragment consisting of the VL, VH, CL and CH1 domains; a F (ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341: 544-546), which consists of a VH domain; and an isolated complementarity determining region (CDR). Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more "antigen binding portions" of an antibody. These antibody fragments are obtained using conventional techniques known to those of skill in the art, and the fragments are screened for utility in the same manner as are intact antibodies. Antigen binding portions can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies). Antigen binding portions can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8 (10):1057-1062; and U.S. Pat. No. 5,641,870).

The term "epitope" includes any protein determinant capable of specific binding to an immunoglobulin or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational." Conformational and linear epitopes are distinguished in that the binding to the former but not the latter is lost in the presence of denaturing solvents.

The definition of the term "paratope" is derived from the above definition of "epitope" by reversing the perspective. Thus, the term "paratope" as used herein refers to the area or region on an antibody or antibody fragment to which an antigen specifically binds, i.e., to which the antibody or antibody fragment makes physical contact to the antigen.

In the context of an X-ray derived crystal structure defined by spatial coordinates of a complex between an antibody, e.g. a Fab fragment, and its antigen, the term paratope is herein, unless otherwise specified or contradicted by context, specifically defined as antibody residues characterized by having a heavy atom (i.e. a non-hydrogen atom) within a specified distance, for example within a distance of 4 angstrom, from a heavy atom in a target antigen.

The terms "complementarity determining regions" and "CDRs" as used herein refer to the amino acid residues of an antibody or antigen-binding fragment that are responsible for antigen binding.

The term "monovalent antibody" as used herein, refers to an antibody that binds to a single epitope on a target molecule.

The term "bivalent antibody" as used herein, refers to an antibody that binds to two epitopes on at least two identical target molecules. The bivalent antibody may also crosslink the target molecules to one another. A "bivalent antibody" also refers to an antibody that binds to two different epitopes on at least two identical target molecules.

The term "multivalent antibody" refers to a single binding molecule with more than one valency, where "valency" is described as the number of antigen-binding moieties present per molecule of an antibody construct. As such, the single binding molecule can bind to more than one binding site on a target molecule. Examples of multivalent antibodies include, but are not limited to bivalent antibodies, trivalent antibodies, tetravalent antibodies, pentavalent antibodies, and the like, as well as bispecific antibodies and biparatopic antibodies. For example, for TSLP, a multivalent antibody such as a TSLP biparatopic antibody would have a binding moiety that recognizes two different domains of TSLP, respectively.

The term "multivalent antibody" also refers to a single binding molecule that has more than one antigen-binding moiety for two separate target molecules. For example, an antibody that binds to TSLP and a second target molecule that is not TSLP. In one embodiment, a multivalent antibody is a tetravalent antibody that has four epitope binding domains. A tetravalent molecule may be bispecific and bivalent for each binding site on that target molecule.

The term "biparatopic antibody" as used herein, refers to an antibody that binds to two different epitopes on a single target molecule. The term also includes an antibody, which binds to two domains of at least two target molecules, e.g., a tetravalent biparatopic antibody.

The term "bispecific antibody" as used herein, refers to an antibody that binds to two or more different epitopes on at least two different targets.

The phrases "monoclonal antibody" or "monoclonal antibody composition" as used herein refers to polypeptides, including antibodies, bispecific antibodies, etc., that have substantially identical amino acid sequence or are derived from the same genetic source. This term also includes preparations of antibody molecules of single molecular composition. A monoclonal antibody composition displays a single binding specificity and affinity for a particular epitope.

The phrase "human antibody," as used herein, includes antibodies having variable regions in which both the framework and CDR regions are derived from sequences of human origin. Furthermore, if the antibody contains a constant region, the constant region is also derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86). The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S. Department of Health and Human Services (1991), eds. Kabat et al.; A1 Lazikani et al., (1997) J. Mol. Bio. 273:927 948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mal. Biol. 273:927-948.

The human antibodies of the invention may include amino acid residues not encoded by human sequences (e.g., mutations introduced by random or site-specific mutagenesis in vitro or by somatic mutation in vivo, or a conservative substitution to promote stability or manufacturing). However, the term "human antibody" as used herein, is not intended to include antibodies in which CDR sequences derived from the germline of another mammalian species, such as a mouse, have been grafted onto human framework sequences.

The phrase "recombinant human antibody" as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "Fc region" as used herein refers to a polypeptide comprising the CH3, CH2 and at least a portion of the hinge region of a constant domain of an antibody. Optionally, an Fc region may include a CH4 domain, present in some antibody classes. An Fc region, may comprise the entire hinge region of a constant domain of an antibody. In one embodiment, the invention comprises an Fc region and a CH1 region of an antibody. In one embodiment, the invention comprises an Fc region CH3 region of an antibody. In another embodiment, the invention comprises an Fc region, a CH1 region and a Ckappa/lambda region from the constant domain of an antibody. In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Example modifications include additions, deletions or substitutions of one or more amino acids in one or more domains. Such changes may be included to optimize effector function, half-life, etc.

As used herein, the term "affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity. As used herein, the term "high affinity" for an IgG antibody or fragment thereof (e.g., a Fab fragment) refers to an antibody having a knock down of $10^{-8}$ M or less, $10^{-9}$ M or less, or $10^{-10}$ M, or $10^{-11}$ M or less, or $10^{-12}$ M or less, or $10^{-13}$ M or less for a target antigen. However, high affinity binding can vary for other antibody isotypes. For example, high affinity binding for an IgM isotype refers to an antibody having a knock down of $10^{-7}$ M or less, or $10^{-8}$ M or less.

As used herein, the term "avidity" refers to an informative measure of the overall stability or strength of the antibody-antigen complex. It is controlled by three major factors: antibody epitope affinity; the valency of both the antigen and antibody; and the structural arrangement of the interacting parts. Ultimately these factors define the specificity of the antibody, that is, the likelihood that the particular antibody is binding to a precise antigen epitope.

The term "binding specificity" as used herein refers to the ability of an individual antibody combining site to react with one antigenic determinant and not with a different antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody.

The term "treat" and "treatment" refer to both therapeutic treatment and prophylactic or preventive measures, wherein the object is to prevent or slow down an undesired physiological change or disorder. For purpose of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The term "subject" refers to an animal, human or non-human, to whom treatment according to the methods of the present invention is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

An "effective amount" refers to an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A "therapeutically effective amount" of a therapeutic compound (i.e., an effective dosage) depends on the therapeutic compounds selected. The compositions can be administered, for example, from one or more times per day, to one or more times per week, to one or more times per month, to one or more times per year. The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "conservative sequence modifications" refers to amino acid modifications that do not significantly affect or alter the binding characteristics of the antibody or antibody fragment containing the amino acid sequence. Such conservative modifications include amino acid substitutions, additions, and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a molecule, such as an antibody or antibody fragment, of the invention can be replaced with other amino acid residues from the same side chain family and the altered molecule can be tested using the functional assays described herein.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. Percentage of "sequence identity" can be determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. The percentage can be calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. The output is the percent identity of the subject sequence with respect to the query sequence.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. An isolated antibody is substantially free of other antibodies having different antigenic specificities (e.g., an isolated antibody that specifically binds TSLP is substantially free of antibodies that specifically bind antigens other than TSLP). An isolated antibody that specifically binds a target molecule may, however, have cross-reactivity to the same antigens from other species, e.g., an isolated antibody that specifically binds human TSLP may bind TSLP molecules from other species. Moreover, an isolated antibody may be substantially free of other cellular material and/or chemicals.

In some embodiments, the dry powder formulation of the present application comprises core-shell particles comprising: a shell-forming excipient, and a core comprising the API, glass-forming excipients, and a buffer, sometimes also referred to herein as the platform formulation, or shell core platform formulation.

The term "active ingredient", "therapeutically active ingredient", "active agent", "drug" or "drug substance" as used herein means the active ingredient of a pharmaceutical, also known as an active pharmaceutical ingredient (API).

The term "mass median diameter" or "MMD" or "×50" as used herein means the median diameter of a plurality of particles, typically in a polydisperse particle population, i.e., consisting of a range of particle sizes. MMD values as reported herein are determined by laser diffraction (Sympatec Helos, Clausthal-Zellerfeld, Germany), unless the context indicates otherwise. In contrast, $d_g$ represents the geometric diameter for a single particle.

The term "tapped densities" or $\rho_{tapped}$, as used herein refers to a particle density measured according to Method I, as described, for example at www.usp.org/sites/default/files/usp_pdf/EN/USPNF/revisions/m99375-bulk_density_and_tapped_density_of_powders.pdf. Tapped densities represent the closest approximation of particle density, with measured values that are approximately 20% less than the actual particle density.

The term "rugous" as used herein means having numerous wrinkles or creases, i.e., being ridged or wrinkled.

The term "rugosity" as used herein is a measure of the surface roughness of an engineered particle. For the purposes of this invention, rugosity is calculated from the specific surface area obtained from BET measurements, true density obtained from helium pycnometry, and the surface to volume ratio obtained by laser diffraction (Sympatec), viz:

Rugosity=$(SSA \cdot \rho_{true})/S_v$ where $S_v=6/D_{32}$, where $D_{32}$ is the average diameter based on unit surface area. Increases in surface roughness are expected to reduce interparticle cohesive forces, and improve targeting of aerosol to the lungs. Improved lung targeting is expected to reduce interpatient variability, and levels of drug in the oropharynx and systemic circulation. In one or more embodiments, the rugosity $S_v$ is from 3 to 20, e.g., from 5 to 10.

The term "median aerodynamic diameter of the primary particles" or $D_a$ as used herein is calculated from the primary geometric size of the particles determined via laser diffraction (×50), and their tapped density, viz: $D_a=\times50 \, (\rho_{tapped})^{1/2}$.

The term "delivered dose" or "DD" as used herein refers to an indication of the delivery of dry powder from an inhaler device after an actuation or dispersion event from a powder unit. DD is defined as the ratio of the dose delivered by an inhaler device to the nominal or metered dose. The DD is an experimentally determined parameter, and may be determined using an in vitro device set up which mimics patient dosing.

The term "mass median aerodynamic diameter" or "MMAD" as used herein refer to the median aerodynamic size of a plurality of particles, typically in a polydisperse population. The "aerodynamic diameter" is the diameter of a unit density sphere having the same settling velocity, generally in air, as a powder and is therefore a useful way to characterize an aerosolized powder or other dispersed particle or particle formulation in terms of its settling behaviour. The aerodynamic particle size distributions (APSD) and MMAD are determined herein by cascade impaction, using a NEXT GENERATION IMPACTOR™. In general, if the particles are aerodynamically too large, fewer particles will reach the deep lung. If the particles are too small, a larger percentage of the particles may be exhaled. In contrast, $d_a$ represents the aerodynamic diameter for a single particle.

The term "total lung dose" (TLD) as used herein refers to the percentage of active ingredient(s) which is not deposited in an idealized Alberta mouth-throat model following inhalation of powder from a dry powder inhaler at a pressure drop of 4 kPa. Data can be expressed as a percentage of the nominal dose or the delivered dose. The AIT represents an idealized version of the upper respiratory tract for an average adult subject. Unless otherwise stated, TLD is measured in the Alberta idealized throat model. Information on the AIT and a detailed description of the experimental setup can be found at: www.copleyscientific.com.

The term "inertial parameter" as used herein refers to the parameter which characterizes inertial impaction in the upper respiratory tract. The parameter was derived from Stoke's Law and is equal to $d_a^2 Q$, where $d_a$ is the aerodynamic diameter, and Q is the volumetric flow rate.

The term "solids content" as used herein refers to the concentration of active ingredient(s) and excipients dissolved or dispersed in the liquid solution or dispersion to be spray-dried.

The term "ALR" as used herein is a process parameter defining the air to liquid ratio utilized in an atomizer. Smaller ALR values typically produce larger atomized droplets.

The term "particle population density" (PPD) as used herein is a dimensionless number calculated from the product of the solids content and the atomizer liquid flow rate divided by the total dryer gas flow rate. The PPD has been observed to correlate with primary geometric particle size.

TSLP Binding Molecules

Provided herein are molecules, e.g., antibodies or antibody fragments, including Fab, Fab', F(ab')2, Fd, Fv, and dAb fragments, scFvs, single domain antibodies, maxibodies, minibodies, intrabodies, diabodies, triabodies, tetrabodies, v-NARs, and bis-SCFvs, that specifically bind TSLP and inhibit TSLP activity. These molecules are useful for treating TSLP-related inflammatory conditions, including asthma and chronic obstructive pulmonary disease. Since TSLP is a key nodal cytokine upstream of Th2 effector cytokines, inhibition of TSLP can simultaneously block multiple downstream Th2 effectors (e.g., IL-4, IL-5, IL-13) and may also impact non-Th2 mediated pathways (e.g., IL-17, IFN-γ).

TSLP Antibodies and TSLP-Binding Antibody Fragments

In some embodiments, the present invention provides antibodies and antibody fragments that specifically bind to human TSLP. The TSLP antibodies and antibody fragments include, but are not limited to, the human and humanized monoclonal antibodies and antibody fragments generated as described herein, including in the Examples. In some embodiments, the present invention provides an isolated antibody or antigen-binding fragment thereof, which binds human TSLP with a dissociation constant ($K_D$) of less than 100 pM, e.g., a $K_D$ of less than 90 pM, less than 80 pM, less than 70 pM, less than 60 pM, less than 50 pM, less than 40 pM, less than 30 pM, less than 20 pM, less than 10 pM. In some embodiments, the isolated antibodies or antigen-binding fragments provided herein bind human TSLP with a dissociation constant ($K_D$) of less than 10 pM.

In some embodiments, TSLP-binding molecules provided herein include a heavy chain CDR1, a heavy chain CDR2, a heavy chain CDR3, and a light chain CDR1, a light chain CDR2, and a light chain CDR3. In some embodiments, TSLP-binding molecules provided herein include a heavy chain variable region comprising CDR1, CDR2, and CDR3 and a light chain variable region comprising CDR1, CDR2, and CDR3. In some embodiments, the TSLP-binding molecules provided herein include a full length heavy chain sequence and a full length light chain sequence. In some embodiments, the molecule is a TSLP-binding Fab.

Table 2 lists the sequences of exemplary TSLP-binding antibodies and Fabs, all of which bind to human TSLP with high affinity. For example, anti-TSLP Fab1 binds to recombinant human TSLP with a dissociation constant ($K_D$) of 6 pM. In some embodiments, anti-TSLP Fab1 binds to human and cynomolgus monkey TLSP proteins with $K_D$ values of 5.0±2.0 pM and 1.4±0.6 pM, respectively.

TABLE 2

Amino acid sequences of anti-TSLP Fabs and antibodies anti-TSLP mAb1

| | | |
|---|---|---|
| SEQ ID NO: 1 | HCDR1 (Combined) | GFTFSDYWMH |
| SEQ ID NO: 2 | HCDR2 (Combined) | HIKSKTDAGTTDYAAPVKG |
| SEQ ID NO: 3 | HCDR3 (Combined) | EIYYYAFDS |
| SEQ ID NO: 4 | HCDR1 (Kabat) | DYWMH |
| SEQ ID NO: 2 | HCDR2 (Kabat) | HIKSKTDAGTTDYAAPVKG |
| SEQ ID NO: 3 | HCDR3 (Kabat) | EIYYYAFDS |
| SEQ ID NO: 5 | HCDR1 (Chothia) | GFTFSDY |
| SEQ ID NO: 6 | HCDR2 (Chothia) | KSKTDAGT |
| SEQ ID NO: 3 | HCDR3 (Chothia) | EIYYYAFDS |
| SEQ ID NO: 7 | VH | EVQLVESGGGLVKPGGSLRLSCAASGFTFSDY WMHWVRQAPGKGLEWVGHIKSKTDAGTTDY AAPVKGRFTISRDDSKNTLYLQMNSLKTEDTA VYYCAREIYYYAFDSWGQGTLVTVSS |
| SEQ ID NO: 8 | VH DNA | GAGGTTCAGCTGGTGGAATCAGGCGGCGGA CTGGTTAAGCCTGGCGGTAGCCTTAGACTTA GCTGCGCTGCTAGTGGCTTCACCTTTAGCGA CTACTGGATGCACTGGGTTAGACAGGCCCCT GGTAAAGGCTTGGAGTGGGTCGGACACATTA AGTCTAAGACCGACGCCGGCACTACCGACTA CGCCGCTCCCGTTAAGGGCCGGTTCACTATC TCTAGGGACGACTCTAAGAACACCCTCTACC TTCAAATGAATAGCCTTAAGACCGAGGACAC CGCCGTCTACTACTGCGCTAGAGAAATCTAC TACTACGCCTTCGATAGCTGGGGTCAAGGCA CCCTCGTGACCGTGTCTAGC |
| SEQ ID NO: 9 | Heavy Chain | EVQLVESGGGLVKPGGSLRLSCAASGFTFSDY WMHWVRQAPGKGLEWVGHIKSKTDAGTTDY AAPVKGRFTISRDDSKNTLYLQMNSLKTEDTA VYYCAREIYYYAFDSWGQGTLVTVSSASTKGP SVFPLAPSSKSTSGGTAALGCLVKDYFPEPVTV SWNSGALTSGVHTFPAVLQSSGLYSLSSVVTVP SSSLGTQTYICNVNHKPSNTKVDKRVEPKSCD KTHTCPPCPAPELLGGPSVFLFPPKPKDTLMISR TPEVTCVVVDVSHEDPEVKFNWYVDGVEVHN AKTKPREEQYNSTYRVVSVLTVLHQDWLNGK EYKCKVSNKALPAPIEKTISKAKGQPREPQVYT LPPSREEMTKNQVSLTCLVKGFYPSDIAVEWES NGQPENNYKTTPPVLDSDGSFFLYSKLTVDKS RWQQGNVFSCSVMHEALHNHYTQKSLSLSPG K |
| SEQ ID NO: 10 | Heavy Chain DNA | GAGGTTCAGCTGGTGGAATCAGGCGGCGGA CTGGTTAAGCCTGGCGGTAGCCTTAGACTTA GCTGCGCTGCTAGTGGCTTCACCTTTAGCGA CTACTGGATGCACTGGGTTAGACAGGCCCCT GGTAAAGGCTTGGAGTGGGTCGGACACATTA |

TABLE 2-continued

Amino acid sequences of anti-TSLP Fabs and antibodies

|  |  |
|---|---|
|  | AGTCTAAGACCGACGCCGGCACTACCGACTA<br>CGCCGCTCCCGTTAAGGGCCGGTTCACTATC<br>TCTAGGGACGACTCTAAGAACACCCTCTACC<br>TTCAAATGAATAGCCTTAAGACCGAGGACAC<br>CGCCGTCTACTACTGCGCTAGAGAAATCTAC<br>TACTACGCCTTCGATAGCTGGGGTCAAGGCA<br>CCCTCGTGACCGTGTCTAGCGCTAGCACTAA<br>GGGCCCAAGTGTGTTTCCCCTGGCCCCCAGC<br>AGCAAGTCTACTTCCGGCGGAACTGCTGCCC<br>TGGGTTGCCTGGTGAAGGACTACTTCCCCGA<br>GCCCGTGACAGTGTCCTGGAACTCTGGGGCT<br>CTGACTTCCGGCGTGCACACCTTCCCCGCCG<br>TGCTGCAGAGCAGCGGCCTGTACAGCCTGAG<br>CAGCGTGGTGACAGTGCCCTCCAGCTCTCTG<br>GGAACCCAGACCTATATCTGCAACGTGAACC<br>ACAAGCCCAGCAACACCAAGGTGGACAAGA<br>GAGTGGAGCCCAAGAGCTGCGACAAGACCC<br>ACACCTGCCCCCCCTGCCCAGCTCCAGAACT<br>GCTGGGAGGGCCTTCCGTGTTCCTGTTCCCC<br>CCAAGCCCAAGGACACCCTGATGATCAGCAG<br>GACCCCCGAGGTGACCTGCGTGGTGGTGGAC<br>GTGTCCCACGAGGACCCAGAGGTGAAGTTCA<br>ACTGGTACGTGGACGGCGTGGAGGTGCACA<br>ACGCCAAGACCAAGCCCAGAGAGGAGCAGT<br>ACAACAGCACCTACAGGGTGGTGTCCGTGCT<br>GACCGTGCTGCACCAGGACTGGCTGAACGGC<br>AAAGAATACAAGTGCAAAGTCTCCAACAAG<br>GCCCTGCCAGCCCCAATCGAAAAGACAATCA<br>GCAAGGCCAAGGGCCAGCCACGGGAGCCCC<br>AGGTGTACACCCTGCCCCCAGCCGGGAGGA<br>GATGACCAAGAACCAGGTGTCCCTGACCTGT<br>CTGGTGAAGGGCTTCTACCCCAGCGATATCG<br>CCGTGGAGTGGGAGAGCAACGGCCAGCCCG<br>AGAACAACTACAAGACCACCCCCCCAGTGCT<br>GGACAGCGACGGCAGCTTCTTCCTGTACAGC<br>AAGCTGACCGTGGACAAGTCCAGGTGGCAG<br>CAGGGCAACGTGTTCAGCTGCAGCGTGATGC<br>ACGAGGCCCTGCACAACCACTACACCCAGAA<br>GTCCCTGAGCCTGAGCCCCGGCAAG |
| SEQ ID NO: 11 LCDR1 (Combined) | SGDNIGSKYVH |
| SEQ ID NO: 12 LCDR2 (Combined) | GDNERPS |
| SEQ ID NO: 13 LCDR3 (Combined) | QAADWVDFYV |
| SEQ ID NO: 11 LCDR1 (Kabat) | SGDNIGSKYVH |
| SEQ ID NO: 12 LCDR2 (Kabat) | GDNERPS |
| SEQ ID NO: 13 LCDR3 (Kabat) | QAADWVDFYV |
| SEQ ID NO: 14 LCDR1 (Chothia) | DNIGSKY |
| SEQ ID NO: 15 LCDR2 (Chothia) | GDN |
| SEQ ID NO: 16 LCDR3 (Chothia) | ADWVDFY |
| SEQ ID NO: 17 VL | SYELTQPLSVSVALGQTARITCSGDNIGSKYVH<br>WYQQKPGQAPVLVIYGDNERPSGIPERFSGSNS<br>GNTATLTISRAQAGDEADYYCQAADWVDFYV<br>FGGGTKLTVL |
| SEQ ID NO: 18 VL DNA | AGCTACGAGCTGACTCAGCCCCTTAGCGTTA<br>GCGTGGCCCTGGGTCAAACCGCTAGAATCAC<br>CTGTAGCGGCGATAATATCGGCTCTAAATAC<br>GTTCACTGGTATCAGCAGAAGCCCGGTCAAG<br>CCCCCGTGCTCGTGATCTACGGCGATAACGA<br>GCGGCCTAGCGGAATCCCCGAGCGGTTTAGC<br>GGCTCTAATAGCGGTAACACCGCTACCCTGA<br>CTATCTCTAGGGCTCAGGCCGGCGACGAGGC<br>CGACTACTACTGTCAGGCCGCCGACTGGGTG<br>GACTTCTACGTGTTCGGCGGAGGCACTAAGC<br>TGACCGTGCTG |
| SEQ ID NO: 19 Light Chain | SYELTQPLSVSVALGQTARITCSGDNIGSKYVH<br>WYQQKPGQAPVLVIYGDNERPSGIPERFSGSNS<br>GNTATLTISRAQAGDEADYYCQAADWVDFYV |

TABLE 2-continued

Amino acid sequences of anti-TSLP Fabs and antibodies

|  |  |
|---|---|
|  | FGGGTKLTVLGQPKAAPSVTLFPPSSEELQANK<br>ATLVCLISDFYPGAVTVAWKADSSPVKAGVET<br>TTPSKQSNNKYAASSYLSLTPEQWKSHRSYSC<br>QVTHEGSTVEKTVAPTECS |
| SEQ ID NO: 20 Light Chain DNA | AGCTACGAGCTGACTCAGCCCCTTAGCGTTA<br>GCGTGGCCCTGGGTCAAACCGCTAGAATCAC<br>CTGTAGCGGCGATAATATCGGCTCTAAATAC<br>GTTCACTGGTATCAGCAGAAGCCCGGTCAAG<br>CCCCCGTGCTCGTGATCTACGGCGATAACGA<br>GCGGCCTAGCGGAATCCCCGAGCGGTTTAGC<br>GGCTCTAATAGCGGTAACACCGCTACCCTGA<br>CTATCTCTAGGGCTCAGGCCGGCGACGAGGC<br>CGACTACTACTGTCAGGCCGCCGACTGGGTG<br>GACTTCTACGTGTTCGGCGGAGGCACTAAGC<br>TGACCGTGCTGGGTCAACCTAAGGCTGCCCC<br>CAGCGTGACCCTGTTCCCCCCCAGCAGCGAG<br>GAGCTGCAGGCCAACAAGGCCACCCTGGTGT<br>GCCTGATCAGCGACTTCTACCCAGGCGCCGT<br>GACCGTGGCCTGGAAGGCCGACAGCAGCCC<br>CGTGAAGGCCGGCGTGGAGACCACCACCCCC<br>AGCAAGCAGAGCAACAACAAGTACGCCGCC<br>AGCAGCTACCTGAGCCTGACCCCCGAGCAGT<br>GGAAGAGCCACAGGTCCTACAGCTGCCAGGT<br>GACCCACGAGGGCAGCACCGTGGAAAAGAC<br>CGTGGCCCCAACCGAGTGCAGC | anti-TSLP
Fab1

| SEQ ID NO: 1 HCDR1 (Combined) | GFTFSDYWMH |
|---|---|
| SEQ ID NO: 2 HCDR2 (Combined) | HIKSKTDAGTTDYAAPVKG |
| SEQ ID NO: 3 HCDR3 (Combined) | EIYYYAFDS |
| SEQ ID NO: 4 HCDR1 (Kabat) | DYWMH |
| SEQ ID NO: 2 HCDR2 (Kabat) | HIKSKTDAGTTDYAAPVKG |
| SEQ ID NO: 3 HCDR3 (Kabat) | EIYYYAFDS |
| SEQ ID NO: 5 HCDR1 (Chothia) | GFTFSDY |
| SEQ ID NO: 6 HCDR2 (Chothia) | KSKTDAGT |
| SEQ ID NO: 3 HCDR3 (Chothia) | EIYYYAFDS |
| SEQ ID NO: 7 VH | EVQLVESGGGLVKPGGSLRLSCAASGFTFSDY<br>WMHWVRQAPGKGLEWVGHIKSKTDAGTTDY<br>AAPVKGRFTISRDDSKNTLYLQMNSLKTEDTA<br>VYYCAREIYYYAFDSWGQGTLVTVSS |
| SEQ ID NO: 21 VH DNA | GAGGTGCAGCTGGTGGAATCAGGCGGCGGA<br>CTGGTCAAGCCTGGCGGTAGCCTGAGACTGA<br>GCTGCGCTGCTAGTGGCTTCACCTTTAGCGA<br>CTACTGGATGCACTGGGTCAGACAGGCCCCT<br>GGTAAAGGCCTGGAGTGGGTCGGACACATTA<br>AGTCTAAGACCGACGCCGGCACTACCGACTA<br>CGCCGCTCCTGTGAAGGGCCGGTTCACTATC<br>TCTAGGGACGACTCTAAGAACACCCTGTACC<br>TGCAGATGAATAGCCTGAAAACCGAGGACA<br>CCGCCGTCTACTACTGCGCTAGAGAGATCTA<br>CTACTACGCCTTCGATAGCTGGGGTCAGGGC<br>ACCCTGGTCACCGTGTCTAGC |
| SEQ ID NO: 22 Heavy Chain | EVQLVESGGGLVKPGGSLRLSCAASGFTFSDY<br>WMHWVRQAPGKGLEWVGHIKSKTDAGTTDY<br>AAPVKGRFTISRDDSKNTLYLQMNSLKTEDTA<br>VYYCAREIYYYAFDSWGQGTLVTVSSASTKGP<br>SVFPLAPSSKSTSGGTAALGCLVKDYFPEPVTV<br>SWNSGALTSGVHTFPAVLQSSGLYSLSSVVTVP<br>SSSLGTQTYICNVNHKPSNTKVDKRVEPKSC |
| SEQ ID NO: 23 Heavy Chain DNA | GAGGTGCAGCTGGTGGAATCAGGCGGCGGA<br>CTGGTCAAGCCTGGCGGTAGCCTGAGACTGA<br>GCTGCGCTGCTAGTGGCTTCACCTTTAGCGA<br>CTACTGGATGCACTGGGTCAGACAGGCCCCT |

TABLE 2-continued

Amino acid sequences of anti-TSLP Fabs and antibodies

|  |  |
|---|---|
| | GGTAAAGGCCTGGAGTGGGTCGGACACATTA<br>AGTCTAAGACCGACGCCGGCACTACCGACTA<br>CGCCGCTCCTGTGAAGGGCCGGTTCACTATC<br>TCTAGGGACGACTCTAAGAACACCCTGTACC<br>TGCAGATGAATAGCCTGAAAACCGAGGACA<br>CCGCCGTCTACTACTGCGCTAGAGAGATCTA<br>CTACTACGCCTTCGATAGCTGGGGTCAGGGC<br>ACCCTGGTCACCGTGTCTAGCGCTAGCACTA<br>AGGGCCCCTCCGTGTTCCCTCTGGCCCCTTCC<br>AGCAAGTCTACCTCTGGCGGCACCGCTGCTC<br>TGGGCTGCCTGGTGAAGGACTACTTCCCTGA<br>GCCTGTGACAGTGTCCTGGAACTCTGGCGCC<br>CTGACCTCCGGCGTGCACACCTTCCCTGCCG<br>TGCTGCAGTCCTCCGGCCTGTACTCCCTGTCC<br>TCCGTGGTGACAGTGCCTTCCTCCAGCCTGG<br>GCACCCAGACCTATATCTGCAACGTGAACCA<br>CAAGCCTTCCAACACCAAGGTGGACAAGCG<br>GGTGGAGCCTAAGTCATGC |
| SEQ ID NO: 11 LCDR1 (Combined) | SGDNIGSKYVH |
| SEQ ID NO: 12 LCDR2 (Combined) | GDNERPS |
| SEQ ID NO: 13 LCDR3 (Combined) | QAADWVDFYV |
| SEQ ID NO: 11 LCDR1 (Kabat) | SGDNIGSKYVH |
| SEQ ID NO: 12 LCDR2 (Kabat) | GDNERPS |
| SEQ ID NO: 13 LCDR3 (Kabat) | QAADWVDFYV |
| SEQ ID NO: 14 LCDR1 (Chothia) | DNIGSKY |
| SEQ ID NO: 15 LCDR2 (Chothia) | GDN |
| SEQ ID NO: 16 LCDR3 (Chothia) | ADWVDFY |
| SEQ ID NO: 17 VL | SYELTQPLSVSVALGQTARITCSGDNIGSKYVH<br>WYQQKPGQAPVLVIYGDNERPSGIPERFSGSNS<br>GNTATLTISRAQAGDEADYYCQAADWVDFYV<br>FGGGTKLTVL |
| SEQ ID NO: 24 VL DNA | AGCTACGAGCTGACTCAGCCCCTGAGCGTCA<br>GCGTGGCCCTGGGTCAGACCGCTAGAATCAC<br>CTGTAGCGGCGATAATATCGGCTCTAAATAC<br>GTGCACTGGTATCAGCAGAAGCCCGGTCAGG<br>CCCCCGTGCTGGTGATCTACGGCGATAACGA<br>GCGGCCTAGCGGAATCCCCGAGCGGTTTAGC<br>GGCTCTAATAGCGGTAACACCGCTACCCTGA<br>CTATCTCTAGGGCTCAGGCCGGCGACGAGGC<br>CGACTACTACTGTCAGGCCGCCGACTGGGTG<br>GACTTCTACGTGTTCGGCGGAGGCACTAAGC<br>TGACCGTGCTG |
| SEQ ID NO: 25 Light Chain | SYELTQPLSVSVALGQTARITCSGDNIGSKYVH<br>WYQQKPGQAPVLVIYGDNERPSGIPERFSGSNS<br>GNTATLTISRAQAGDEADYYCQAADWVDFYV<br>FGGGTKLTVLGQPKAAPSVTLFPPSSEELQANK<br>ATLVCLISDFYPGAVTVAWKADSSPVKAGVET<br>TTPSKQSNNKYAASSYLSLTPEQWKSHRSYSC<br>QVTHEGSTVEKTVAPTECS |
| SEQ ID NO: 26 Light Chain DNA | AGCTACGAGCTGACTCAGCCCCTGAGCGTCA<br>GCGTGGCCCTGGGTCAGACCGCTAGAATCAC<br>CTGTAGCGGCGATAATATCGGCTCTAAATAC<br>GTGCACTGGTATCAGCAGAAGCCCGGTCAGG<br>CCCCCGTGCTGGTGATCTACGGCGATAACGA<br>GCGGCCTAGCGGAATCCCCGAGCGGTTTAGC<br>GGCTCTAATAGCGGTAACACCGCTACCCTGA<br>CTATCTCTAGGGCTCAGGCCGGCGACGAGGC<br>CGACTACTACTGTCAGGCCGCCGACTGGGTG<br>GACTTCTACGTGTTCGGCGGAGGCACTAAGC<br>TGACCGTGCTGGGTCAGCCTAAGGCTGCCCC<br>CAGCGTGACCCTGTTCCCCCCCAGCAGCGAG<br>GAGCTGCAGGCCAACAAGGCCACCCTGGTGT<br>GCCTGATCAGCGACTTCTACCCAGGCGCCGT<br>GACCGTGGCCTGGAAGGCCGACAGCAGCCC<br>CGTGAAGGCCGGCGTGGAGACCACCACCCCC |

TABLE 2-continued

Amino acid sequences of anti-TSLP Fabs and antibodies

```
AGCAAGCAGAGCAACAACAAGTACGCCGCC
AGCAGCTACCTGAGCCTGACCCCCGAGCAGT
GGAAGAGCCACAGGTCCTACAGCTGCCAGGT
GACCCACGAGGGCAGCACCGTGGAAAAGAC
CGTGGCCCCAACCGAGTGCAGC
```

In some embodiments, the antibodies comprising a VH CDR having an amino acid sequence of any one of the VH CDRs listed in Table 2. In particular, the invention provides antibodies that specifically bind to TSLP protein, said antibodies comprising (or alternatively, consisting of) one, two, three, four, five or six VH CDRs having an amino acid sequence of any of the VH CDRs listed in Table 2. The present invention also provides antibodies that specifically bind to TSLP protein, said antibodies comprising a VL CDR having an amino acid sequence of any one of the VL CDRs listed in Table 2. In particular, the invention provides antibodies that specifically bind to TSLP protein, said antibodies comprising (or alternatively, consisting of) one, two, three, four, five or six VL CDRs having an amino acid sequence of any of the VL CDRs listed in Table 2.

The invention also provides antibodies and antigen-binding fragments thereof comprising (or alternatively, consisting of) a VH amino acid sequence listed in Table 2, wherein no more than about 1, 2, 3, 4, 5, 6, 7, 8, 9, 10, 11, 12, 13, 14, 15, 16, 17, 18, 19, or 20 amino acids in a framework sequence (for example, a sequence which is not a CDR) have been mutated (wherein a mutation is, as various non-limiting examples, an addition, substitution or deletion).

The invention also provides antibodies and antigen-binding fragments thereof that specifically bind to TSLP, said antibodies or antigen-binding fragments thereof comprising (or alternatively, consisting of) a VL amino acid sequence listed in Table 2, wherein no more than about 1, 2, 3, 4, 5, 6, 7, 8, 9, 10, 11, 12, 13, 14, 15, 16, 17, 18, 19, or 20 amino acids in a framework sequence (for example, a sequence which is not a CDR) have been mutated (wherein a mutation is, as various non-limiting examples, an addition, substitution or deletion).

Other antibodies and antigen-binding fragments thereof of the invention include amino acids that have been mutated, yet have at least 60, 70, 80, 90, 91, 92, 93, 94, 95, 96, 97, 98 or 99 percent identity in the CDR regions with the CDR regions depicted in the sequences described in Table 2 and are able to bind to TSLP. In one aspect, other antibodies and antigen-binding fragments thereof of the invention include mutant amino acid sequences wherein no more than 1, 2, 3, 4 or 5 amino acids have been mutated in the CDR regions when compared with the CDR regions depicted in the sequences described in Table 2.

The present invention also provides nucleic acid sequences that encode VH, VL, the full length heavy chain, and the full length light chain of the antibodies and antigen-binding fragments thereof that specifically bind to TSLP protein. Such nucleic acid sequences can be optimized for expression in mammalian cells.

Other TSLP antibodies and antigen-binding fragments thereof include those wherein the amino acids or nucleic acids encoding the amino acids have been mutated, yet have at least 60, 70, 80, 90 or 95 percent identity to the sequences described in Table 2. In one embodiment, the antibodies and antigen-binding fragments thereof include mutant amino acid sequences wherein no more than 1, 2, 3, 4 or 5 amino acids have been mutated in the variable regions when compared with the variable regions depicted in the sequence described in Table 2, while retaining substantially the same therapeutic activity.

Since each of the antibodies disclosed herein can bind to TSLP, the VH, VL, full length light chain, and full length heavy chain sequences (amino acid sequences and the nucleotide sequences encoding the amino acid sequences) can be "mixed and matched" to create other TSLP-binding antibodies and antigen-binding fragments thereof of the invention. Such "mixed and matched" TSLP-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

In another aspect, the present invention provides TSLP-binding antibodies that comprise the heavy chain and light chain CDR1s, CDR2s and CDR3s as described in Table 2, or combinations thereof. The CDR regions are delineated using the Kabat system (Kabat et al. 1991 Sequences of Proteins of Immunological Interest, Fifth Edition, U.S. Department of Health and Human Services, NIH Publication No. 91-3242), or using the Chothia system (Chothia et al. 1987 J. Mol. Biol. 196: 901-917; and Al-Lazikani et al. 1997 J. Mol. Biol. 273: 927-948). Other methods for delineating the CDR regions may alternatively be used. For example, the CDR definitions of both Kabat and Chothia may be combined.

Given that each of these antibodies can bind to TSLP and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other TSLP-binding binding molecules of the invention. Such "mixed and matched" TSLP-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence (s). Likewise, when VL CDR sequences are mixed and matched, the CDR1, CDR2 and/or CDR3 sequence from a particular VL sequence should be replaced with a structurally similar CDR sequence (s). It will be readily apparent to the ordinarily skilled artisan that novel VH and VL sequences can be created by mutating one or more VH and/or VL CDR region sequences with structurally similar sequences from the CDR sequences shown herein for monoclonal antibodies of the present invention.

Accordingly, the present invention provides an isolated monoclonal antibody or antigen binding fragment thereof comprising a heavy chain variable region CDR1 (HCDR1) comprising an amino acid sequence selected from any of SEQ ID NO: 1, 4, or 5; a heavy chain variable region CDR2 (HCDR2) comprising an amino acid sequence selected from any of SEQ ID NO: 2 or 6; a heavy chain variable region CDR3 (HCDR3) comprising an amino acid sequence of SEQ ID NO: 3; a light chain variable region CDR1 (LCDR1) comprising an amino acid sequence selected from any of SEQ ID NO: 11 or 14; a light chain variable region CDR2 (LCDR2) comprising an amino acid sequence selected from any of SEQ ID NO: 12 or 15; and a light chain variable region CDR3 (LCDR3) comprising an amino acid sequence selected from any of SEQ ID NO: 13 or 16; wherein the antibody or antibody fragment specifically binds TSLP.

In some embodiments, an antibody or antibody fragment that specifically binds to TSLP is an antibody or antibody fragment described in Table 2.

In some embodiments, the present invention provides an isolated antibody or antigen-binding fragment thereof, which binds human TSLP and comprises the HCDR1, HCDR2, and HCDR3 sequences of SEQ ID NOs: 4, 2, and 3, respectively, and the LCDR1, LCDR2, and LCDR3 sequences of SEQ ID NOs: 11, 12, and 13, respectively.

In some embodiments, the present invention provides an isolated antibody or antigen-binding fragment thereof, which binds human TSLP and comprises the HCDR1, HCDR2, and HCDR3 sequences of SEQ ID NOs: 5, 6, and 3, respectively, and the LCDR1, LCDR2, and LCDR3 sequences of SEQ ID NOs: 14, 15, and 16, respectively.

In some embodiments, the present invention provides an isolated antibody or antigen-binding fragment thereof, which binds human TSLP and comprises the HCDR1, HCDR2, and HCDR3 sequences of SEQ ID NOs: 1, 2, and 3, respectively, and the LCDR1, LCDR2, and LCDR3 sequences of SEQ ID NOs: 11, 12, and 13, respectively.

In some embodiments, the present invention provides an isolated antibody or antigen-binding fragment thereof, which binds human TSLP and comprises a VH comprising the amino acid sequence of SEQ ID NO: 7, and a VL comprising the amino acid sequence of SEQ ID NO: 17.

In some embodiments, the present invention provides an isolated antibody or antigen-binding fragment thereof, which binds human TSLP and comprises a heavy chain comprising the amino acid sequence of SEQ ID NO: 22, and a light chain comprising the amino acid sequence of SEQ ID NO: 25.

In some embodiments, the present invention provides an isolated antibody or antigen-binding fragment thereof, which binds human TSLP and comprises a heavy chain comprising the amino acid sequence of SEQ ID NO: 9, and a light chain comprising the amino acid sequence of SEQ ID NO: 19.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, the present invention provides an antibody or an antigen-binding fragment thereof comprising amino acid sequences that are homologous to the sequences described in Table 2, and said antibody binds to TSLP, and retains the desired functional properties of those antibodies described in Table 2.

For example, the invention provides an isolated monoclonal antibody (or an antigen-binding fragment thereof) comprising a heavy chain variable region (VH) and a light chain variable region (VL), wherein VH comprises an amino acid sequence that is at least 80%, at least 90%, or at least 95% identical to an amino acid sequence selected from the group consisting of SEQ ID NO: 7; the VL comprises an amino acid sequence that is at least 80%, at least 90%, or at least 95% identical to an amino acid sequence selected from the group consisting of SEQ ID NO: 17; the antibody specifically binds to TSLP protein and inhibits TSLP.

In one embodiment, the VH and/or VL amino acid sequences may be 50%, 60%, 70%, 80%, 90%, 95%, 96%, 97%, 98% or 99% identical to the sequences set forth in Table 2. In one embodiment, the VH and/or VL amino acid sequences may be identical except an amino acid substitution in no more than 1, 2, 3, 4 or 5 amino acid positions. An antibody having VH and VL regions having high (i.e., 80% or greater) identity to the VH and VL regions of those described in Table 2 can be obtained by mutagenesis (e.g., site-directed or PCR-mediated mutagenesis) of nucleic acid molecules encoding SEQ ID NO: 8 or 21, or SEQ ID NO: 18 or 24, respectively, followed by testing of the encoded altered antibody for retained function using the functional assays described herein.

In one embodiment, the full length heavy chain and/or full length light chain amino acid sequences may be 50%, 60%, 70%, 80%, 90%, 95%, 96%, 97%, 98% or 99% identical to the sequences set forth in Table 2. An antibody having a full length heavy chain and full length light chain having high (i.e., 80% or greater) identity to the full length heavy chain of SEQ ID NO: 9; and full length light chain of SEQ ID NO: 19, can be obtained by mutagenesis (e.g., site-directed or PCR-mediated mutagenesis) of nucleic acid molecules encoding such polypeptides respectively, followed by testing of the encoded altered antibody for retained function using the functional assays described herein.

In one embodiment, the full length heavy chain and/or full length light chain nucleotide sequences may be 60%, 70%, 80%, 90%, 95%, 96%, 97%, 98% or 99% identical to the sequences set forth in Table 2.

In one embodiment, the variable regions of heavy chain and/or light chain nucleotide sequences may be 60%, 70%, 80%, 90%, 95%, 96%, 97%, 98% or 99% identical to the sequences set forth in Table 2.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In some embodiments, an antibody or antigen-binding fragment thereof of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the TSLP-binding antibodies and antigen-binding fragments thereof of the invention. Accordingly, the invention provides an isolated monoclonal antibody, or an antigen-binding fragment thereof, consisting of a heavy chain variable region comprising CDR1, CDR2, and CDR3 sequences and a light chain variable region comprising CDR1, CDR2, and CDR3 sequences, wherein: a heavy chain variable region CDR1 comprising an amino acid sequence selected from any of SEQ ID NO: 1, 4, or 5, or conservative variants thereof; a heavy chain variable region CDR2 comprising an amino acid sequence selected from any of SEQ ID NO: 2 or 6, or conservative variants thereof; a heavy chain variable region CDR3 comprising an amino acid sequence of SEQ ID NO: 3, or conservative variants thereof; a light chain variable region CDR1 comprising an amino acid sequence selected from any of SEQ ID NO: 11 or 14, or conservative variants thereof; a light chain variable region CDR2 comprising an amino acid sequence selected from any of SEQ ID NO: 12 or 15, or conservative variants thereof; and a light chain variable region CDR3 comprising an amino acid sequence selected from any of SEQ ID NO: 13 or 16, or conservative variants thereof; the antibody or the antigen-binding fragment thereof specifically binds to TSLP and inhibits TSLP.

In some embodiments, an antibody or antigen-binding fragment thereof of the invention has a heavy chain variable region and a light chain variable region, wherein the heavy and light chain variable regions have specified amino acid sequences based on the antibodies described herein or conservative modifications thereof, and wherein the antibodies retain the desired functional properties of the TSLP-binding antibodies and antigen-binding fragments thereof of the invention. Accordingly, the invention provides an isolated monoclonal antibody, or an antigen-binding fragment thereof, consisting of a heavy chain variable region and a light chain variable region, wherein: the heavy chain variable region comprising an amino acid sequence of SEQ ID NO: 7, or conservative variants thereof; a light chain variable region comprising an amino acid sequence of SEQ ID NO: 17, or conservative variants thereof; the antibody or the antigen-binding fragment thereof specifically binds to TSLP and inhibits TSLP.

Antibodies that Bind to the Same Epitope

The present invention provides antibodies that bind to the same epitope as do the TSLP-binding antibodies or antibody fragments listed in Table 2. Additional antibodies can therefore be identified based on their ability to cross-compete (e.g., to competitively inhibit the binding of, in a statistically significant manner) with other antibodies and antigen-binding fragments thereof of the invention in TSLP binding assays. The ability of a test antibody to inhibit the binding of antibodies and antigen-binding fragments thereof of the present invention to TSLP protein demonstrates that the test antibody can compete with that antibody for binding to TSLP; such an antibody may, according to non-limiting theory, bind to the same or a related (e.g., a structurally similar or spatially proximal) epitope on TSLP as the antibody with which it competes. In some embodiments, the antibody that binds to the same epitope on TSLP as the antibodies and antigen-binding fragments thereof disclosed herein is a human monoclonal antibody. Such human monoclonal antibodies can be prepared and isolated as described herein. In some embodiments, the antibody that binds to the same epitope on TSLP as the antibodies and antigen-binding fragments thereof of the present invention is a mouse monoclonal antibody. In certain embodiments the antibody that binds to the same epitope on TSLP as the antibodies and antigen-binding fragments thereof disclosed herein, is a humanized monoclonal antibody derived from the mouse monoclonal antibodies. In a certain embodiment, the antibody that binds to the same epitope on TSLP as the antibodies and antigen-binding fragments thereof disclosed herein is a humanized monoclonal antibody. Such humanized monoclonal antibodies can be prepared and isolated as described herein.

In some embodiments, a monoclonal antibody provided herein, or an antigen-binding fragment thereof, specifically binds an epitope in human TSLP, wherein the epitope comprises one or more of the following residues: Lys38, Ala41, Leu44, Ser45, Thr46, Ser48, Lys49, Ile52, Thr53, Ser56, Gly57, Thr58, Lys59, Lys101, Gln145, and Arg149 of SEQ ID NO: 38. In some embodiments, a monoclonal antibody provided herein, or an antigen-binding fragment thereof, specifically binds an epitope in human TSLP, wherein the epitope comprises at least one, at least two, at least three, at least four, at least five, at least six, at least seven, at least eight, at least nine, at least ten, at least eleven, at least twelve, at least thirteen, at least fourteen, at least fifteen, or all of the following residues: Lys38, Ala41, Leu44, Ser45, Thr46, Ser48, Lys49, Ile52, Thr53, Ser56, Gly57, Thr58, Lys59, Lys101, Gln145, and Arg149 of SEQ ID NO: 38.

In some embodiments, a monoclonal antibody provided herein, or an antigen-binding fragment thereof, specifically binds an epitope in human TSLP, wherein the epitope comprises at least one, at least two, at least three, at least four, at least five, at least six, at least seven, at least eight, or all of the following residues: Lys38, Ala41, Leu44, Ser45, Thr46, Ser48, Lys49, Ile52, and Thr53 of SEQ ID NO: 38. The epitope of such a monoclonal antibody or antigen-binding fragment thereof can also include one or more of the following residues: Ser56, Gly57, Thr58, Lys59, Lys101, Gln145, and Arg149 of SEQ ID NO: 38.

In some embodiments, a monoclonal antibody provided herein, or an antigen-binding fragment thereof, specifically binds an epitope in human TSLP, wherein the epitope comprises at least one, at least two, at least three, or all of the following residues: Ser56, Gly57, Thr58, and Lys59 of SEQ ID NO: 38. The epitope of such a monoclonal antibody or antigen-binding fragment thereof can also include one or more of the following residues: Lys38, Ala41, Leu44, Ser45, Thr46, Ser48, Lys49, Ile52, Thr53, Lys101, Gln145, and Arg149 of SEQ ID NO: 38.

In some embodiments, a monoclonal antibody provided herein, or an antigen-binding fragment thereof, specifically binds an epitope in human TSLP, wherein the epitope comprises Lys101 of SEQ ID NO: 38. The epitope of such a monoclonal antibody or antigen-binding fragment thereof can also include one or more of the following residues: Lys38, Ala41, Leu44, Ser45, Thr46, Ser48, Lys49, Ile52, Thr53, Ser56, Gly57, Thr58, Lys59, Gln145, and Arg149 of SEQ ID NO: 38.

In some embodiments, a monoclonal antibody provided herein, or an antigen-binding fragment thereof, specifically binds an epitope in human TSLP, wherein the epitope comprises Gln145 or Arg149 of SEQ ID NO: 38. In some embodiments, a monoclonal antibody provided herein, or an antigen-binding fragment thereof, specifically binds an epitope in human TSLP, wherein the epitope comprises Gln145 and Arg149 of SEQ ID NO: 38. The epitope of such a monoclonal antibody or antigen-binding fragment thereof can also include one or more of the following residues: Lys38, Ala41, Leu44, Ser45, Thr46, Ser48, Lys49, Ile52, Thr53, Ser56, Gly57, Thr58, Lys59, and Lys101 of SEQ ID NO: 38.

In some embodiments, a monoclonal antibody provided herein, or an antigen-binding fragment thereof, specifically binds an epitope in human TSLP, wherein the epitope comprises at least one, at least two, at least three, at least four, at least five, at least six, or all of the following residues: Lys49, Ile52, Gly57, Lys59, Lys101, Gln145, and Arg149 of SEQ ID NO: 38. In some embodiments, a monoclonal antibody provided herein, or an antigen-binding fragment thereof, specifically binds an epitope in human TSLP, wherein the epitope comprises all of the following residues: Lys49, Ile52, Gly57, Lys59, Lys101, Gln145, and Arg149 of SEQ ID NO: 38.

In some embodiments, a monoclonal antibody provided herein, or an antigen-binding fragment thereof, specifically binds an epitope in human TSLP, wherein the epitope comprises at least one of the following sets of residues of SEQ ID NO: 38: (a) Lys49 and Ile52, (b) Gly57 and Lys59, (c) Lys101, (d) Gln145 and Arg149. In some embodiments, a monoclonal antibody provided herein, or an antigen-binding fragment thereof, specifically binds an epitope in human TSLP, wherein the epitope comprises Lys49 and Ile52 of SEQ ID NO: 38. In some embodiments, a monoclonal antibody provided herein, or an antigen-binding fragment thereof, specifically binds an epitope in human TSLP, wherein the epitope comprises Gly57 and Lys59 of SEQ ID NO: 38. In some embodiments, a monoclonal antibody provided herein, or an antigen-binding fragment thereof, specifically binds an epitope in human TSLP, wherein the epitope comprises Lys101 of SEQ ID NO: 38. In some embodiments, a monoclonal antibody provided herein, or an antigen-binding fragment thereof, specifically binds an epitope in human TSLP, wherein the epitope comprises Gln145 and Arg149 of SEQ ID NO: 38.

In some embodiments, the TSLP-binding molecules can comprise a paratope comprising at least one, at least two, at least three, at least four, at least five, at least six, at least seven, at least eight, at least nine, at least 10, at least 11, at least 12, at least 13, at least 14, at least 15, at least 16, at least 17, at least 18, at least 19, or all of the following residues: Thr28, Asp31, Tyr32, Trp33, Asp56, Glu101, Ile102, Tyr103, Tyr104, Tyr105 of a heavy chain sequence of SEQ ID NO:22 or Gly28, Ser29, Lys30, Tyr31, Tyr48, Asp50, Asn51, Glu52, Asn65, and Trp92 of a light chain sequence of SEQ ID NO:25.

Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in International Patent Application No. WO 2003/48731. As will be appreciated by one of skill in the art, practically anything to which an antibody can specifically bind could be an epitope. An epitope can comprises those residues to which the antibody binds.

Generally, antibodies specific for a particular target antigen will preferentially recognize an epitope on the target antigen in a complex mixture of proteins and/or macromolecules.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids TSLP such as by, e.g., hydrogen/deuterium exchange, x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157:105-132; for hydropathy plots.

Engineered and Modified Antibodies

An antibody of the invention further can be prepared using an antibody having one or more of the VH and/or VL sequences as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Such framework sequences can be obtained from public DNA databases or published references that include germine antibody gene sequences or rearranged antibody sequences. For example, germine DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are expressly incorporated herein by reference. For example, germline DNA sequences for human heavy and light chain variable region genes and rearranged antibody sequences can be found in "IMGT" database (available on the Internet at www.imgt.org; see Lefranc, M. P. et al., 1999 Nucleic Acids Res. 27:209-212; the contents of each of which are expressly incorporated herein by reference.)

An example of framework sequences for use in the antibodies and antigen-binding fragments thereof of the invention are those that are structurally similar to the framework sequences used by selected antibodies and antigen-binding fragments thereof of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation (s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

A wide variety of antibody/immunoglobulin frameworks or scaffolds can be employed so long as the resulting polypeptide includes at least one binding region which specifically binds to TSLP. Such frameworks or scaffolds include the 5 main idiotypes of human immunoglobulins, antigen-binding fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to a method of generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target TSLP protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, UK, and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (SciI Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity for those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel alpha-helices and a beta-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of Pieris *Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The human TSLP-binding antibodies can be generated using methods that are known in the art. For example, the humaneering technology used to converting non-human antibodies into engineered human antibodies. U.S. Patent Publication No. 20050008625 describes an in vivo method for replacing a nonhuman antibody variable region with a human variable region in an antibody while maintaining the same or providing better binding characteristics relative to that of the nonhuman antibody. The method relies on epitope guided replacement of variable regions of a non-human reference antibody with a fully human antibody. The resulting human antibody is generally unrelated structurally to the reference nonhuman antibody, but binds to the same epitope on the same antigen as the reference antibody. Briefly, the serial epitope-guided complementarity replacement approach is enabled by setting up a competition in cells between a "competitor" and a library of diverse hybrids of the reference antibody ("test antibodies") for binding to limiting amounts of antigen in the presence of a reporter system which responds to the binding of test antibody to antigen. The competitor can be the reference antibody or derivative thereof such as a single-chain Fv fragment. The competitor can also be a natural or artificial ligand of the antigen which binds to the same epitope as the reference antibody. The only requirements of the competitor are that it binds to the same epitope as the reference antibody, and that it competes with the reference antibody for antigen binding. The test antibodies have one antigen-binding V-region in common from the nonhuman reference antibody, and the other V-region selected at random from a diverse source such as a repertoire library of human antibodies. The common V-region from the reference antibody serves as a guide, positioning the test antibodies on the same epitope on the antigen, and in the same orientation, so that selection is biased toward the highest antigen-binding fidelity to the reference antibody.

Many types of reporter systems can be used to detect desired interactions between test antibodies and antigen. For example, complementing reporter fragments may be linked to antigen and test antibody, respectively, so that reporter activation by fragment complementation only occurs when the test antibody binds to the antigen. When the test antibody- and antigen-reporter fragment fusions are co-expressed with a competitor, reporter activation becomes dependent on the ability of the test antibody to compete with the competitor, which is proportional to the affinity of the test antibody for the antigen. Other reporter systems that can be used include the reactivator of an auto-inhibited reporter reactivation system (RAIR) as disclosed in U.S. patent application Ser. No. 10/208,730 (Publication No. 20030198971), or competitive activation system disclosed in U.S. patent application Ser. No. 10/076,845 (Publication No. 20030157579).

With the serial epitope-guided complementarity replacement system, selection is made to identify cells expresses a single test antibody along with the competitor, antigen, and reporter components. In these cells, each test antibody competes one-on-one with the competitor for binding to a limiting amount of antigen. Activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of "hybrid" antibodies, each of which is comprised of the same non-human V-region from the reference antibody and a human V-region from the library, and each of which binds to the same epitope on the antigen as the reference antibody. One of more of the hybrid antibodies selected in the first round will have an affinity for the antigen comparable to or higher than that of the reference antibody.

In the second V-region replacement step, the human V-regions selected in the first step are used as guide for the selection of human replacements for the remaining non-human reference antibody V-region with a diverse library of cognate human V-regions. The hybrid antibodies selected in the first round may also be used as competitors for the second round of selection. The result of the second round of selection is a set of fully human antibodies which differ structurally from the reference antibody, but which compete with the reference antibody for binding to the same antigen. Some of the selected human antibodies bind to the same epitope on the same antigen as the reference antibody. Among these selected human antibodies, one or more binds to the same epitope with an affinity which is comparable to or higher than that of the reference antibody.

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody." See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies and antigen-binding fragments thereof of non-human origin, an amino acid sequence of a camelid antibody can be altered recombinantly to obtain a sequence that more closely resembles a human sequence, i.e., the nanobody can be "humanized." Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for TSLP. In one embodiment herein, the camelid antibody or nanobody is naturally produced in the camelid animal, i.e., is produced by the camelid following immunization with TSLP or a peptide fragment thereof, using techniques described herein for other antibodies. Alternatively, the TSLP-binding camelid nanobody is engineered, i.e., produced by selection for example from a library of phage displaying appropriately mutagenized camelid nanobody proteins using panning procedures with TSLP as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising an TSLP-binding antibody, or a fragment thereof, of the invention. An antibody of the invention, or antigen-binding fragments thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for TSLP and a second binding specificity for a second target epitope. For example, the second target epitope may be another epitope of TSLP different from the first target epitope. In other embodiments, the second target epitope may to a target unrelated to TSLP, but which provides therapeutic benefit in combination with TSLP.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., an Fab, Fab', F (ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poijak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45 (3-4):128-30; Wu et al., 1996 Immunotechnology, 2 (1):21-36). scDb can be expressed in bacteria in soluble, active monomeric form (see Holliger and Winter, 1997 Cancer Immunol. Immunother., 45 (34): 128-30; Wu et al., 1996 Immunotechnology, 2 (1):21-36; Pluckthun and Pack, 1997 Immunotechnology, 3 (2): 83-105; Ridgway et al., 1996 Protein Eng., 9 (7):617-21). A diabody can be fused to Fc to generate a "di-diabody" (see Lu et al., 2004 J. Biol. Chem., 279 (4):2856-65).

Other antibodies which can be employed in the bispecific molecules of the invention are murine, chimeric and humanized monoclonal antibodies.

The bispecific molecules of the present invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F (ab')2 or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies and antigen-binding fragments thereof of the invention binding to TSLP. The antigen-binding portions can be linked together via protein fusion or covalent or non covalent linkage. Alternatively, methods of linkage has been described for the bispecific molecules. Tetravalent compounds can be obtained for example by cross-linking antibodies and antigen-binding fragments thereof of the invention with an antibody or antigen-binding fragment that binds to the constant regions of the antibodies and antigen-binding fragments thereof of the invention, for example the Fc or hinge region.

Trimerizing domain are described for example in Borean Pharma's patent EP 1 012 280B1. Pentamerizing modules are described for example in PCT/EP97/05897.

Antibodies with Extended Half Life

The present invention provides for antibodies that specifically bind to TSLP and have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half life of the antibodies and antigen-binding fragments thereof of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nancarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, antigen-binding fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10)alkoxy- or aryloxy-polyethylene glycol or polyethylene glycol-maleimide. In one embodiment, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies and antigen-binding fragments thereof of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622.

The strategies for increasing half life is especially useful in nanobodies, fibronectin-based binders, and other antibodies or proteins for which increased in vivo half life is desired.

Antibody Conjugates

The present invention provides antibodies or antigen-binding fragments thereof that specifically bind to the extrcellular domain of TSLP recombinantly fused or chemically conjugated (including both covalent and non-covalent conjugations) to a heterologous protein or polypeptide (or antigen-binding fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F (ab)$_2$ fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies and antigen-binding fragments thereof of the invention (e.g., antibodies and antigen-binding fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16 (2):76-82; Hansson, et al., 1999, J. Mol. Biol. 287:265-76; and Lorenzo and Blasco, 1998, Biotechniques 24 (2):308-313 (each of these patents and publications are hereby incorporated by reference in its entirety). Antibodies and antigen-binding fragments thereof, or the encoded antibodies and antigen-binding fragments thereof, may be altered by being subjected to random mutagenesis by error-prone PCR, random nucleotide insertion or other methods prior to recombination. A polynucleotide encoding an antibody antigen-binding fragment thereof that specifically binds to the stalk region of TSLP may be recombined with one or more components, motifs, sections, parts, domains, fragments, etc. of one or more heterologous molecules.

Moreover, the antibodies and antigen-binding fragments thereof can be fused to marker sequences, such as a peptide to facilitate purification. In one embodiment, the marker amino acid sequence is a hexa-histidine peptide (SEQ ID NO: 40), such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine (SEQ ID NO: 40) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

In one embodiment, antibodies and antigen-binding fragments thereof of the present invention antigen-binding fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149 Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and nonradioactive paramagnetic metal ions.

Further, an antibody antigen-binding fragment thereof may be conjugated to a therapeutic moiety or drug moiety. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, alpha-interferon, beta-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alpha-emitters such as 213Bi or macrocyclic chelators useful for conjugating radiometal ions, including but not limited to, 131In, 131LU, 131Y, 131Ho, 131Sm, to polypeptides. In one embodiment, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4 (10):2483-90; Peterson et al., 1999, Bioconjug. Chem. 10 (4):553-7; and Zimmerman et al., 1999, Nucl. Med. Biol. 26 (8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Nucleic Acids Encoding the Antibodies

The invention provides substantially purified nucleic acid molecules encoding polypeptides comprising segments or domains of the TSLP antibodies described above. Such polynucleotides can encode at least one CDR region and usually all three CDR regions from the heavy or light chain of the TSLP antibodies described herein. Such polynucleotides can also encode all or substantially all of the variable region sequence of the heavy chain and/or the light chain of the TSLP antibodies described herein. Such polynucleotides can also encode both a variable region and a constant region of the antibody. Because of the degeneracy of the code, a variety of nucleic acid sequences will encode each of the immunoglobulin amino acid sequences.

The polynucleotide sequences can be produced by de novo solid-phase DNA synthesis or by PCR mutagenesis of an existing sequence (e.g., sequences as described in the Examples below) encoding an TSLP-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Manila et al., Nucleic Acids Res. 19:967, 1991; and Eckert et al., PCR Methods and Applications 1:17, 1991.

Also provided in the invention are expression vectors and host cells for producing the TSLP-binding antibodies described above. Various expression vectors can be employed to express the polynucleotides encoding the TSLP-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the TSLP-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an TSLP-binding antibody chain antigen-binding fragment. In one embodiment, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a TSLP-binding antibody chain or antigen-binding fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted TSLP-binding antibody sequences. More often, the inserted TSLP-binding antibody sequences are linked to a signal sequences before inclusion in the vector. Vectors to be used to receive sequences encoding TSLP-binding antibody light and heavy chain variable domains sometimes also encode constant regions or parts thereof. Such vectors allow expression of the variable regions as fusion proteins with the constant regions thereby leading to production of intact antibodies and antigen-binding fragments thereof. Typically, such constant regions are human.

The host cells for harboring and expressing the TSLP-binding antibody chains can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express TSLP-binding polypeptides of the invention. Insect cells in combination with baculovirus vectors can also be used.

In one embodiment, mammalian host cells are used to express and produce the TSLP-binding polypeptides of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express TSLP-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Generation of Antibodies and Antibody Fragments

Monoclonal antibodies (mAbs) can be produced by a variety of techniques, including conventional monoclonal antibody methodology, e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

In some embodiments, the antibodies of the invention are humanized monoclonal antibodies. Chimeric or humanized antibodies and antigen-binding fragments thereof of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In some embodiments, the antibodies of the invention are human monoclonal antibodies. Such human monoclonal antibodies directed against TSLP can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (mu and gamma) and kappa light chain immunoglobulin sequences, together with targeted mutations that inactivate the endogenous mu and kappa chain loci (see e.g., Lonberg, et al., 1994 Nature 368 (6474): 856-859). Accordingly, the mice exhibit reduced expression of mouse IgM or K, and in response to immunization, the introduced human heavy and light chain transgenes undergo class switching and somatic mutation to generate high affinity human IgG-kappa monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569, 825; 5,625,126; 5,633,425; 5,789,650; 5,877,397; 5,661, 016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In some embodiments, human antibodies can be raised using a mouse that carries human immunoglobulin sequences on transgenes and transchomosomes such as a mouse that carries a human heavy chain transgene and a human light chain transchromosome. Such mice, referred to herein as "KM mice," are described in detail in PCT Publication WO 02/43478 to Ishida et al.

Still further, alternative transgenic animal systems expressing human immunoglobulin genes are available in the art and can be used to raise TSLP-binding antibodies and antigen-binding fragments thereof. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise TSLP-binding antibodies of the invention. For example, mice carrying both a human heavy chain transchromosome and a human light chain transchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise TSLP-binding antibodies of the invention.

Human monoclonal antibodies can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and U.S. Pat. No. 5,571,698 to Ladner et al; U.S. Pat. Nos. 5,427,908 and 5,580,717 to Dower et al; U.S. Pat. Nos. 5,969,108 and 6,172,197 to McCafferty et al; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Antibody Fab fragments, or Fabs, can be generated by digesting monoclonal antibodies with papain and then purified by affinity chromatography. Fabs can also be generated by recombinantly synthesized using the nucleic acids encoding the Fab as described above. Fab fragments can retain the binding specificity and/or activity of a full IgG molecule, but have are smaller in size and have lower molecular weights, which may make them suitable for different applications than full IgG molecules.

Framework or Fe Engineering

Engineered antibodies and antigen-binding fragments thereof of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Can et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In one embodiment, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fc-gamma receptor by modifying one or more amino acids. This approach is described further in PCT Publication WO 00/42072 by Presta. Moreover, the binding sites on human IgG1 for Fc-gamma RI, Fc-gamma RII, Fc-gamma Rill and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyltransferases (e.g., beta (1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the TSLP-binding antibodies having VH and VL sequences or full length heavy and light chain sequences shown herein can be used to create new TSLP-binding antibodies by modifying full length heavy chain and/or light chain sequences, VH and/or VL sequences, or the constant region (s) attached thereto. Thus, in another aspect of the invention, the structural features of TSLP-binding antibody of the invention are used to create structurally related TSLP-binding antibodies that retain at least one functional property of the antibodies and antigen-binding fragments thereof of the invention, such as binding to human TSLP.

For example, one or more CDR regions of the antibodies and antigen-binding fragments thereof of the present invention, or mutations thereof, can be combined recombinantly with known framework regions and/or other CDRs to create additional, recombinantly-engineered, TSLP-binding antibodies and antigen-binding fragments thereof of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence (s) is used as the starting material to create a "second generation" sequence (s) derived from the original sequence (s) and then the "second generation" sequence (s) is prepared and expressed as a protein.

The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence (s) is one that retains one, some or all of the functional properties of the TSLP-binding antibodies described herein, which functional properties include, but are not limited to, specifically binding to and stabilize human TSLP protein.

The functional properties of the altered antibodies can be assessed using standard assays available in the art and/or described herein, such as those set forth in the Examples (e.g., ELISAs).

In some embodiments, the methods of engineering antibodies and antigen-binding fragments thereof of the invention, mutations can be introduced randomly or selectively along all or part of an TSLP-binding antibody coding sequence and the resulting modified TSLP-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Characterization of the Antibodies of the Invention

The antibodies and antigen-binding fragments thereof of the invention can be characterized by various functional assays. For example, they can be characterized by their ability to bind TSLP and inhibit TSLP activity.

The ability of an antibody to bind to TSLP can be detected by labelling the antibody of interest directly, or the antibody may be unlabeled and binding detected indirectly using various sandwich assay formats known in the art.

In some embodiments, the TSLP-binding antibodies and antigen-binding fragments thereof of the invention block or compete with binding of a reference TSLP-binding antibody to TSLP polypeptide. These can be fully human or humanized TSLP-binding antibodies described above. They can also be other human, mouse, chimeric or humanized TSLP-binding antibodies which bind to the same epitope as the reference antibody. The capacity to block or compete with the reference antibody binding indicates that TSLP-binding antibody under test binds to the same or similar epitope as that defined by the reference antibody, or to an epitope which is sufficiently proximal to the epitope bound by the reference TSLP-binding antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen, such as TSLP polypeptide. A test antibody competes with the reference antibody for specific binding to the antigen if an excess of the test antibody substantially inhibits binding of the reference antibody. Substantial inhibition means that the test antibody reduces specific binding of the reference antibody usually by at least 10%, 25%, 50%, 75%, or 90%.

There are a number of known competition binding assays that can be used to assess competition of an antibody with a reference antibody for binding to a particular protein, in this case, TSLP. These include, e.g., solid phase direct or indirect radioimmunoassay (RIA), solid phase direct or indirect enzyme immunoassay (EIA), sandwich competition assay (see Stahli et al., Methods in Enzymology 9:242-253, 1983); solid phase direct biotin-avidin EIA (see Kirkland et al., J. Immunol. 137:3614-3619, 1986); solid phase direct labeled assay, solid phase direct labeled sandwich assay (see Harlow & Lane, supra); solid phase direct label RIA using I-125 label (see Morel et al., Molec. Immunol. 25:7-15, 1988); solid phase direct biotin-avidin EIA (Cheung et al., Virology 176:546-552, 1990); and direct labeled RIA (Moldenhauer et al., Scand. J. Immunol. 32:77-82, 1990). Typically, such an assay involves the use of purified antigen bound to a solid surface or cells bearing either of these, an unlabelled test TSLP-binding antibody and a labelled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if the selected TSLP-binding monoclonal antibodies bind to unique epitopes, each antibody can be biotinylated using commercially available reagents (e.g., reagents from Pierce, Rockford, Ill.). Competition studies using unlabeled monoclonal antibodies and biotinylated monoclonal antibodies can be performed using TSLP polypeptide coated-ELISA plates. Biotinylated MAb binding can be detected with a strep-avidin-alkaline phosphatase probe. To determine the isotype of a purified TSLP-binding antibody, isotype ELISAs can be performed. For example, wells of microtiter plates can be coated with 1 µg/ml of anti-human IgG overnight at 4 degrees C. After blocking with 1% BSA, the plates are reacted with 1 µg/ml or less of the monoclonal TSLP-binding antibody or purified isotype controls, at ambient temperature for one to two hours. The wells can then be reacted with either human IgG1 or human IgM-specific alkaline phosphatase-conjugated probes. Plates are then developed and analyzed so that the isotype of the purified antibody can be determined.

To demonstrate binding of monoclonal TSLP-binding antibodies to live cells expressing TSLP polypeptide, flow cytometry can be used. Briefly, cell lines expressing TSLP (grown under standard growth conditions) can be mixed with various concentrations of TSLP-binding antibody in PBS containing 0.1% BSA and 10% fetal calf serum, and incubated at 37 degrees ° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

TSLP-binding antibodies and antigen-binding fragments thereof of the invention can be further tested for reactivity with TSLP polypeptide or antigenic fragment by Western blotting. Briefly, purified TSLP polypeptides or fusion proteins, or cell extracts from cells expressing TSLP can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Examples of functional assays are also described in the Example section below.

Pharmaceutical Compositions and Formulation

Also provided herein are compositions, e.g., pharmaceutical compositions, comprising one or more molecules, e.g., antibodies, antibody fragments such as Fab, Fab', F(ab')2, scFv, minibody, or diabody, that specifically bind TSLP, as the active ingredient.

Pharmaceutical compositions typically include a pharmaceutically acceptable excipient. A pharmaceutically acceptable excipient can includes saline, solvents, dispersion media, coatings, antibacterial and antifungal agents, isotonic and absorption delaying agents, and the like, compatible with pharmaceutical administration. Pharmaceutical compositions are typically formulated to be compatible with its intended route of administration. For example, for administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

In some embodiments, the pharmaceutical compositions provided herein are formulated for targeted delivery to the respiratory tract of a subject, especially the lung of the subject. Such formulation can bypass deposition of the active ingredient in the upper respiratory tract of the subject, thereby minimizing tolerability or safety issues associated with drug deposition in the mouth and throat. In some embodiments, the pharmaceutical compositions provided herein are formulated as a dry powder formulation. Such dry powder formulation can include the active ingredient, a shell-forming excipient, a glass-forming excipient, and a buffer.

Active Ingredient

The active ingredients of the dry powder formulations can include one or more of the anti-TSLP antibodies and antibody fragments as described herein.

The amount of active ingredient in the pharmaceutical formulation can be adjusted to deliver a therapeutically effective amount of the active ingredient per unit dose to achieve the desired result. In practice, this will vary widely depending upon the particular ingredient, its activity, the severity of the condition to be treated, the patient population, dosing requirements, the desired therapeutic effect and the relative amounts of additives contained in the composition. The composition will generally contain anywhere from about 1% by weight to about 99% by weight of the active ingredient, e.g., about 5% to about 95%, about 10% to about 90%, about 15% to 85%, about 20% to 80%, about 25% to 75%, about 30% to 70%, about 40% to 60%, or about 50% by weight of the active ingredient. The compositions of the invention are particularly useful for active ingredients that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active ingredient may be incorporated into the formulations described herein and that the use of the term "active ingredient" in no way excludes the use of two or more such active ingredients.

Excipients

In some embodiments, the dry powder formulation described herein contains a pharmaceutically acceptable hydrophobic shell-forming excipient. Shell-forming excipients are surface active agents that enhance dispersibility of spray-dried powders. The hydrophobic shell-forming excipient may take various forms that will depend at least to some extent on the composition and intended use of the dry powder formulation. Suitable pharmaceutically acceptable hydrophobic excipients may, in general, be selected from the group consisting of long-chain phospholipids, hydrophobic amino acids and peptides, and long chain fatty acid soaps.

In some embodiments, shell-forming excipients include: glycine, alanine, valine, trileucine, dileucine, leucine, isoleucine, proline, phenylalanine, methionine, tryptophan, dipalmitoylphosphatidylcholine (DPPC), distearoylphosphatidylcholine (DSPC), and magnesium stearate. In some embodiments, the dry powder formulations described herein include trileucine.

By control of the formulation and process, it is possible for the surface of the spray-dried particles to be comprised primarily of the shell-forming excipient. Surface concentrations may be greater than 70%, such as greater than 75% or 80% or 85%. In some embodiments, the surface is comprised of greater than 90% shell-forming excipient, or greater than 95% or 98% or 99% hydrophobic excipient. For potent active ingredients, it is not uncommon for the surface to be comprised of more than 95% shell-forming excipient.

In some embodiments, the shell-forming excipient comprises greater than 70% of the particle interface as measured by Electron Spectroscopy for Chemical Analysis (ESCA, also known as X-ray photoelectron spectroscopy or XPS), preferably greater than 90% or 95%.

In some embodiments, the shell-forming excipient facilitates development of a rugous particle morphology. This means the particle morphology is porous, wrinkled, corrugated or creased rather than smooth. This means the interior and/or the exterior surface of the inhalable medicament particles are at least in part rugous. This rugosity is useful for providing high delivery efficiency, dose consistency and drug targeting by improving powder fluidization and dispersibility. Increases in particle rugosity result in decreases in inter-particle cohesive forces as a result of an inability of the particles to approach to within van der Waals contact. The decreases in cohesive forces are sufficient to dramatically improve powder fluidization and dispersion in ensembles of rugous particles.

If present, content of the shell-forming excipient generally ranges from about 15 to 50% w/w of the medicament. For trileucine, a minimum of about 15% is required in the formulation to provide acceptable performance as a shell-former. For leucine, the minimum required content is higher, about 30%.

The use of hydrophobic shell-forming excipients such as trileucine may be limited by their solubility in the liquid feedstock. Typically, the content of trileucine in an engineered powder is less than 30% w/w, more often on the order of 10% w/w to 20% w/w (about 10-30% w/w). Owing to its limited solubility in water and its surface activity, trileucine is an excellent shell former. Leucine may also be used as a shell forming excipient and embodiments of the invention may comprise particles comprising leucine concentrations of about 50% to 75%.

Fatty acid soaps behave similarly to leucine and trileucine and are thus suitable surface modifiers.

Due to the short timescale of the drying event, active ingredients that are dissolved in the feedstock will be generally present as amorphous solids in the spray-dried drug product.

The molecular mobility of an amorphous solid is significant when compared to that of its crystalline counterpart. Molecular mobility comprises long-range motions related to molecular diffusion as well as local motions such as bond rotations. The central principle in solid-state stabilization of amorphous materials is that molecular mobility leads to undesirable physical and chemical changes. Therefore, formulation strategies for amorphous materials usually focus on suppression of molecular mobility.

The existence of a relationship between molecular mobility and instability is intuitive and well-known. However, to be useful, molecular mobility must be carefully defined and understood in terms of the types of motions present. Long-range molecular motions arise from structural relaxation, known as α-relaxation. The timescale for such motions increases markedly as temperature decreases below the glass transition temperature (Tg), or conversely, as the Tg is raised at a fixed observation temperature. Because stabilization of a molecule in a glass limits its long-range molecular mobility, this has become the most common formulation strategy for solid-state stabilization of amorphous drugs.

Glassy stabilization control of molecular mobility in the solid state, such as through use of glass-forming agents, can improve the physicochemical stability of the protein in the formulation. When a glass-forming agent is needed, multiple considerations will govern its selection. The primary role of a glass-forming excipient is to reduce the overall long-range molecular mobility of the drug. In practice, this is accomplished by raising the glass transition temperature of the amorphous phase that contains the drug. While excipients with high Tg values are generally desirable, even an excipient with a moderate Tg could be suitable for some formulations (e.g., drugs with a moderate Tg or if the drug concentration in the formulation is low). To guide the formulator, it is worthwhile to highlight the properties of an ideal glass-former: a biocompatible material with a high glass transition temperature that is miscible with the drug, forming a single amorphous phase that is only weakly plasticized by water.

In some embodiments, the dry powder formulations described herein contain a glass-forming excipient. Glass-forming excipients that suppress long-range molecular mobility include carbohydrates, amino acids, and buffers. In some embodiments, glass-forming excipients include: histidine, histidine HCl, sucrose, trehalose, mannitol, and sodium citrate. Thus some excipients, such as histidine, may be referred to as a buffer or a glass-forming excipient interchangeably. In some embodiments, the dry powder formulations described herein, e.g., the core-shell formulations, include trehalose.

The importance of other types of molecular motions has become increasingly recognized in the pharmaceutical literature. The nomenclature (α, β, etc.) used to designate the types of molecular motions originates from broadband dielectric spectroscopy. Dielectric relaxation spectra are conventionally plotted on a frequency scale. When these spectra are interpreted, the dielectric loss peaks at the lowest frequencies are designated as a motions, the higher frequency motions as β motions, then γ, and so forth. Thus, β and other motions that occur at higher frequencies are referred to as "fast" or secondary motions (and, in some cases, Johari-Goldstein relaxations). Although these secondary relaxations are often ascribed to intramolecular motions of different molecular moieties (e.g., side chains on a protein), they exist even for rigid molecules. In a simplistic physical picture, the β motions are sometimes described as random "cage rattling" of a species trapped among its nearest neighbors. At some point, the local motions of the nearest neighbors provide sufficient free volume to enable a diffusive jump of the trapped species. This is an α motion. Thus, the β motions lead to α motions.

Secondary motions are an area of active research from both theoretical and practical perspectives. And, although much of the literature involves lyophilized or melt-quenched glasses, the principles are also relevant to amorphous, engineered particles for inhalation (e.g., powders manufactured using spray-drying or certain other bottom-up processes). Crystallization of small molecules near Tg has been suspected to arise from β motions. Protein formulators have recognized the importance of controlling these β motions. Suppression of β motions in amorphous formulations is typically done with small, organic excipients, such as glycerol, mannitol, sorbitol, and dimethylsulfoxide. Although these are the most frequently reported excipients to suppress β motions, other low MW organic molecules could serve this purpose (e.g., buffer salts or counterions). These excipients are hypothesized to suppress motions of high-mobility domains by raising the local viscosity. To the reader familiar with the vast literature on glassy stabilization, the use of such excipients might seem counterintuitive. These and most other low molecular weight materials have low Tg values and will reduce the Tg of a formulation, a phenomenon known as plasticization. However, these excipients can also diminish β motions. Thus, they are referred to as antiplasticizers or sometimes as plasticizers, depending on the point of reference; while they plasticize the α motions, they antiplasticize the β motions. Note that this terminology is a potential source of confusion in the literature; the designation of a material as a plasticizer or an antiplasticizer depends on whether one's point of reference is the α or the secondary motions.

Because solid-state stabilization of proteins requires formulation of a glassy matrix, the contributions of α and β motions are of particular interest. Although the literature has numerous references of using glass-forming agents to stabilize proteins, until recently, there have been few specific references to the influence of these agents on local motions. Although the glass transition temperatures of proteins are difficult to measure, most data suggest that Tg>150° C. Thus, the excipients (e.g., disaccharides such as sucrose or trehalose) most commonly used to stabilize proteins will also plasticize the α motions in the protein (and antiplasticize secondary motions). Recent work has demonstrated that β motions largely govern the stability of proteins in sugar glasses. Thus, disaccharides antiplasticize β motions in protein formulations.

In some embodiments, the dry powder formulations described herein comprise glass-forming excipients with a high glass transition temperature (>80° C.). In some embodiments, the dry powder formulations described herein comprise glass forming agents such as sucrose, trehalose, mannitol, fumaryl diketopiperazine, and sodium citrate.

Mixtures of glass-forming agents can be used to achieve optimal stabilization of the amorphous solid. For the 'platform' core-shell formulations, mixtures of trehalose and mannitol are used in some embodiments.

The amount of glass former required to achieve suppress molecular mobility and achieve physical and chemical stability will be dependent on the nature of the active agent. For some embodiments with spray-dried proteins, the molar ratio of glass former to protein may be in the range from 300 to 900. For small molecules, the required amount of glass former will depend on the Tg of the active agent.

In some embodiments, the dry powder formulations described herein contain a buffer. Buffers are well known for pH control, both as a means to deliver a drug at a physiologically compatible pH (i.e., to improve tolerability), as well as to provide solution conditions favorable for chemical stability of a drug. In some formulations and processes described herein, the pH milieu of a drug can be controlled by co-formulating the drug and buffer together in the same particle.

While it is natural to question the meaning of pH in a solid-state drug product, a number of studies have demonstrated the importance of pH control to solid-state chemical stability. Water is ubiquitous, even in "dry" powder formulations in the solid state. In addition to its role as a plasticizer of amorphous materials, water is a reactant, a degradation product, and can also serve as a medium for dissolution and chemical reactions. There is evidence that adsorption of water onto particle surfaces can result in a saturated solution within the surface film. Indeed, some studies have used the pH of a drug slurry (i.e., a saturated solution) as an indicator of the local or "microenvironmental" pH of the drug dissolved in the surface film in a "dry" powder. The microenvironmental pH has been shown, in some cases, to be relevant to the stability of the drug.

As with a drug, excipients also dissolve in the surface film of adsorbed water to form a saturated solution. This can be used to the formulator's advantage to enable control of the local pH in the adsorbed layer of moisture. Buffers or pH modifiers, such as histidine or phosphate, are commonly used in lyophilized or spray-dried formulations to control solution- and solid-state chemical degradation of proteins.

In some embodiments buffers for the formulation include: histidine, glycine, acetate, and phosphate.

Optional excipients include salts (e.g., sodium chloride, calcium chloride, sodium citrate), antioxidants (e.g., methionine), excipients to reduce protein aggregation in solution (e.g., arginine), taste-masking agents, and agents designed to improve the absorption of macromolecules into the systemic circulation (e.g., fumaryl diketopiperazine).

Formulation

Provided herein are dry powder formulations comprising spray-dried particles that effectively bypass deposition in the oropharynx of an average adult subject, enabling targeted delivery of medicament into the lungs.

In some embodiments, particles of the dry powder formulations described herein have an in vitro total lung dose (TLD) of between 80 and 95% w/w of the nominal dose, for example between 85 and 90% w/w for an average adult subject.

In some embodiments, particles of the dry powder formulations described herein have an in vitro total lung dose (TLD) of between 90 and 100% w/w of the delivered dose, for example between 90 and 95% w/w for an average adult subject.

In some embodiments, the dry powder formulations described herein comprise the delivered dose suitably having an inertial parameter of between 120 and 400 μm2 L/min, for example between 150 and 300 $\mu m^2$ L/min.

In some embodiments, the dry powder formulations described herein comprise engineered particles comprising a porous, corrugated, or rugous surface. Such particles exhibit reduced interparticle cohesive forces compared to micronized drug crystals of a comparable primary particle size. This leads to improvements in powder fluidization and dispersibility relative to ordered mixtures of micronized drug and coarse lactose.

In some embodiments, particles of the dry powder formulations described herein have a rugosity of greater than 1.5, for example from 1.5 to 20, 3 to 15, or 5 to 10.

For some active pharmaceutical ingredients, e.g., many peptides or proteins (e.g., anti-TSLP Fab), a rugous surface can be achieved via spray-drying of the neat drug. In such a case, the formulation may comprise neat drug, that is 100% w/w of active agent or drug.

In some embodiments, the dry powder formulations described herein comprise drug and buffer. The formulation may comprise 70% to 99% w/w of drug or active agent, and the remainder is buffer.

In some embodiments, the formulations described herein may comprise 0.1 to 99% w/w of active agent, or 0.1 to 70% w/w of active agent, or 0.1 to 50% w/w of active ingredient(s), or 0.1% to 30% w/w of active ingredient(s).

In some embodiments, the dry powder formulations described herein may include excipients to further enhance the stability or biocompatibility of the formulation.

For example, various salts, buffers, antioxidants, shell-forming excipients, and glass forming excipients are contemplated.

In some embodiments, particles of the dry powder formulations described herein have a geometric size, expressed as a mass median diameter (×50) of between 0.8 and 2.0 µm, for example of between 1.0 and 1.5 µm.

In some embodiments, particles of the dry powder formulations described herein have a geometric size, expressed as ×90 of between 2.0 µm and 4.0 µm, for example between 2.5 µm and 3.5 µm.

In some embodiments, particles of the dry powder formulations described herein have a tapped density (ptapped) of between 0.03 and 0.40 g/cm3, for example of between 0.07 and 0.30 g/cm3.

In some embodiments, the primary particles of the dry powder formulations described herein have a calculated median aerodynamic size (Da) of between 0.1 and 1.0 µm, for example between 0.5 and 0.8 µm.

In some embodiments, particles of the dry powder formulations described herein have a calculated aerodynamic diameter of between 0.5 and 1.2 µm, for example of between 0.8 and 1.0 µm.

In some embodiments, the ensemble of particles of the dry powder formulations described herein present in the delivered dose suitably have a mass median aerodynamic diameter (MMAD) of between 1.0 and 3.0 µm, for example of between 1.5 and 2.0 µm.

In some embodiments, the formulation of the present disclosure contains particles comprising a shell and a core: trileucine as a shell-former present at the particle surface, and a core comprising the active ingredient (e.g., anti-TSLP Fab), trehalose, or trehalose and mannitol in combination, and a buffer.

In some embodiments, the invention provides a formulation comprising about 40% (w/w) TSLP-binding molecule, e.g., anti-TSLP Fab1, about 25% (w/w) trileucine, about 30% (w/w) trehalose and mannitol combined, and about 5% (w/w) histidine. In other embodiments, the present application provides a formulation comprising about 50% (w/w) TSLP-binding molecule, about 15% (w/w) trileucine, about 2.6% (w/w) HCl, about 5.6% (w/w) histidine, and about 26.8% (w/w) trehalose and a base combined; or about 50% (w/w) TSLP-binding molecule, about 15% (w/w) trileucine, about 19.4% (w/w) trehalose, about 13% (w/w) histidine, and about 2.6% (w/w) HCl.

In further embodiments, the present application discloses a carrier-free pharmaceutical powder composition comprising particles deliverable from a dry powder inhaler, comprising the anti-TSLP molecules disclosed herein, wherein an in vitro total lung dose is greater than 90% of the delivered dose, and wherein the particles in the delivered dose have an inertial parameter between 120 and 400 µm² L/min.

In another embodiment, the present application discloses a carrier-free pharmaceutical composition deliverable from a dry powder inhaler, the composition comprising a plurality of particles, comprising a core comprising an anti-TSLP molecule as disclosed herein and at least one glass forming excipient, and a shell comprising hydrophobic excipient and a buffer; and wherein the in vitro total lung dose is greater than 90% w/w of the delivered dose. In some embodiments, the particles are formed by spray-drying. In another embodiment, the hydrophobic excipient comprises trileucine.

In a further embodiment, the present application discloses a carrier-free pharmaceutical composition comprising a plurality of primary particles and particle agglomerates deliverable from a dry powder inhaler, the composition comprising an anti-TSLP molecule as disclosed herein, and wherein an in vitro total lung dose (TLD) is greater than 80% of a nominal dose, and wherein the primary particles are characterized by: a corrugated morphology; a median aerodynamic diameter (Da) between 0.3 and 1.0 µm; and wherein the particles and particle agglomerates delivered from a dry powder inhaler have a mass median aerodynamic diameter (MMAD) between 1.5 and 3.0 µm. In some embodiments, the pharmaceutical composition further comprises a receptacle for containing the primary particles, the receptacle suitable for containing the particles prior to their aerosolization within a dry powder inhaler, and wherein the aerosol comprising respirable agglomerates is formed upon said aerosolization.

In a further embodiment, the present application discloses a pharmaceutical powder formulation for pulmonary delivery, the powder comprising particles comprising: 1 to 100 wt % of an anti-TSLP molecule as disclosed herein, wherein the powder is characterized by a particle size distribution of at least 50% between 1 to 1.5 microns, a or powder density of 0.05 to 0.3 g/cm3, an aerodynamic diameter of less than 2 microns, a rugosity of 1.5 to 20; and wherein the powder is administered by inhalation, and provides an in vitro total lung dose of greater than 80%. In some embodiments, the pharmaceutical powder formulation is carrier-free. In other embodiments, the powder is packaged in a receptacle for use with a dry powder inhaler, and wherein when aerosolized using said dry powder inhaler, the powder is characterized by respirable agglomerates having a mass median aerodynamic diameter of less than about 2 microns.

Process

Provided herein are also process for preparing dry powder formulations for inhalation comprising spray-dried particles, the formulation containing at least one active ingredient, and having an in vitro total lung dose (TLD) of between 80 and 95% w/w, for example between 85 and 90% w/w of the nominal dose for an average adult subject.

Provided herein are also processes for preparing dry powder formulations for inhalation comprising spray-dried particles, the formulation containing at least one active ingredient, and having an in vitro total lung dose (TLD) of between 90 and 100% w/w, for example between 90 and 95% w/w of the delivered dose for an average adult subject.

In some embodiments, the dry powder formulations contain at least one active ingredient that is suitable for treating obstructive or inflammatory airways diseases, particularly asthma and/or COPD, e.g., anti-TSLP Fabs. In some embodiments, the dry powder formulations contain at least one active ingredient that is suitable for non-invasively treating diseases in the systemic circulation.

Spray drying confers advantages in producing engineered particles for inhalation such as the ability to rapidly produce a dry powder, and control of particle attributes including size, morphology, density, and surface composition. The drying process is very rapid (on the order of milliseconds). As a result most active ingredients which are dissolved in the liquid phase precipitate as amorphous solids, as they do not have sufficient time to crystallize.

Spray-drying comprises four unit operations: feedstock preparation, atomization of the feedstock to produce micron-sized droplets, drying of the droplets in a hot gas, and collection of the dried particles with a bag-house or cyclone separator.

In some embodiments, the processes for making dry powder particles comprise three steps, however in some embodiments two or even all three of these steps can be carried out substantially simultaneously, so in practice the process can in fact be considered as a single step process. Solely for the purposes of describing the process of the present invention the three steps will be described separately, but such description is not intended to limit to a three step process.

In some embodiments, the process includes preparing a solution feedstock and spray-drying the feedstock to provide active dry powder particles. The feedstock comprises at least one active ingredient dissolved in an aqueous-based liquid feedstock. In some embodiments, the feedstock comprises at least one active ingredient (e.g., anti-TSLP Fab1) dissolved in an aqueous-based feedstock comprising an added co-solvent. In some embodiments, the feedstock comprises at least one active agent dissolved in an ethanol/water feedstock, wherein the fraction of ethanol is between 5% and 30% w/w, for example between 5% and 20% w/w.

For amorphous solids, it is important to control the moisture content of the drug product. For drugs which are not hydrates, the moisture content in the powder is preferably less than 5%, more typically less than 3%, or even 2% w/w. Moisture content must be high enough, however, to ensure that the powder does not exhibit significant electrostatic attractive forces. The moisture content in the spray-dried powders may be determined by Karl Fischer titrimetry.

In some embodiments, the feedstock is sprayed into a current of warm filtered air that evaporates the solvent and conveys the dried product to a collector. The spent air is then exhausted with the solvent. Operating conditions of the spray-dryer such as inlet and outlet temperature, feed rate, atomization pressure, flow rate of the drying air, and nozzle configuration can be adjusted in order to produce the required particle size, moisture content, and production yield of the resulting dry particles. The selection of appropriate apparatus and processing conditions are within the purview of a skilled artisan in view of the teachings herein and may be accomplished without undue experimentation. Exemplary settings for a NIRO® PSD-1® scale dryer are as follows: an air inlet temperature between about 80° C. and about 200° C., such as between 110° C. and 170° C.; an air outlet between about 40° C. to about 120° C., such as about 60° C. and 100° C.; a liquid feed rate between about 30 g/min to about 120 g/min, such as about 50 g/min to 100 g/min; total air flow of about 140 standard cubic feet per minute (scfm) to about 230 scfm, such as about 160 scfm to 210 scfm; and an atomization air flow rate between about 30 scfm and about 90 scfm, such as about 40 scfm to 80 scfm. The solids content in the spray-drying feedstock will typically be in the range from 0.5% w/v (5 mg/ml) to 10% w/v (100 mg/ml), such as 1.0% w/v to 5.0% w/v. The settings will, of course, vary depending on the scale and type of equipment used, and the nature of the solvent system employed. In any event, the use of these and similar methods allow formation of particles with diameters appropriate for aerosol deposition into the lung.

In some embodiments, the excipients are all dissolved in the feedstock, and core-shell coatings on the dispersed active ingredient are driven by differences in the physical properties of the dissolved solutes.

As discussed previously for the particles comprising an amorphous active ingredient, the nature of the particle surface and morphology will be controlled by controlling the solubility and diffusivity of the components within the feedstock. Surface active hydrophobic excipients (e.g., trileucine, phospholipids, fatty acid soaps) may be concentrated at the interface, improving powder fluidization and dispersibility, while also driving increased surface roughness for the particles.

Any spray-drying step and/or all of the spray-drying steps may be carried out using conventional equipment used to prepare spray dried particles for use in pharmaceuticals that are administered by inhalation. Commercially available spray-dryers include those manufactured by Büchi Ltd. and Niro Corp.

In some embodiments, the feedstock is atomized with a twin fluid nozzle. Significant broadening of the particle size distribution of the liquid droplets occurs above solids loading of about 1.5% w/w. The larger sized droplets in the tail of the distribution result in larger particles in the corresponding powder distribution. As a result, some embodiments with twin fluid nozzles restrict the solids loading to 1.5% w/w or less, such as 1.0% w/w, or 0.75% w/w.

In some embodiments, narrow droplet size distributions can be achieved with plane film atomizers as disclosed, for example, in U.S. Pat. Nos. 7,967,221 and 8,616,464 at higher solids loadings. In some embodiments, the feedstock is atomized at solids loading between 2% and 10% w/w, such as 3% and 5% w/w.

In some embodiments the particle population density or PPD is between $0.01 \times 10^{-6}$ and $1.0 \times 10^{-6}$, such as between $0.03 \times 10^{-6}$ and $0.2 \times 10^{-6}$.

In some embodiments, the EtOH/solids ratio is between 1.0 and 20.0, such as between 3.0 and 10.0.

In some embodiments, the present application discloses a pharmaceutical powder formulation for inhalation comprising particles made by a process comprising:
  a. preparing a solution of the anti-TSLP binding molecules disclosed herein in a water/ethanol mixture, wherein the ethanol is present between 1 and 20% and a ratio of ethanol to total solids is between 1 and 20;
  b. spray drying the solution to obtain particulates, wherein the particulates are characterized by a particle density of 0.2 g/cm3 or lower, a geometric diameter of 1-3 microns and an aerodynamic diameter of 1 to 2 microns;

and wherein the powder, when administered by inhalation, provides in vitro total lung dose greater than about 80%. In some embodiments, the pharmaceutical powder formulation further includes a glass-forming excipient. In some embodiments, the glass-forming excipient comprises an alpha. In other embodiments, the glass-forming excipient comprises a beta. In a further embodiment, the glass-forming excipient comprises trehalose.

In some embodiments of the pharmaceutical powder formulation, the particle population density is between $0.01 \times 10^{-6}$ and $1.0 \times 10^{-6}$.

The present application also discloses a method of delivering to the lungs of a subject particles comprising a dry powder, the method comprising:
  a. preparing a solution of the anti-TSLP binding molecules disclosed herein in a water/ethanol mixture, wherein the ethanol is present between 5 and 20%,
  b. spray drying the solution to obtain particulates, wherein the particulates are characterized by a particle density of between about 0.05 and 0.3 g/cm3 a geometric diameter of 1-3 microns and an aerodynamic diameter of 1-2 microns;
  c. packaging the spray-dried powder in a receptacle;
  d. providing an inhaler having a means for extracting the powder for the receptacle, the inhaler further having a powder fluidization and aerosolization means, the inhaler operable over a patient-driven inspiratory effort of about 2 to about 6 kPa; the inhaler and powder together providing an inertial parameter of between about between 120 and 400 µm2 L/min and wherein the powder, when administered by inhalation, provides at least 90% lung deposition.

The present application also discloses a method of preparing a dry powder medicament formulation for pulmonary delivery, the method comprising
  a. preparing a solution of the anti-TSLP binding molecules disclosed herein in a water/ethanol mixture, wherein the ethanol is present between 5 and 20%,
  b. spray drying the solution to obtain particulates, wherein the particulates are characterized by a particle density of between about 0.05 and 0.3, a geometric diameter of 1-3 microns and an aerodynamic diameter of 1-2 microns.

In a further embodiment, the present application discloses a powder pharmaceutical composition deliverable from a dry powder inhaler, comprising particles comprising the anti-TSLP binding molecules disclosed herein, wherein an in vitro total lung dose is greater than 90% w/w of the delivered dose, and wherein the composition comprises at least one characteristic of being carrier-free, a particle density of 0.05 to 0.3 g/cm3; a particle rugosity of 3 to 20; particles made by a process comprising spray drying from an ethanol:water mixture; and particles made by a process comprising spray drying from an ethanol:water mixture having an ethanol:solids ratio of between 1 and 20. In some embodiments, the powder pharmaceutical composition comprises at least two of the characteristics; in other embodiments, the powder pharmaceutical composition comprises at least three of the characteristics.

Dosage

Dosage, toxicity, and therapeutic efficacy of the anti-TSLP molecules disclosed herein, including pharmaceutical compositions comprising anti-TSLP antibodies or fragments thereof, can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are desired. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Kits

Also provided herein are kits including one or more of the pharmaceutical compositions provided herein, a device for delivering the pharmaceutical composition to a subject, and instructions for use. In some embodiments, the device can deliver the pharmaceutical composition in an aerosolized form. In some embodiments, the device is an inhaler, e.g., a dry powder inhaler (DPI). In other embodiments, the device may be a metered dose inhaler or a nebulizer.

Suitable dry powder inhalers include unit dose inhalers, where the dry powder is stored in a capsule or blister, and the patient loads one or more of the capsules or blisters into the device prior to use. Alternatively, multi-dose dry powder inhalers are contemplated where the dose is pre-packaged in foil-foil blisters, for example in a cartridge, strip or wheel.

Dry powder inhalers include multi-dose dry powder inhalers such as the DISKUS™ (GSK, described in U.S. Pat. No. 6,536,427), DISKHALER™ (GSK, described in Patent Application Publication WO 97/25086), GEMINI™ (GSK, described in Patent Application Publication WO 05/14089), GYROHALER™ (Vectura, described in Patent Application Publication WO 05/37353), and PROHALER™ (Valois, described in Patent Application Publication WO 03/77979).

Single dose dry powder inhalers include the AEROLIZER™ (Novartis, described in U.S. Pat. No. 3,991,761) and BREEZHALER™ (Novartis, described in U.S. Pat. No. 8,479,730 (Ziegler et al.). Other suitable single-dose inhalers include those described in U.S. Pat. Nos. 8,069,851 and 7,559,325.

Unit dose blister inhalers, which some patients find easier and more convenient to use to deliver medicaments requiring once daily administration, include the inhaler described by in U.S. Pat. No. 8,573,197 (Axford et al.).

In some embodiments, the inhalers are multi-dose dry powder inhalers where the energy for fluidizing and dispersing the powder is supplied by the patient (i.e., "passive" MD-DPIs). The powders of the present invention fluidize and disperse effectively at low peak inspiratory flow rates (PIF). As a result, the small changes in powder dispersion with PIF observed effectively balance the increases in inertial impaction which occur with increases in PIF, leading to flow rate independent lung deposition. The absence of flow rate dependence observed for powders of the present invention drives reductions in overall interpatient variability.

Instructions for use can include instructions for diagnosis or treatment of TSLP-related inflammatory conditions. Kits as provided herein can be used in accordance with any of the methods described herein. Those skilled in the art will be aware of other suitable uses for kits provided herein, and will be able to employ the kits for such uses. Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

Methods of Treatment

Provided herein are methods of treating a TSLP-related condition in a subject in need of treatment thereof, e.g., a human, by administering to the subject a therapeutically effective amount of any of the TSLP-binding molecules described herein, or pharmaceutical compositions thereof. In some embodiments, such methods further include identifying and selecting a subject in need of treatment of a TSLP-related inflammatory condition. The invention also provides use of the TSLP-binding molecules as described herein, or pharmaceutical compositions thereof, to treat or prevent disease in a patient. In some embodiments, the invention provides TSLP-binding molecules as described herein, or pharmaceutical compositions thereof, for use in the treatment or prevention of disease in a patient. In further embodiments, the invention provides use of the TSLP-binding molecules as described herein or pharmaceutical compositions thereof, in the manufacture of a medicament for use in treatment or prevention of disease in a patient.

In some embodiments, the TSLP-related inflammatory conditions may be triggered by allergic reactions or environmental irritants or stimulants. In some specific embodiments, the TSLP-related inflammatory conditions include asthma, chronic obstructive pulmonary disease, allergic rhinitis, allergic rhinosinusitis, allergic conjunctivitis, atopic dermatitis, eosinophilic esophagitis.

In some embodiments, the TSLP-binding molecules, or pharmaceutical compositions comprising the TSLP-binding molecules are administered to the subject by inhalation, e.g., in an aerosolized form by a dry powder inhaler. In other embodiments, the TSLP-binding molecules or pharmaceutical compositions may be administered using one or more of a variety of methods known in the art. As will be appreciated by the skilled artisan, the route and/or mode of administration will vary depending upon the desired results. Selected routes of administration include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the TSLP-binding molecules, or pharmaceutical compositions comprising the TSLP-binding molecules of the invention, can be administered via a non-parenteral route, such as a topical, epidermal or mucosal route of administration, for example, intranasally, orally, vaginally, rectally, sublingually or topically.

In some embodiments, the TSLP-related inflammatory condition is asthma. Asthma is a complex and heterogeneous chronic inflammatory disease of the airways that is characterized by reversible bronchoconstriction and associated with an exaggerated response of the airways to a wide range of bronchoconstrictor stimuli (airway hyperresponsiveness; AHR). Recent work has focused on identifying immune pathways involved in asthma pathogenesis, and has revealed roles for both T helper type 2 (Th2) and non-Th2 mediated effector cells (Lambrecht and Hammad, Nature immunology 2014, 16: 45-56). In the case of allergic asthma, characterized by eosinophilic inflammation and evidence of atopy, Th2 immune pathway elements are crucial in the development and maintenance of airway inflammation and AHR. Thymic stromal lymphopoietin (TSLP) is a key upstream regulator of the Th2 response. TSLP is expressed in mucosal epithelial cells within the airway in response to diverse stimuli (e.g., physical injury, ambient particulate matter, allergens, pro-inflammatory or Th2-polarizing cytokines, and microbial products). The role of TSLP is to modulate dendritic cells (DC) and induce the differentiation of naive T cells into inflammatory Th2 cells and to promote cytokine secretion from mast cells, eosinophils and macrophages as a part of the innate immune response. In addition, TSLP can interfere with regulatory T cell development impairing the balance between tolerance and inflammation. In the case of non-allergic asthma, characterized by neutrophilic or paucigranulocytic inflammation, the cytokines driving inflammation are not as well understood, however the non-Th2 mediated cytokines IL-17 and interferon-y (IFN-γ) are both believed to play a role. Interestingly, in addition to its role in mediating the Th2 response, preclinical evidence suggests that TSLP amplifies non-Th2 responses and may also be important in establishing IL-17 and IFN-y mediated chronic inflammation.

TSLP is both necessary and sufficient for the development of Th2 cytokine-associated inflammation of the airways in rodents. Transgenic mice with constitutive lung epithelial secretion of TSLP, under the control of the surfactant protein C promoter, developed the following features compatible with asthma: eosinophilic airway inflammation; expression of Th2 biased CD4 T cell infiltration; systemic eosinophilia; increased IgE; airway hyper-responsiveness; and significant airway remodeling including goblet cell hyperplasia and airway and vascular fibrosis. Further supporting the role of TSLP in allergic inflammation, TSLP expression and protein production is also found to increase upon inhaled allergen exposure in the lung (Zhou et al., 2005, Nature immunology 6, 1047-1053), whereas direct intranasal delivery of TSLP in the presence of antigen leads to rapid onset of severe disease (Headley et al., 2009, Journal of immunology 182, 1641-1647). TSLPR-deficient mice are resistant to the development of Th2-like inflammation in the classical ovalbumin-plus-alum priming model in mice (Al-Shami et al., 2005, The Journal of experimental medicine 202, 829-839; Zhou et al., 2005, Nature immunology 6, 1047-1053). The diminished airway inflammation correlated with a reduction in serum IgE and decreased Th2 cytokines and chemokines, such as IL-4, -5, -13, eotaxin, and Thymus- and Activation-Regulated Chemokine (TARC).

Increased TSLP expression in the airway lamina propria was observed specifically in severe asthma patients (Shikotra et al., 2012, Journal of Allergy and Clinical Immunology 129, 104-111.e109). Moreover, several studies have shown an association between the frequency of a single-nucleotide polymorphism (SNP) in the human TSLP locus and levels of TSLP expression and disease susceptibility for asthma and eosinophilic esophagitis (Ferreira et al., 2014, The Journal of allergy and clinical immunology 133, 1564-1571; Harada et al., 2011, American journal of respiratory cell and molecular biology 44, 787-793; He et al., 2009, The Journal of allergy and clinical immunology 124, 222-229; Rothenberg et al., 2010, Nature Genetics 42, 289-291). In a recent study, TSLP gene variants were also found to be associated with a significant increase in asthma risk in childhood asthma through epistatic associations (Biagini Myers et al., 2014, The Journal of allergy and clinical immunology 134, 891-899 e893).

Combination Therapies

The various treatments described above can be combined with other treatment partners such as the current standard of care for TSLP-related inflammatory conditions. Accordingly, the methods of treating a TSLP-related inflammatory condition described herein can further include administering a second agent to the subject in need of treatment. In some embodiments, the second agent can be selected from, but is not limited to, corticosteroids, bronchodilators (SABA, LABA, SAMA, LAMA), antihistamines, antileukotrienes, and PDE-4 inhibitors.

The term "combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g., a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent. The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. One skilled in the art will recognize methods and materials similar or equivalent to those described herein, could be used in the practice of the present invention. Indeed, the present invention is in no way limited to the methods and materials described.

EXAMPLES

Example 1: Generation of Human Anti-TSLP Antibodies and Fab Fragments Thereof Using Phage Display Fabs that specifically bind to human TSLP isoform 1 (SEQ ID NO: 27) were generated using the MorphoSys HuCAL PLATINUM® phage display technology. The phagemid library is based on the HuCAL® concept (Knappik et al., 2000, J Mol Biol 296, 57-86) and employs the CysDisplay™ technology for displaying the Fab on the phage surface (Lohning, WO 2001/05950).

Panning

Three types of panning were performed: solid phase panning against directly coated recombinant human TSLP (rhTSLP), solid phase amyloid precursor protein (APP) capture panning, and solution panning against TSLP.

For solid phase panning against directly coated rhTSLP, the 96-well Maxisorp™ plates were coated with 300 µl of $E.$ $coli$ derived rhTSLP (R&D Systems) per well at 4° C. overnight. For each panning, about $4 \times 10^{13}$ HuCAL PLATINUM® phage-antibodies were added to each antigen coated and incubated for 2 h at RT on a microtiter plate shaker. Afterwards, unspecific bound phages were washed off by several washing steps and specifically bound phages, were eluted using 25 mM DTT in 10 mM Tris/HCl pH 8. The DTT eluate was transferred into 14 ml of $E.$ $coli$ TG1, and incubated for phage infection.

The infected bacteria were resuspended in 2×YT medium, plated on LB/Cam agar plates and incubated o/n. Colonies were scraped off the plates and were used for phage rescue, polyclonal amplification of selected clones, and phage production. With purified phage the next panning round was started. The second and third round of solid phase panning was performed according to the protocol of the first round except for decreased amounts of antigen and more stringent washing conditions.

In solid phase APP capture panning against Cyno TSLP, the antigens used in the pannning had an APP6 (amyloid-precursor-protein) tag, and the antigen-APP6 fusion proteins were captured via a mouse anti-APP6 antibody which is immobilized on a Maxisorp™ plate. To prevent selection of phage binding to the APP6-tag of the antigen or to the anti-APP6 capture antibody, pre-blocking of phage using the capture antibody and an irrelevant APP6-tagged antigen was performed.

The 96-well Maxisorp™ plates were coated with 300 µl of anti-APP antibody and irrelevant APP6-tagged antigen o/n at 4° C. Antigen human TSLP_Avi-APP6 or cyno TSLP_APP6-Avi were captured for 1 h at RT on shaker. In parallel, phages were pre-adsorbed twice on anti-APP antibody and irrelevant antigen.

Besides the antigen coating and phage blocking procedures, the capture panning was performed like the solid phase panning described above.

For solution panning against TSLP, phages were blocked with 50% human serum/0.33× chemiblocker/0.05% Tween20. Per phage pool, 4 mg Streptavidin beads (Dynabeads® M-280 Streptavidin; Invitrogen) were blocked in 1× Chemiblocker. For removal of Streptavidin- or bead-binding phage, pre-adsorption of blocked phage particles was performed twice using blocked Streptavidin beads each. Then, biotinylated antigen human TSLP_Avi-APP6 was added to the phage particles. After incubation the phage-antigen complexes were captured using Streptavidin beads and phage particles bound to the Streptavidin beads were collected with a magnetic separator. Unspecific bound phages were washed off by several washing steps using PBS/0.05% Tween20 and PBS. Specifically bound phages were eluted from Streptavidin beads by using 25 mM DTT in 10 mM Tris/HCl pH 8. Subsequent phage infection and phage production was performed according to the Solid Phase Panning protocol and the next panning round was started.

Expression

To facilitate rapid expression of soluble Fab, the Fab encoding inserts of the selected HuCAL PLATINUM® phage were subcloned from pMORPH®30 display vector into pMORPH®x11 expression vector pMORPH®11_FH. After transformation of *E. coli* TG1-F-single clone expression and preparation of periplasmic extracts containing HuCAL®-Fab fragments were performed as described previously (Rauchenberger et al., 2003, J Biol Chem 278: 38194-38205).

Chloramphenicol resistant single clones were picked into the wells of a sterile 384-well microtiter plate pre-filled with 2×YT medium and grown o/n at 37° C. Next morning, glycerol containing medium was added into each well of the masterplates; plates were sealed with aluminum foil and stored at −80° C.

ELISA Screening

Using ELISA screening, single Fab clones are identified from panning output for binding to the target antigen. Fabs are tested using Fab-containing crude *E. coli* lysates. For verification of Fab expression in the prepared *E. coli* lysates, Maxisorp™ 384 well plates were coated with Fd fragment specific sheep anti-human IgG diluted 1:1000 in PBS. After blocking with 5% skim milk powder in PBS containing 0.05% Tween20, Fab containing *E. coli* lysates were added. Subsequently the bound HuCAL®-Fab fragments were detected by incubation with F(ab)2 specific goat anti-human IgG conjugated to alkaline phosphatase (diluted 1:5000) followed by addition of AttoPhos fluorescence substrate (Roche, #11681982001). Fluorescence emission at 535 nm was recorded with excitation at 430 nm.

To perform ELISA screening on directly coated antigen, Maxisorp™ 384 well plates were coated with different TSLP antigens at a concentration of 2 µg/ml in PBS. After blocking of plates with 5% skim milk powder in PBS, Fab-containing *E. coli* lysates were added. Binding of Fabs was detected by F(ab)2 specific goat anti-human IgG conjugated to alkaline phosphatase (diluted 1:5000) using Attophos fluorescence substrate (Roche, #11681982001). Fluorescence emission at 535 nm was recorded with excitation at 430 nm.

To perform ELISA screening on APP-captured antigen, Maxisorp™ 384 well plates were coated with anti-APP specific antibody at a concentration of 2.5 µg/ml in PBS. After blocking of plates with 5% skim milk powder in PBS, APP-tagged TSLP antigens at a concentration of 2 µg/ml was allowed to bind for 1 hour at RT. Then Fab-containing *E. coli* lysates were added. Binding of Fabs was detected by F(ab)2 specific goat anti-human IgG conjugated to alkaline phosphatase (diluted 1:5000) using Attophos fluorescence substrate (Roche, #11681982001). Fluorescence emission at 535 nm was recorded with excitation at 430 nm.

To perform ELISA screening of biotinylated antigen, Maxisorp™ 384 well plates were coated with Fd fragment specific sheep anti-human IgG (The binding site, #PC075) diluted 1:1000 in PBS or anti-His specific mouse IgG (R&D Systems, #MAB050) respectively. After blocking with 5% skim milk powder in PBS, Fab-containing *E. coli* lysates were added. Subsequently the captured HuCAL®-Fab fragments were allowed to bind to 0.7-1.5 µg/ml biotinylated hu TSLP, hu TSLP or cy TSLP respectively, which was detected by incubation with streptavidin conjugated to alkaline phosphatase followed by addition of AttoPhos fluorescence substrate (Roche, #11681982001). Fluorescence emission at 535 nm was recorded with excitation at 430 nm.

Biotinylated antigens (2.5-5 µg/ml) were also captured on Neutravidin-coated plates. After blocking with 5% skim milk powder in PBS, Fab-containing *E. coli* lysates were added. Binding of Fabs was detected by F(ab)2 specific goat anti-human IgG conjugated to alkaline phosphatase (diluted 1:5000) using Attophos fluorescence substrate (Roche, #11681982001). Fluorescence emission at 535 nm was recorded with excitation at 430 nm.

9984 clones (384 clones/panning subcode) were analyzed in primary ELISA Screening on biotinylated human TSLP_Avi-APP6 and biotinylated cyno TSLP_APP6-Avi coated on NA-plates (see 3.4.4). ELISA results were analyzed with GENios Pro program "PrimeScreen." Results were analyzed compared to background signal. For human antigen only wells with signals >10× background and for cyno antigen wells with signals >5× background were selected as positive. Signals lower than 5× background are likely to be the result of low expressed Fab, Fab of low affinity, edge effects of the microtiter plate, or non-reproducible values. The solution panning resulted in 3133, the solid phase panning in 240 primary hits. 1472 selected primary hits were further analyzed in secondary ELISA screening.

Different antigen presentation modes were used in secondary ELISA screening, including C- or N-terminal Avi-APP6 tagged antigens, directly coated antigens, biotinylated antigens presented in solution, HEK-derived antigens, *E. coli* derived antigens, de-glycosylated variants of the antigens (PNGase treated). Additionally, unspecific binding to the countertarget IL-7 was analyzed in secondary screening. To exclude biotin- and tag-binders, a biotinylated irrelevant APP-Avi tagged antigen was used. The ELISA results were analyzed with GENios Pro program "PrimeScreen" and the results were analyzed compared to background signal. For the irrelevant antigen and the countertarget IL-7, only hits with signals <2 fold background were selected.

The results of the secondary screening indicate that the antigen presentation mode is crucial for cross-reactivity. The screening on deglycosylated antigen showed that there might be binders targeting a glyco-epitope. Furthermore, the tag location and tag-composition may influence cross-reactivity due to conformational changes. The clones were grouped according to their cross-reactivity profiles resulting in seven different cross-reactivity groups. Group 1-3 comprises all clones that are cross-reactive to E. coli-derived huTSLP either alone or in combination with HEK-derived antigens. Group 4 includes all clones that are at least cross-reactive to human TSLP_Avi-APP6 presented in solution. In contrast group 5 includes all clones that are cross-reactive to human TSLP_Avi-APP6 in solution exclusively. In group 6 there are all clones that are cross-reactive to human TSLP_Avi-APP6 and to deglycosylated human TSLP_Avi-APP6, and in group 7 there are all clones that are cross-reactive to all HEK-derived antigens including the deglycosylated antigens.

Sequencing and Conversion to IgG

Sequence analysis was performed on 73 clones out of cross-reactivity group 1-3 (clones cross-reactive to E. coli derived TSLP) and of 569 clones out of group 4-7 (clones that are cross-reactive to HEK-derived antigens). In total, 297 HCDR3 unique clones were identified, 222 clones were consolidated, and 124 clones were purified in Fab format.

The clones derived from the third and fourth sequencing analysis were immediately put into the IgG conversion . . . and subsequently cloned into the pMORPH®4_IgG1f vector for expression in mammalian cells.

Affinity Determination

Dissociation constant ($K_D$) determination of HuCAL® Fab and IgG version of clones was performed as follows: biotinylated human TSLP was coated at 0.2 µg/ml in assay buffer for 1 hour at RT on streptavidin MSD plates. The Streptavidin plates were blocked overnight at 4° C. with PBS with 3% BSA before antigen coating. The solution equilibrium titration (SET) was performed with human TSLP and cyno TSLP under the conditions described below. Monomer fractions of antibody protein were used (at least 90% monomer content, analyzed by analytical SEC; Superdex75 (Amersham Pharmacia) for Fab, or Tosoh G3000SWXL (Tosoh Bioscience) for IgG, respectively).

Affinity determination in solution was basically performed as described in the literature (Friquet et al., 1985, J Immnunol Meth 77, 305-319). To improve the sensitivity and accuracy of the SET method, it was transferred from classical ELISA to ECL based technology (Haenel et al., 2005, Anal Biochem 339, 182-184). 1 mg/ml goat-anti-human (Fab)2 fragment specific antibodies (Dianova) were labeled with MSD Sulfo-TAG™ NHS-Ester (Meso Scale Discovery, Gaithersburg, Md., USA) according to the manufacturer's instructions.

The experiments were carried out in polypropylene microtiter plates and PBS pH 7.4 containing 0.5% BSA and 0.02% Tween-20 as assay buffer. Unlabeled antigen was diluted in a $2^n$ series, starting with a concentration at least 10 times higher than the expected $K_D$. Wells without antigen were used to determine Bmax values; wells containing only assay buffer were used to determine background. After addition of appropriate amount of binder (antibody concentration similar to or below the expected $K_D$, 60 µl final volume), the mixture was incubated over night at RT.

MSD plates were coated with antigen (30 µl per well). After washing the plate with PBS with 0.02% Tween-20, the equilibrated samples were transferred to those plates (30 µl per well) and incubated for 20 min. After washing, 30 µl per well of the MSD-Sulfo-tag labeled detection antibody (anti-human (Fab)2, final dilution typically 1:2,000) was added to the MSD plate and incubated for 30 min at RT on an Eppendorf shaker (700 rpm).

After washing the MSD plate and adding 30 µl/well MSD Read Buffer T with surfactant, electrochemiluminescence signals were detected using a Sector Imager 6000 (Meso Scale Discovery, Gaithersburg, Md., USA).

The data was evaluated with XLfit (IDBS) software applying customized fitting models. For $K_D$ determination of Fab molecules the following fit model was used (according to Haenel et al., 2005), modified according to (Abraham et al., 1996)):

$$y = B_{max} - \left(\frac{B_{max}}{2[Fab]_t}\left([Fab]_t + x + K_D - \sqrt{([Fab]_t + x + K_D)^2 - 4x[Fab]_t}\right)\right)$$

$[Fab]_t$: applied total Fab concentration
x: applied total soluble antigen concentration (binding sites)
$B_{max}$: maximal signal of Fab without antigen
$K_D$: affinity For $K_D$ determination of IgG molecules the following fit model for IgG was used (modified according to Piehler et al., 1997):

$$y = \frac{2B_{max}}{[IgG]}\left([IgG] - \left(\frac{x + [IgG] + K_D}{2} - \sqrt{\frac{(x + [IgG] + K_D)^2}{4} - x[IgG]}\right)^2\right)$$

[IgG]: applied total IgG concentration
x: applied total soluble antigen concentration (binding sites)
$B_{max}$: maximal signal of IgG without antigen
$K_D$: affinity Affinity can also be determined by Biacore surface plasmon resonance (SPR) by determining kinetic rate constants using the Biacore 3000 or T200 instrument (Biacore, GE Healthcare). Biacore $K_D$ determination via directly coated antigen was basically performed as follows: 50 RU biotinylated antigen human TSLP was captured on a SA chip (Biacore, GE Healthcare). The reference flow cell 1 was kept blank. PBS pH7.2 GIBCO+0.05% Tween 20 was used as running buffer with a flow rate of 30 µl/min. Fab concentrations ranging from 3.9 to 500 nM were used with an injection volume of 45 µl and a dissociation time of 300 sec. Regeneration of bound analyte was done with 2× injections a 5 µl of 10 mM Glycine pH 1.5. The raw data was fitted to a 1:1 binding model, with parameter(s) $R_{max}$ set to local and RI set to 0.

Affinity Maturation

Seven Fab candidates were selected for affinity maturation. To increase affinity and biological activity of selected Fabs, L-CDR3 and HCDR2 regions were optimized in parallel by cassette mutagenesis using trinucleotide directed mutagenesis (Virnekas et al., 1994, Nucleic Acids Res 22: 5600-5607), while the framework regions were kept constant. For optimizing L-CDR3 of parental Fab fragments, the LCDR3, framework 4 and the constant region of the light chains (405 bp) of the binder pool were removed by enzymatic digestion and replaced by a repertoire of diversified L-CDR3s together with framework 4 and the constant domain. In a second library set the H-CDR2 was diversified, while the connecting framework regions were kept constant. Ligation mixtures were electroporated in 4 ml E. coli TOP10F cells yielding from 108 to 109 independent colonies. This library size ensured coverage of the theoretical diversity. Amplification of the library was performed as described (Rauchenberger et al., 2003, J Biol Chem 278: 38194-38205). For quality control, single clones were randomly picked and sequenced. For the selection of affinity improved binders phage derived from maturation libraries were subjected to three rounds of solution panning using biotinylated antigenhuman TSLP_Avi-APP6 and cyno TSLP_APP6-Avi. Stringency was increased by lowering the antigen concentration in each panning round (Low et al., 1996, J Mol Biol 260, 359-368. 1996.). In addition to antigen reduction off-rate selection (Hawkins et al., 1992, J Mol Biol 226, 889-896) was performed. This was combined with prolonged washing steps o/n at RT.

To further increase affinity and biological activity of some selected antibody fragments, L-CDR1, L-CDR3, H-CDR2, H-CDR1 regions were optimized in parallel by cassette mutagenesis using trinucleotide directed mutagenesis (Virnekas et al., 1994, Nucleic Acids Res 22: 5600-5607), while the framework regions were kept constant.

Posttranslational modifications (PTMs) in the CDRs are not desired since the potency of such antibodies might potentially be decreased depending on the position of the PTM, in addition, PTMs could lead in non-homogenous compound. Prior affinity maturation, variants devoid of NG, NS, and DG sites were generated and included in a pool with the parental clone with the aim to select PTM removed variants during the selection process. Fab containing crude bacterial cell lysates of the generated variants were tested for antigen binding in ELISA on human TSLP. The plasmid DNA of the variants was mixed with the parental DNA for the generation of maturation libraries.

For ranking of the matured binders by Solution Equilibrium Titration based on the principles described by Haenel et al., 2005, Anal Biochem 339: 182-184, a constant amount of diluted BEL extract was equilibrated over night with different concentrations of antigen. Then the mixture was transferred to MSD Plates which were previously coated with antigen, and after incubation and washing, a suitable MSD-Sulfo-tag labeled detection antibody was added. Subsequently, the concentration of unbound Fab was quantified via ECL detection using the Sector Imager 6000 (Meso Scale Discovery, Gaithersburg, Md., USA). Results were processed using XLfit (IDBS) software, applying the corresponding fit model to estimate affinities and thus identify clones most improved by the maturation.

Production

Eukaryotic HKB11 cells were transfected with pMORPH®4 expression vector DNA encoding both heavy and light chains of anti-TSLP Fabs or IgGs. The cell culture supernatant was harvested 3 or 6 days post transfection. After sterile filtration, the solution was subjected to Protein A affinity chromatography (MabSelect SURE, GE Healthcare) using a liquid handling station. If not otherwise stated, buffer exchange was performed to 1× Dulbecco's PBS (pH 7.2, Invitrogen) and samples were sterile filtered (0.2 µm pore size). Protein concentrations were determined by UV-spectrophotometry and purity of IgGs was analyzed under denaturing, reducing conditions using a Labchip System (Perkin Elmer, USA).

Anti-TSLP Fab1

Anti-TSLP Fab1 was derived from the MOR011086 family, which was identified in the initial pannings. Affinity maturation of MOR011086 resulted in generation of MOR014051, which included a DG posttranslational modification motif in the HC-CDR2. Removal of this DG motif lead to generation of MOR14701 (DG→DA), which was then germlined to produce the MOR014824, i.e., Mab1 in Table 2. The anti-TSLP Fab1 in Table 2 is the Fab fragment of Mab1.

The amino acid sequences of anti-TSLP Fab1 heavy chain CDRs (HCDRs), light chain CDRs (LCDRs), by Kabat, Chothia, or combined numbering schemes, as well as the amino acid sequences of the heavy and light chain variable regions were determined and listed in Table 2. Anti-TSLP Fab1 bound with very high affinity ($K_D$=6 pM) to recombinant human TSLP as determined by SET. Anti-TSLP Fab1 did not bind to a structurally similar cytokine, IL-7.

Example 2: Potency of Anti-TSLP Fab1 Against Recombinant and Naturally Secreted Human TSLP in Reporter Gene Assays The potency of anti-TSLP Fab1 against a recombinant human TSLP, a naturally-secreted human TSLP, and Cyno TSLP were tested in a luciferase reporter gene assay.

Materials and Methods

The naturally-secreted human TSLP was obtained from human lung fibroblast cells by stimulation with IL-1β, TNF-α, and IL-13 for 24 hours.

Ba/F3 cells were transfected with hTSLPR, hIL7Rα and a Stat5-luciferase reporter construct. Stat5 is a downstream effector of TSLP signaling. Cells were grown in the Cell Growth Media: RPMI 1640 (Invitrogen, Grand Island, N.Y.) with 10% FCIII (Fisher Scientific, Pittsburgh, Pa.), 1% Penicillin/Streptomycin (Invitrogen, Grand Island, N.Y.), 1 µg/ml puromycin (Sigma, St. Louis, Mo.), and 5 ng/ml recombinant human TSLP (rhTSLP, R&D Systems, Minneapolis, Minn.). The Reporter Assay Buffer was made using RPMI 1640 with 10% FCIII, 1% Penicillin/Streptomycin, and 1 µg/ml Puromycin.

Ba/F3 cells were grown in suspension in a T162 cm² flask and split 1:50 twice a week. Ba/F3 cells were collected and pelleted at the mid-log growth phase by centrifugation at 200×g for 5 minutes and washed in TSLP-free Cell Growth Media. This was repeated and then incubated for 18-24 hours in TSLP-free conditions. The following day the cells were again pelleted by centrifugation at 200×g for 5 minutes, and resuspended in the Reporter Assay Buffer to a cell concentration of 1×10⁶ cells/mL. 10 µL of Ba/F3 cells at 1×10⁶ cells/mL was combined with 70 µL of Reporter Assay Buffer in each well of a white 96-well Optiplate (Perkin Elmer, Waltham, Mass.). This was followed by 10 µL of a 6 point 1:10 serial dilution of antibody (100 nM top final concentration) and incubated for 30 minutes at 37° C./5% $CO_2$ in a humidified incubator. Finally, 10 µL of 0.5 ng/mL human or cyno TSLP or a calculated concentration of naturally-secreted TSLP with the same relative activity, and the plate was sealed to reduce evaporation, and incubated for 4 hours at 37° C./5% CO2 in a humidified incubator. The plate was then removed from the incubator, and allow equilibrate to room temperature for about 15 minutes. This was followed by the addition of 100 µL of Steady-Glo reagent (Promega, Madison, Wis.) to each well and incubated at room temperature for 20 minutes. The plates were then read on the Envision instrument, using the luminescence programme (camera exposure 1 second per well) and the data analysed in Microsoft Excel and Graphpad Prism.

Results

Anti-TSLP Fab1 demonstrated excellent potency against all three forms of TSLP in the luciferase reporter gene assay, with IC50 of 15.4 pM against the recombinant human TSLP (1 ng/ml), IC50 of 17.1 pM against the naturally secreted human TSLP, and IC50 of 10.8 pM against the Cyno TSLP. When mean reporter gene assay results for multiple experiments (n=3) were calculated, mean IC50 values for Fab1 against recombinant human TSLP was 15.3 pM±1.5 pM SEM. Mean IC50 values for Fab1 against cyno TSLP was 9.5 pM±0.9 pM SEM.

Thus, anti-TSLP Fab1 is a potent inhibitor of human and Cyno TSLP with picomolar potency. The fact that anti-TSLP Fab1 demonstrated excellent potency against the naturally secreted TSLP from human lung fibroblasts reduced the likelihood of problems caused by differential glycosylation of active human TSLP in body and the recombinant human TSLP used to generate the anti-TSLP Fabs.

Example 3: Inhibition of TSLP-Induced TARC (Thymus- and Activation-Regulated Chemokine) Secretion from Primary Human Peripheral Blood Mononuclear Cells (PBMC) by Anti-TSLP Fab1

To determine if anti-TSLP Fab1 was able to neutralize TSLP in the context of a primary cell driven response, human or Cyno TSLP-induced TARC secretion from human PBMCs was tested in the presence or absence of anti-TSLP Fab1.

Materials and Methods

Venous blood taken from healthy donors was heparinised (Sigma, St. Louis, Mo.) and collected in 50 mL syringes and then split into two sterile falcon tubes, 25 ml in each. These tubes were centrifuged at 1200 rpm for 20 minutes with low acceleration and deceleration before removal of the plasma layer using a Pasteur pipette. 20 ml of blood from each tube was transferred into fresh 50 ml Falcon tubes and 20 mL of PBS (1x, Invitrogen, Grand Island, N.Y.) and 10 mL 4% Dextran (w/v, Sigma, St. Louis, Mo.) were added to each. The tubes were inverted to throroughly mix the blood and dextran and they were then incubated at room temperature for 30 minutes to allow the red blood cells to sediment. 20 mL of supernatant was transferred to a fresh 50 ml Falcon tube and washed with 30 ml PBS (1400 rpm for 8 minutes) before aspirating the supernatant and resuspending the cell pellet in 10 mL PBS.

To lyse the red blood cells, 20 mL sterile cold distilled water (Sigma, St. Louis, Mo.) was added to the cells and mixed with a 20 ml stripette for 1 minute before 20 ml sterile cold 2×PBS was added to stop the lysis. Tubes were inverted several times and centrifuged at 1400 rpm for 8 minutes before being pooled into one tube and washed twice with the assay buffer (1400 rpm, 8 minutes). The assay buffer was made with RPMI 1640 (with GlutaMax, Invitrogen, Grand Island, N.Y.) with 10% Human AB Serum (Life Technologies, Grand Island, N.Y.) and 1% Penicillin/Streptomycin (Invitrogen, Grand Island, N.Y.).

Cells were counted and resuspended at a concentration of $10 \times 10^6$ cells per ml, 100 µl of which was added to each well of a 96 well flat bottom plate ($1 \times 10^6$ cells per well). 50 µl/well of anti-TSLP antibody was added into each well and left to incubate for 30 minutes at 3TC before the addition of human or Cyno TSLP, yielding a final concentration of 1 ng/ml TSLP (66 pM). Cells were incubated for 24 hours before the plates were centrifuged at 1300 rpm for 5 minutes and supernatants were collected for Thymus- and Activation-Regulated Chemokine (TARC) analysis by ELISA. Supernatants were stored at −20° C. until they were thawed out for analysis in the TARC ELISA (samples tested neat).

TARC ELISA analysis were performed following the manufacturer's protocols (R&D Systems, Minneapolis, Minn.). Briefly, capture antibody was diluted to the working concentration in PBS without carrier protein. Microplate immuno maxiSorp plates (Fisher Scientific, Pittsburgh, Pa.) were coated with 100 µL per well of the diluted capture antibody, plates were sealed with top seal adhesive lids and incubated overnight at room temperature. The following day, capture antibody was aspirated and plates washed with wash buffer, repeating the process two times for a total of three washes. Wells were washed by filling each well with 300 µL wash buffer using a manifold dispenser or autowasher. After the last wash, remaining wash buffer was discarded by inverting the plate and blotting it against clean paper towels. Plates were then blocked by adding 300 µL of reagent diluent (1% BSA in PBS) to each well. Plates were incubated at room temperature for a minimum of 1 hour. Wash steps were repeated and 100 µL of sample or standards in reagent diluent were added per well. Plates were covered with an adhesive strip and incubated for 2 hours at room temperature. The aspiration/wash steps were then repeated and 100 µL of the diluted detection antibody was added to each well, covered with a new adhesive strip and incubated for 2 hours at room temperature before repeating the wash step as described previously. 100 µL of the working dilution of Streptavidin-HRP was added to each well and the plates were then re-covered and incubated for 20 minutes at room temperature, avoiding placing the plate in direct light. The aspiration/wash steps were then repeated and 100 µL of TMB substrate solution was added to each well. Plates were incubated for up to 20 minutes at room temperature in darkness followed by the addition of 50 µL Stop Solution. The plate was gently tapped to ensure mixing of the wells and the optical density of each well was immediately determined using a microplate reader set to 450 nm.

Results

Anti-TSLP Fab1 was a very potent inhibitor of recombinant human TSLP-induced TARC secretion from human PBMC with an IC50 of 20.3 pM and IC90 of 99.65 pM against 1 ng/ml recombinant human TSLP. Anti-TSLP Fab1 was shown to be a potent inhibitor of Cyno TSLP-induced TARC secretion from human PBMC with an IC50 of 11.3 pM against 1 ng/ml recombinant Cyno TSLP. When mean human PBMC results for multiple experiments (n=3) were calculated, mean IC50 values for Fab1 against recombinant human TSLP was 19.7 pM±1.9 pM SEM. Mean IC50 values for Fab1 against cyno TSLP was 11.1 pM±0.5 pM SEM.

Example 4: Inhibition of TSLP-Induced MDC (Macrophage-Derived Chemokine) Secretion from Primary Cyno Peripheral Blood Mononuclear Cells (PBMC) by Anti-TSLP Fab1

Materials and Methods

Cyno venous blood was collected into vacutainer tubes containing lithilum heparin by Covance (Dedham, Mass.). 30 ml blood from each donor was transferred into 50 ml falcon tubes and centrifuged at 1200 rpm for 20 minutes with low acceleration and deceleration before the plasma layer was removed using a Pasteur pipette, leaving a 0.5 cm gap between layers. The remaining bottom layer of cells was resuspended and 10 ml was transferred to fresh falcon tubes followed by 10 ml 1×PBS and 5 ml 4% Dextran (w/v, Sigma, St. Louis, Mo.) before inverting the tubes 4-5× to mix thoroughly. All tubes were incubated at room temperature in a fume hood for 25 minutes to allow the RBCs to sediment at the bottom of the tube. 10 mL of supernatant was transferred to a fresh 50 ml Falcon tube and washed with 40 ml culture medium (1400 rpm for 8 minutes) before aspirating the supernatant and resuspending the cell pellet in 5 mL 1×PBS.

To lyse the red blood cells, 20 mL sterile cold distilled water (Sigma, St. Louis, Mo.) was added to the cells and mixed with a 20 ml stripette for 1 minute before 20 ml sterile cold 2×PBS was added to stop the lysis. Tubes were inverted several times and centrifuged at 1400 rpm for 8 minutes before being pooled into one tube and washed twice with the culture medium (1400 rpm, 8 minutes, 4° C.). The culture medium was made with RPMI 1640 (with GlutaMax, Invitrogen, Grand Island, N.Y.) with 10% Fetal clone III (Fisher Scientific, Pittsburgh, Pa.) and 1% Penicillin/Streptomycin (Invitrogen, Grand Island, N.Y.).

Cells were counted using Trypan blue dye and resuspended at a concentration of $10 \times 10^6$ cells per ml, 100 µl of which was added to each well of a 96 well flat bottom plate ($1 \times 10^6$ cells per well). 50 µl/well of anti-TSLP antibody (100 nM top final concentration) was added into each well and left to incubate for 30 minutes at 3TC before the addition of Cyno TSLP, yielding a final concentration of 0.5 ng/ml TSLP (33 pM). Cells were incubated for 24 hours before the plates were centrifuged at 1400 rpm for 8 minutes and supernatants were collected for macrophage-derived chemokine (MDC, CCL22) analysis by ELISA. Supernatants were stored at −20° C. until they were thawed out for analysis in the MDC ELISA (diluted 1:2 in assay buffer before addition to ELISA plate). MDC ELISA analysis were performed following the manufacturer's protocols (R&D Systems, Minneapolis, Minn.).

Results

Anti-TSLP Fab1 was shown to a potent inhibitor of recombinant Cyno TSLP-induced MDC secretion from Cyno PBMC with an IC50 of 55.5 pM against 0.5 ng/ml recombinant Cyno TSLP. When mean cyno PBMC results for multiple experiments (n=3) were calculated, mean IC50 values for Fab1 against cyno TSLP was 25.1 pM±5.9 pM SEM.

Example 5: Species Cross-Reactivity of Anti-TSLP Fab1

Materials and Methods

Biacore surface plasmon resonance (SPR) binding analyses were carried out to establish whether the anti-TSLP Fab1 binds to human, mouse, or rat TSLP protein. The Biacore reagents, including Series S Sensor Chip CM5, HBS-EP+ buffer, human Fab Capture Kit, EDC (1-ethyl-3-(3-dimethylaminopropyl)-carbodiimide), NHS (N-hydroxysuccinimide), Ethanolamine, BIAnormalizing solution, 70% (w/w) glycerol, and glycine, were purchased from GE Healthcare. Running buffer used for both Fab capture and TSLP binding analyses was 1×HBS-EP+, with 10 mM HEPES (pH 7.4), 150 mM NaCl, 3 mM EDTA, 0.05% v/v surfactant P20. Recombinant human, cyno, or mouse TSLP (MW 15 kDa) were obtained from R&D Systems (Minneapolis, Minn.). Recombinant rat TSLP (MW 15.4 kDa) was obtained from USCN Life Science Inc. (Wuhan, China).

A capture approach was used to prepare anti-TSLP Fab1 on a Biacore CM5 chip prior to injection of human, mouse, or rat TSLP. Human Fab binder was immobilized on all four flow cells of a CM5 chip using a Human Fab Capture kit following manufacturer's instructions. A contact time of 360 seconds at a flow rate of 10 uL/min was specified. The temperature of the sample compartment was 10° C. and analysis temperature was 25° C.; prior to immobilization, the CM5 chip was primed with HBS-EP+ and normalized with BIAnormalizing solution. 375 uL of 20 ug/mL human Fab binder was prepared by combining 15 uL 0.5 mg/mL stock with 360 uL pH5 immobilization buffer (both provided in Human Fab Capture kit). Resultant immobilization levels were approximately 4000-4400RU human Fab binder in Fc1, 2, 3 and 4.

A custom Biacore method was used to set up a kinetics assay in which approx. 14RU anti-TSLP Fab1 was captured per cycle. This was achieved by injecting 5 nM anti-TSLP Fab1 in HBS-EP+ buffer with a contact time of 60s at a flow rate of 10 uL/min, followed by a stabilization period of 30s. The temperature of the sample compartment was 10° C. and analysis temperature was 25° C. Using this custom Biacore method, a kinetics assay was set up to evaluate hTSLP, mTSLP, and rTSLP interaction with captured anti-TSLP Fab1. For each antigen, the following 10 concentrations were prepared in HBS-EP+ and injected over the anti-TSLP Fab1 surface, including a 0 nM buffer blank, 10 nM, 5 nM, 2.5 nM, 1.25 nM, 0.625 nM, 0.313 nM, 0.156 nM, 0.078 nM, 0.039 nM, 0.02 nM. After capture of ~14RU anti-TSLP Fab1, antigen was injected at 45 uL/min for 360s, followed by a dissociation period of 600s (for all concentrations tested) or 1200s (for 0 nM and 2.5 nM antigen concentrations). Regeneration of the Fab binder surface was achieved after each cycle by injecting 10 mM glycine-HCl, pH 2.0 for 60s at 10 uL/min, followed by an extra wash with HBS-EP+ buffer. The temperature of the sample compartment was 10° C. and analysis temperature was 25° C.

All SPR experiments and analyses were run on Biacore T200 instruments controlled by Biacore T200 Control software. Data were processed using Biacore T200 Evaluation software. Blank-subtracted sensorgrams were plotted for qualitative analysis of the cross-species reactivity of anti-TSLP Fab1.

Results

Biacore SPR cross-reactivity experimental results showed tight binding of anti-TSLP Fab1 to recombinant human TSLP, whereas there is no detectable binding to recombinant rat or mouse TSLP, which is consistent with the low homology between human and rodent TSLP (about 40%).

Anti-TSLP Fab1 bound with very high affinity to cynomolgus monkey recombinant TSLP and was a very potent inhibitor of recombinant cyno TSLP (IC50=10.8 pM against 1 ng/ml recombinant TSLP) in the luciferase reporter gene assay. In both primary human and cyno PBMC assays, anti-TSLP Fab1 was a very potent inhibitor of recombinant cyno TSLP induced TARC secretion from human PBMC (IC50=11.3 pM) and of recombinant cyno TSLP induced MDC secretion from cyno PBMC (IC50=55.5 pM).

Thus, anti-TSLP Fab1 showed restricted species cross-reactivity, recognizing recombinant cynomolgus TSLP, but not rat or mouse TSLP.

Example 6: Efficacy of Mouse Anti-TSLP Antibody in Murine Disease Models of Asthma Materials and Methods The effect of TSLP neutralization on allergic airway responses was assessed in a murine model of systemic ovalbumin (OVA) sensitization followed by locally antigen challenge to the lung. This model was characterized by the development of a Th2 phenotype and associated eosinophilic inflammation. Since the anti-TSLP Fab1 of Example 1 did not cross-react with rodent TSLP proteins as described in Example 5, the effect of TSLP neutralization was assessed using a commercially available surrogate anti-mouse TSLP monoclonal antibody (MAB555, R&D Systems, Minneapolis, Minn.), reported to fully neutralize the biological activity of recombinant murine TSLP with an IC50 of about 1.3 nM against 0.5 nM murine TSLP (data supplied from R&D Systems). Specific ELISA kits for all cytokines and chemokines were also purchased from R&D systems.

Female Balb/c mice were immunized with OVA (or saline) and alum as an adjuvant on day 1 and day 14. Briefly, mice were immunized intraperitoneally with 0.2 mL 0.9% wt/vol NaCl (saline) containing 100 µg of ovalbumin (5× crystallized, Sigma, UK) adsorbed in 1.6 mg aluminium hydroxide (Sigma). On day 21, mice were challenged with OVA or saline given as an aerosol and culled 24 h later. Inflammation was assessed by differential and total cell counts within the bronchoalveolar lavage (BAL), whilst cytokines & chemokines were measured by specific ELISA.

Twenty four hours after the last intranasal OVA or PBS challenge, mice were anaesthetized by an intraperitoneal injection of 4 mg/Kg sodium pentobarbital (Rhone Merieux, Harlow, UK). BAL fluid was collected by cannulating the trachea and washing the lungs with a total of 1.2 ml saline solution (3×0.4 mL each). For each sample, a total cell count was determined and cytospin preparation (Shandon Scientific Ltd., Cheshire, UK) performed. Cells were stained with Diff-Quik (Baxter Dade AG, Dudingen, Switzerland) and a differential count of 200 cells performed using standard morphological criteria.

To assess the effect of TSLP depletion on the sensitization phase of the response, an antimurine TSLP monoclonal antibody (at 10 mg/Kg) or rat IgG2a isotype control was administered intravenously one hour prior to OVA sensitization and again prior to boost on day 14. To assess the role of TSLP at the time of challenge, some mice were only given antibody one hour prior to OVA aerosolization on day 21. No adverse effects were observed on intravenous administration of these antibodies.

Results are expressed as means±SEM of the indicated number of experiments. One way analysis of variance (ANOVA) was used to determine significance among the groups. If a significant variance was found, an unpaired Student's T test was used to assess comparability between means. A value of $p \leq 0.05$ was considered significant.

Results

Figure 4A:
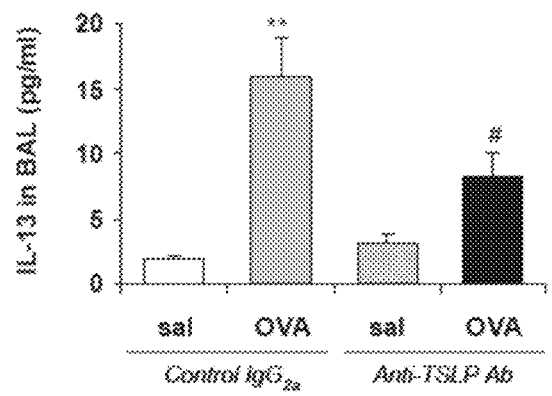
FIGS. 4A-4C are a series of bar graphs showing that neutralization of TSLP significantly attenuates the levels of IL-13 (FIG. 4A), eotaxin-2 (CCL24, FIG. 4B) and Thymus- and Activation-Regulated Chemokine (TARC, CCL17, FIG. 4C) within the lung of ovalbumin-sensitized, antigen-challenged mice. Mice sensitized with OVA (or saline) plus alum, received an intravenous administration of either anti-murine TSLP or isotype control antibody at 1 h prior to sensitizations. All mice were OVA challenged on day 21 and culled at 24 h. Values represent mean±SEM levels of mediators in the BAL, measured by specific ELISA. Statistical analysis was performed using an unpaired student's T-test. Significant differences between isotype-treated saline-sensitized and OVA-sensitized mice at $p<0.05$ are denotedby (*) and $p<0.01$ denoted by (**). Differences between isotype and anti-TSLP antibody treated OVA-sensitized mice at the $p<0.05$ are denoted by (#).
Figure 4B:
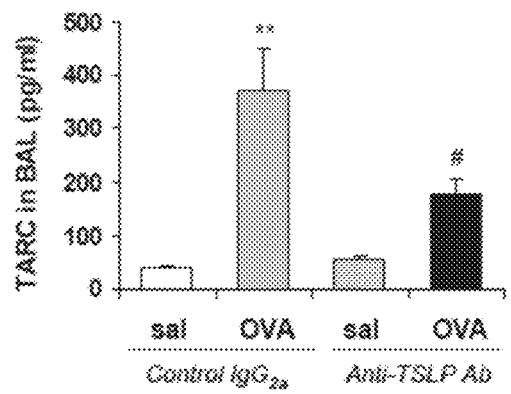
Figure 4C:
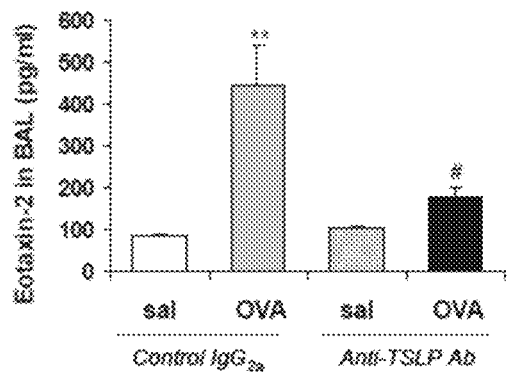

OVA sensitization and challenge resulted in an increased number of cells within the bronchoalveolar lavage fluid, which included eosinophils and neutrophils, compared to control animals (FIG. 3). This is consistent with previous experience of responses following a single antigen challenge. Furthermore, a number of inflammatory mediators were also upregulated within the lavage fluid of OVA sensitized/challenged mice compared to controls (FIGS. 4A-4C).

Anti-murine TSLP antibody treatment (10 mg/kg) significantly inhibited the total number of cells within the BAL fluid by approximately 50%, whilst the eosinophil counts were reduced by 80%. Antibody treatment in the absence of antigen sensitization did not significantly alter the baseline cellular composition of the lavage. Analysis of downstream markers of TSLP activity revealed reduced levels of IL-13 (FIG. 4A), a cytokine associated with allergic airway inflammation, and chemokines eotaxin-2 and TARC (FIGS. 4B and 4C), both of which were known chemoattractants of Th2 cells and eosinophils that were generated by TSLP-stimulated dendritic cells.

Example 7: Pharmacokinetic Characterization of Anti-TSLP Fab1 in Rats

Materials and Methods

The pharmacokinetics (PK) and lung disposition of anti-TSLP Fab1 were studied in rats following intravenous (IV) bolus injection, intratracheal instillation (ITI), or a 20-min nose-only inhalation of a single nominal dose of nebulized anti-TSLP Fab1 at 1 mg/kg. Concentrations of anti-TSLP Fab1 at various post-dose time points were determined in plasma, BAL fluid, as well as lung homogenate samples (following BAL and blood perfusion of the pulmonary vasculature).

Results

Anti-TSLP Fab1 was cleared from the systemic circulation quickly following IV injection, with an average terminal elimination half-life of about 3 hours. Following ITI or inhalation, anti-TSLP Fab1 was slowly absorbed into the systemic circulation, reaching plasma Cmax at around 2 hr for both routes, and the average terminal half-lives were longer than those determined following IV administration (7 hr after ITI and 4 hr after inhalation, compared to 3 hr after IV), indicating absorption rate-limited kinetics. The systemic bioavailability of anti-TSLP Fab1 averaged about 6% after ITI and 1% after inhalation, possibly due to a higher lung deposition fraction after ITI compared to inhalation. Compared to the low systemic exposure, anti-TSLP Fab1 concentrations in BAL fluid and lung homogenate were much higher (>100-fold higher) following ITI or inhalation, accounting for 97-99% of the total amount of dose recovered from all three matrices (66-79% for BAL and 20-31% for lung) at 2, 6, 24 or 72 hours post-dose. The estimated disposition half-lives of anti-TSLP Fab1 averaged about 7 and 9 hours in BAL and lung homogenates, respectively.

Example 8: Pharmacokinetic Characterization of Anti-TSLP Fab1 in Monkeys

Materials and Methods

The toxicokinetics, PK/PD, and lung distribution of anti-TSLP Fab1 were studied in cynomolgus monkeys following either daily 1-hr inhalation for 14 days at 1, 10 and 20 mg/kg dose (Groups 3-5), or a cross-over single dose administration of 1 mg/kg IV followed by a single inhaled dose of 20 mg/kg after a 16-day washout period (Group 6). Serial blood samples were collected for PK/PD, total TSLP was assessed as a PD marker and immunogenicity assessments. In addition, lung homogenate samples (at terminal) and BAL fluid samples (terminal for Groups 3-5 and prior to the intravenous dose and terminal for PK Group 6) were also collected for PK, total TSLP, and immunogenicity (for BAL fluid only) assessments.

Results

Figure 5:
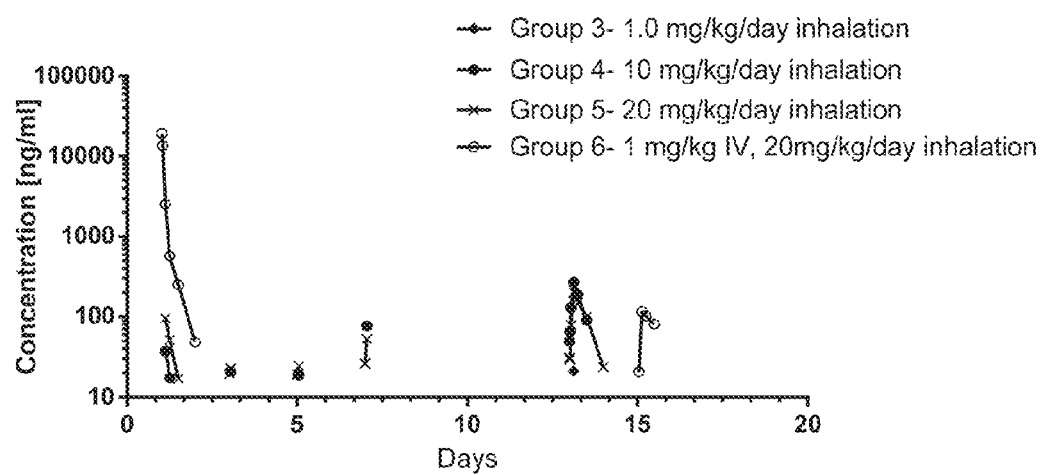
FIG. 5 is a line graph showing mean serum concentration-time profiles of total anti-TSLP Fab1 in monkeys.
Figure 6A:
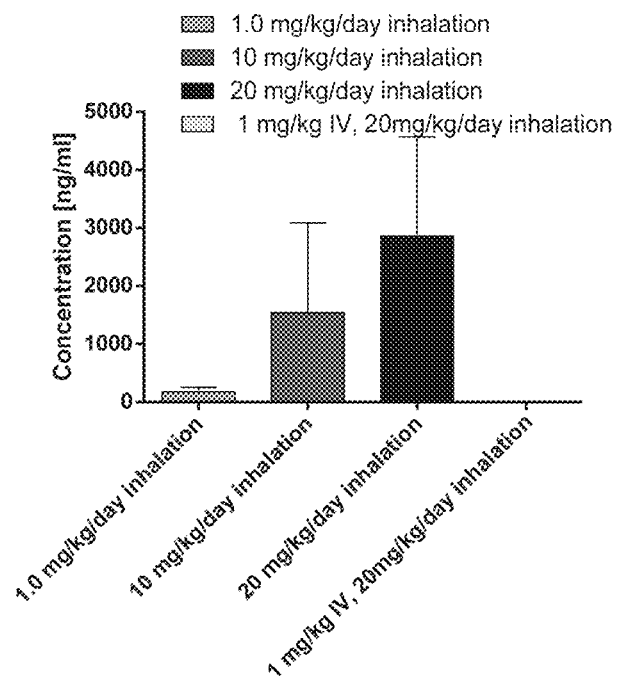
FIGS. 6A and 6B are bar graphs showing mean concentrations of total anti-TSLP Fab1 in BAL (6A) or lung homogenate (6B) in monkeys at 1 hour (1, 10, 20 mg/kg/day inhalation groups) or 6 days (1 mg/kg IV+20 mg/kg/day inhalation group) post last inhaled dose.
Figure 6B:
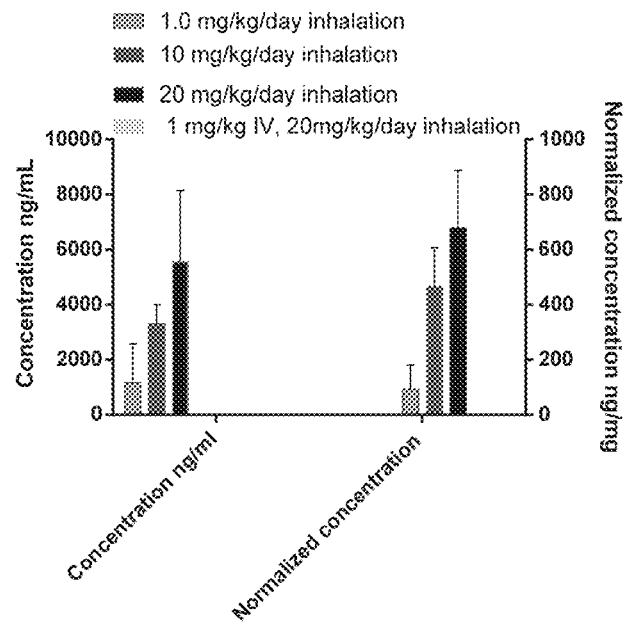

Systemic exposure of anti-TSLP Fab1 in serum was low after inhalation with an estimated bioavailability of less than 1% at the 20 mg/kg inhaled dose level. The 1 mg/kg inhaled dose did not yield any detectable systemic exposure and the 10 and 20 mg/kg inhaled doses showed comparable systemic exposure to anti-TSLP Fab1. Cmax was reached about 3 hours after inhalation. Similar to the rat PK, the systemic elimination half-lives were longer after inhalation (about 7 hours) compared to IV (about 2.3 hours), indicating absorption rate-limited kinetics. Accumulation of exposure in serum was observed after 14 days of dosing. Compared to the low serum exposure (FIG. 5), preliminary data on concentrations of anti-TSLP Fab1 in terminal BAL fluid and lung homogenates were much higher and increased with increasing doses (FIG. 6).

Example 9: Crystallography and Epitope Mapping of Anti-TSLP Fab1

In this Example, anti-TSLP Fab1 was crystallized in free state or in complex with human TSLP, and the corresponding crystal structures were determined. Analysis of anti-TSLP Fab1 binding to human TSLP based on the X-ray data provided insights into the epitope of anti-TSLP Fab1 on human TSLP.

Materials and Methods

Preparation and Purification of Human TSLP and Anti-TSLP Fab1

Anti-TSLP Fab1 were generated by digesting anti-TSLP mAb1 (10.6 mg) with 21 μg of papain for 2 hours at room temperature (RT), in 100 mM Tris (pH 7.0) with 10 mM DTT. The reaction was stopped with 30 μM of the papain inhibitor E64. Anti-TSLP Fab1 was then purified over a 5 mL Lambda Select column, equilibrated with 20 mM sodium phosphate (pH 7.0). The Fab was eluted with 0.1 M citric acid pH 3.0, and the pH of collected fractions was immediately adjusted with 1M Tris pH 8.5 diluted 1:10. LC-MS analysis showed an observed mass of 47107.7 Da which matched the expected amino-acid sequence with the heavy-chain cleaved after Thr228 and bearing a pyroglutamic acid residue at its amino-terminus. For crystallization, the buffer was exchanged to 10 mM Tris-HCl pH 7.4, 25 mM NaCl by repeated concentration-dilution steps using an ultrafiltration device and the sample was finally concentrated to 13 mg/ml of anti-TSLP Fab1.

A construct of human TSLP (Uniprot entry Q969D9; amino-acids 29 to 159) with an N-terminal hexahistidine tag (SEQ ID NO: 40) followed by a PreScission (HRV-3C protease) cleavage site was cloned and expressed in *E. coli* as inclusion bodies. For refolding, 89.4 g of *E. coli* cells were lysed in 715 ml of 50 mM Tris (pH 7.0) with 1 mM EDTA, 6 mM $MgCl_2$, and 0.375M sucrose with an Avestin® high-pressure homogenizer. After 30 minute incubation with 3.7 kU of benzonase, the lysate was centrifuged for 30 minutes at 13,000 rpm with a SS-34 fixed angle rotor. The pellet was resuspended in 387 ml of 100 mM Tris (pH 7.0) with 20 mM EDTA, 0.5M NaCl, 2% Triton X-100 and then centrifuged at 13,500 rpm for 50 minutes. The pellet was again resuspended in 387 ml of 100 mM Tris pH 7.0 with 20 mM EDTA, centrifuged at 13,500 rpm for 30 minutes, and this washing procedure was repeated four times, leading to 13 g of inclusion bodies. The inclusion bodies were then solubilized in 65 ml of 6M guanidine hydrochloride solution with 50 mM potassium acetate (pH 5.0), 5 mM EDTA, and 10 mM TCEP. After 2 hour incubation at room temperature, the sample was centrifuged for 30 minutes at 20,000 rpm (SS-34 fixed angle rotor). The supernatant (70 ml) was diluted to 100 ml with the guanidinium hydrochloride solution described above. Refolding was performed by fast dilution at 4° C. with 10 L of 100 mM Tris (pH 8.25) with 0.5M arginine hydrochloride, 5 mM EDTA, and 1 mM GSH. After dilution, 0.1 mM glutathione disulfide (GSSG) was added and the refolding mix was incubated under slow stirring for 7 days at 4° C. The pH was then adjusted to 5.1 with acetic acid, and 0.1 mM GSSG was added to destroy remaining TCEP. The slightly turbid refolding solution was filtered by a Sartobran 0.65/0.45 μm filter capsule and concentrated with a Pellicon 10 kD cross-flow membrane to 750 ml. The concentrated solution was dialyzed against 10 L of 50 mM sodium acetate pH 5.4. About 550 mgs of refolded TSLP were recovered. LC-MS analysis of the final purified sample confirmed that all disulfide bridges were formed and showed 94% des-Met product (MW=16862.8 Da), and 6% protein with N-terminal methionine. For crystallization with anti-TSLP Fab1, the refolded TSLP sample was used without cleaving the N-terminal tag with the PreScission protease.

To prepare the TSLP-Fab complex, two-fold molar excess of $His_6$-PreSc-TSLP protein ("$His_6$" disclosed as SEQ ID NO: 40) in 25 mM Tris (pH 7.4) with 50 mM NaCl was added to anti-TSLP Fab1, the sample was concentrated by ultrafiltration to about 10 mg/ml, loaded on a SPX-75 size-exclusion chromatography column and eluted isocratically in 10 mM Tris-HCl pH 7.4 with 25 mM NaCl. The peak fraction was concentrated to 9.2 mg/ml by ultrafiltration and submitted to crystallization screening.

Crystallization and X-Ray Data Collection

Crystals were grown in 96-well plates (Innovadyne SD2 plates) by sitting drop vapor diffusion. In detail, 0.2 μl of protein stock was mixed with 0.2 μl of reservoir solution, and the drop was equilibrated against 80 μl of the same reservoir solution at 20° C. The experiments were set up with a Phoenix robotic system (Art Robbins Instruments), stored in a RockImager hotel (Formulatrix) and imaged automatically.

For X-ray data collection, one crystal was directly mounted in a cryo-loop and flash cooled into liquid nitrogen. X-ray data sets were collected at the Swiss Light Source, beamline X10SA, with a Pilatus pixel detector, using 1.00001 Å X-ray radiation. In both cases, 720 images of 0.25° oscillation each were recorded at a crystal-to-detector distance of 345 mm and processed with XDS version Dec. 6, 2010, (Kabsch 1993, J Appl Crystallogr; 26:795-800), as implemented in APRV.

Structure Determination and Analysis

The structure of anti-TSLP Fab1 was determined by molecular replacement with the program Phaser (McCoy et al., 2007, J Appl Crystallogr 40:658-674), using the crystal structure of an anti-CD132 antibody Fab fragment as the starting model. The anti-CD132 antibody Fab was selected on the basis of sequence similarity to anti-TSLP Fab1. The variable and first constant domains were used as independent search models to allow for the variability of the Fab elbow angle. The structure was refined using iterative cycles of model building followed by automated crystallographic refinement with the programs Coot 0.8.0 (Crystallographic Object-Oriented Toolkit; Emsley et al., 2010, Acta Crystallogr Sect D: Biol Crystallogr; 66:486-501) and Autobuster 2.11.5 (Bricogne et al., 2011, BUSTER version 2.11.2. Cambridge, United Kingdom: Global Phasing Ltd.).

The structure of the TSLP-Fab complex was determined by molecular replacement with the program Phaser, using the refined structures of the free anti-TSLP Fab1 and of human TSLP previously determined in house in complex with the Fab fragment of another antibody. Again, the variable and first constant domains of the anti-TSLP Fab1 were used as independent search models. The structure was refined as described before for the free Fab, with Coot 0.8.0 and Autobuster 2.11.5.

Visual inspection of the crystal structures was carried out using the programs Coot (Emsley et al., 2010, Acta Crystallogr Sect D: Biol Crystallogr; 66:486-501) and PyMOL (Molecular Graphics System; DeLano Scientific: Palo Alto, Calif.). The quality of the final refined models was assessed with the programs Coot and PROCHECK v3.3 (Laskowski et al., 1992, J Appl Crystallogr; 26:283-291). Residues of human TSLP that become less accessible to solvent upon binding of the anti-TSLP Fab1 were identified by the program AREAIMOL of the CCP4 program suite (Collaborative Computational Project, Number 4, 1994). Intermolecular contacts were defined using a cut-off distance of 4.0 Å and were identified with the CCP4 program NCONT.

Results

Crystal Structure of the Anti-TSLP Fab1

The free anti-TSLP Fab1 and its complex with human TSLP were crystallized in 96-well plates by the method of vapor diffusion in sitting drops, at 19° C. Interestingly, the two protein samples crystallized under the same crystallization conditions: 0.17M $(NH_4)_2SO_4$, 85 mM sodium acetate pH 5.6, 25.5% PEG MME 2000, 15% glycerol. Crystals appeared after 4-5 weeks and grew to full size within a few days.

The free Fab crystal was in the orthorhombic space group $P2_12_12_1$, with one Fab molecule per asymmetric unit. The crystal of the Fab-TSLP complex was in space group I222, with one complex per asymmetric unit (Table 3). Both crystals diffracted to high resolution, and a complete diffraction data set of good quality and of high redundancy could be collected from each of them (Table 3).

Structure determination by molecular replacement was performed using a previously determined human TSLP structure. Refinement with autobuster led to good refinement statistics and overall geometry (Table 3). Two antibody residues, Asp50L and Asp152L, were Ramachandran outliers in the structure of the free Fab. In addition to these two residues, a third antibody residue, Tyr103H, was also a Ramachandran outlier in the structure of the Fab-TSLP complex. These three residues had well-defined electron-density and are thus genuine geometry outliers. Worthy of note, Asp50L and Tyr103H are CDR residues involved in TSLP binding as described below.

The amino-acid sequences of the anti-TSLP Fab1 heavy chain and light chain are provided in FIGS. 1A and 1B, with the CDRs underlined (as defined by Kabat, 1991, Sequences of proteins of immunological interest, NIH Publication No. 91-3242) and residues located at the antibody-antigen interface labeled with *.

TABLE 3

X-ray data collection and refinement statistics

|  | Free anti-TSLP Fab1 | Fab1 complex with human TSLP |
|---|---|---|
| Data collection |  |  |
| Space group | $P2_12_12_1$ | I222 |
| a, b, c (Å) | 69.05, 72.33, 113.58 | 77.68, 78.46, 233.23 |
| α, β, γ (°) | 90.00, 90.00, 90.00 | 90.00, 90.00, 90.00 |
| Resolution (Å) | 1.85 (1.90-1.85)* | 2.00 (2.05-2.00)* |
| $R_{sym}$ or $R_{merge}$ | 0.044 (1.108) | 0.071 (1.83) |
| I/σ(I) | 21.4 (1.42) | 16.6 (1.14) |
| Completeness (%) | 99.9 (99.8) | 99.9 (99.9) |
| Redundancy | 6.6 (6.2) | 6.6 (6.4) |
| Refinement |  |  |
| Resolution (Å) | 37.00-1.85 | 40.00-2.00 |
| No. reflections | 49,249 | 48,502 |
| $R_{work}/R_{free}$ | 0.201/0.222 | 0.194/0.214 |
| No. atoms |  |  |
| Protein | 3,245 | 4,042 |
| Sulfate ions | 0 | 3 × 5 |
| Waters | 213 | 195 |
| B-factors (Å$^2$) |  |  |
| Fab light-chain (chain L) | 45.7 | 52.4 |

TABLE 3-continued

X-ray data collection and refinement statistics

|  | Free anti-TSLP Fab1 | Fab1 complex with human TSLP |
|---|---|---|
| Fab heavy-chain (chain H) | 48.3 | 48.5 |
| TSLP (chain T) | — | 98.5 |
| Waters (chain W) | 51.4 | 53.1 |
| R.m.s. deviations |  |  |
| Bond lengths (Å)/angles (°) | 0.009/1.05 | 0.010/1.07 |

Note:
*Numbers in brackets correspond to the high resolution shell.

Crystal Structure of the Anti-TSLP Fab1 in Complex with Human TSLP

The amino-acid sequence of recombinant human TSLP used in this example (SEQ ID NO: 38) is provided in FIG. 2. Mature human TSLP started from Tyr29. The construct used here had an N-terminal hexahistidine tag (SEQ ID NO: 40) (residues 15-20) followed by a HRV-3C protease (PreScission) recognition site (residues 21-28) and residues 11-14 resulting from cloning. Asn64 and Asn119 were potential N-linked glycosylation sites; and residues 127-130 constituted the potential furin cleavage site (RRKR, SEQ ID NO: 39). The secondary structure elements are shown below the amino acid sequence: the boxes represent α-helices A, B, C and D, and the thick lines represented the loop regions.

Figure 7:
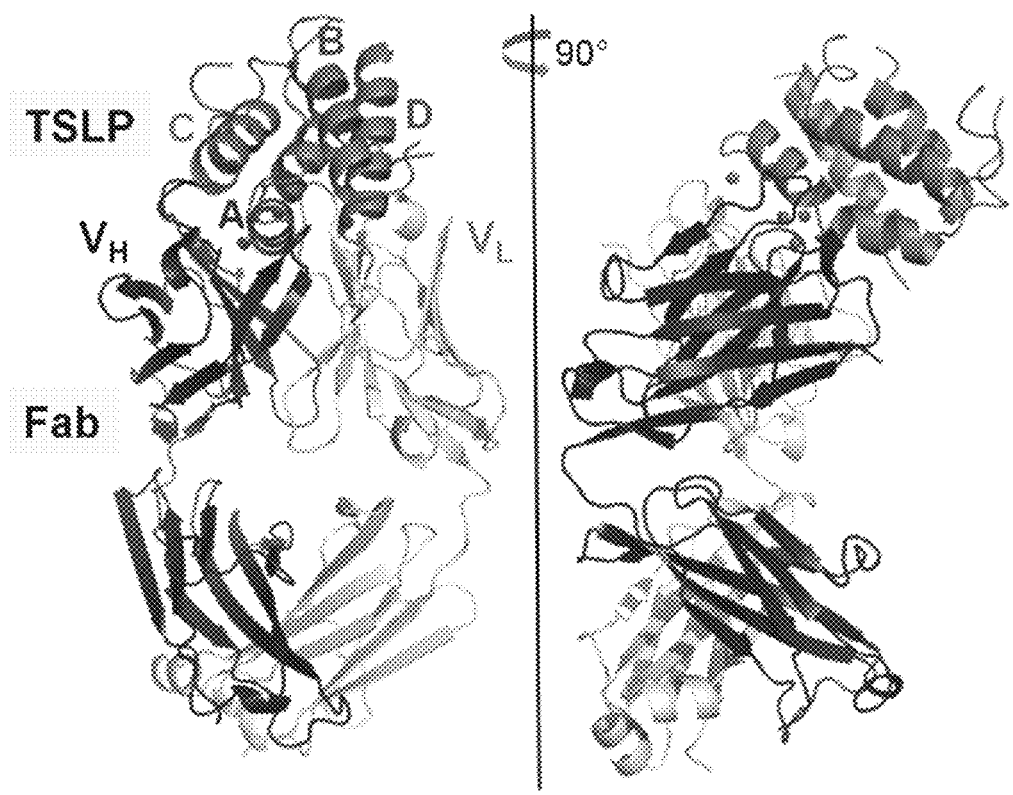
FIG. 7 illustrates an overview of human TSLP in complex with anti-TSLP Fab1. TSLP helices were labelled A to D from N- to C-terminus.

TSLP does not display any significant amino-acid sequence similarity to other members of the IL-2 superfamily of cytokines. Yet, TSLP was folded as a four-helix bundle with up-up-down-down topology, like IL-2, IL-7 and many other cytokines (FIG. 7). Helix $α_A$ possessed a strong kink near its center, around the position of Thr46. Helices $α_B$ and $α_C$ were fairly short with only three turns each; and the C-terminal helix $α_D$ was longer with nearly five turns (FIG. 7). Three disulfides (Cys34-Cys110, Cys69-Cys75, Cys90-Cys137) stabilized this short-chain four-helix bundle. However, the two cross-over connections between $α_A$ and $α_B$, and $α_C$ and $α_D$ were largely disordered and not seen in this crystal structure. Three amino-acids from the $α_B$-$α_C$ loop, and the last five carboxyl terminal residues were also missing in the final refined structure. The potential furin cleavage site and the N-glycosylation sites were located within the missing connections.

An overall view of the three-dimensional structure of the Fab-TSLP complex is shown in FIG. 7.

Anti-TSLP Fab1 bound mainly to helix $α_A$ of TSLP, which ran through the shallow groove lined by H-CDR1 and H-CDR2 on one side, and by H-CDR3 and L-CDR3 on the other side. The pronounced kink of helix $α_A$ occupied the central part of the groove. The flanking helices $α_C$ and $α_D$ and the first four residues of the $α_A$-$α_B$ loop contributed additional contacts to the antibody.

The formation of the Fab-TSLP complex buried approximately 1700 Å$^2$ of combined solvent-accessible surface, with 25 Fab amino acid residues and 25 TSLP amino acid residues experiencing a reduction in their solvent-accessible surface upon complex formation. Among those, 20 Fab residues and 16 TSLP residues (see Table 4) were involved in direct intermolecular contacts, when a 4.0 Å distance cut-off was used. The shape complementarity statistic Sc (Lawrence and Colman, 1993, J Mol Biol; 234:946-50) equaled 0.72, a relatively high value for an antibody-protein complex (Sundberg and Mariuzza, 2003, Adv Protein Chem; 61:119-60). All six CDRs of anti-TSLP Fab1 contributed to binding to TSLP. Furthermore, six well-defined waters located at the antibody-antigen interface mediate binding interactions.

TABLE 4

Epitope and paratope residues

| TSLP epitope | | Anti-TSLP Fab1 paratope | |
|---|---|---|---|
| Structural element | Contact residues | Contact residues | Structural element |
| $\alpha_A$ | Lys38 | Thr28H | H-CDR1 |
| | Ala41 | Tyr32H | H-CDR1 |
| | Leu44 | Tyr103H, Ile102H, Tyr48L | H-CDR3, L-CDR2 |
| | Ser45 | Asp31H, Tyr32H | H-CDR1 |
| | Thr46 | Asp56H | H-CDR2 |
| | Ser48 | Tyr103H | H-CDR3 |
| | Lys49 | Trp33H, Glu101H, Tyr103H, Tyr104H, Tyr105H | H-CDR1, H-CDR3 |
| | Ile52 | Tyr103H, Tyr104H, Tyr31L, Trp92L | H-CDR3, L-CDR1, L-CDR3 |
| | Thr53 | Trp92L | L-CDR3 |
| $\alpha_A$-$\alpha_B$ loop | Ser56 | Trp92L | L-CDR3 |
| | Gly57 | Trp92L | L-CDR3 |
| | Thr58 | Trp92L | L-CDR3 |
| | Lys59 | Gly28L, Ser29L, Lys30L, Tyr31L, Asp50L, Asn65L | L-CDR1, L-CDR2, L-FR3 |
| $\alpha_C$ | Lys101 | Asp56H | H-CDR2 |
| $\alpha_D$ | Gln145 | Tyr103H, Tyr31L | H-CDR3, L-CDR1 |
| | Arg149 | Asn51L, Glu52L | L-CDR2 |

The lists of epitope and paratope residues in direct contact were derived from the final refined coordinates with the CCP4 program NCONT, using a 4.0 Å distance cut-off.

Figure 8:
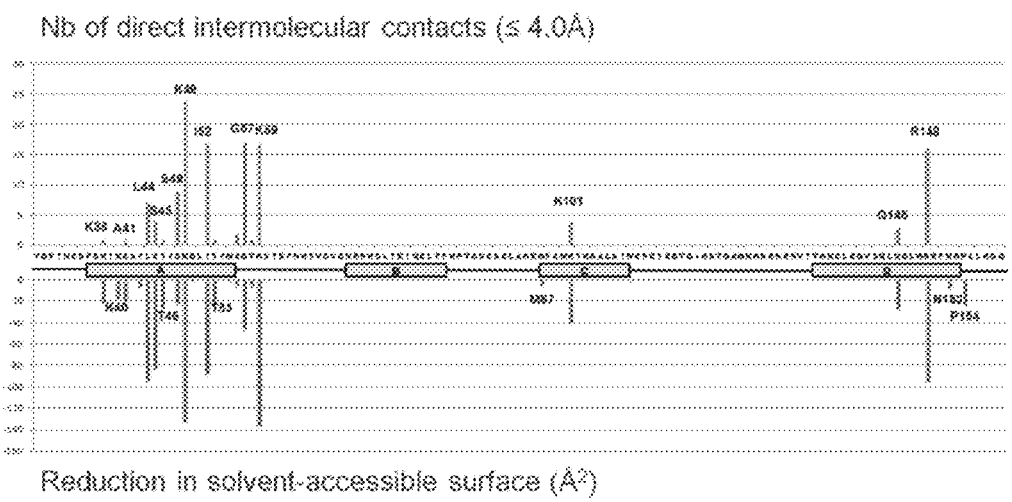
FIG. 8 shows the TSLP epitope targeted by anti-TSLP Fab1. The upper part of the figure shows the number of direct intermolecular contacts between non-hydrogen atoms within 4.0 Å distance, and the lower part shows the reduction in solvent-accessible surface upon complex formation. The amino-acid sequence of the TSLP (SEQ ID NO: 41) is displayed on the horizontal axis.
Figure 9:
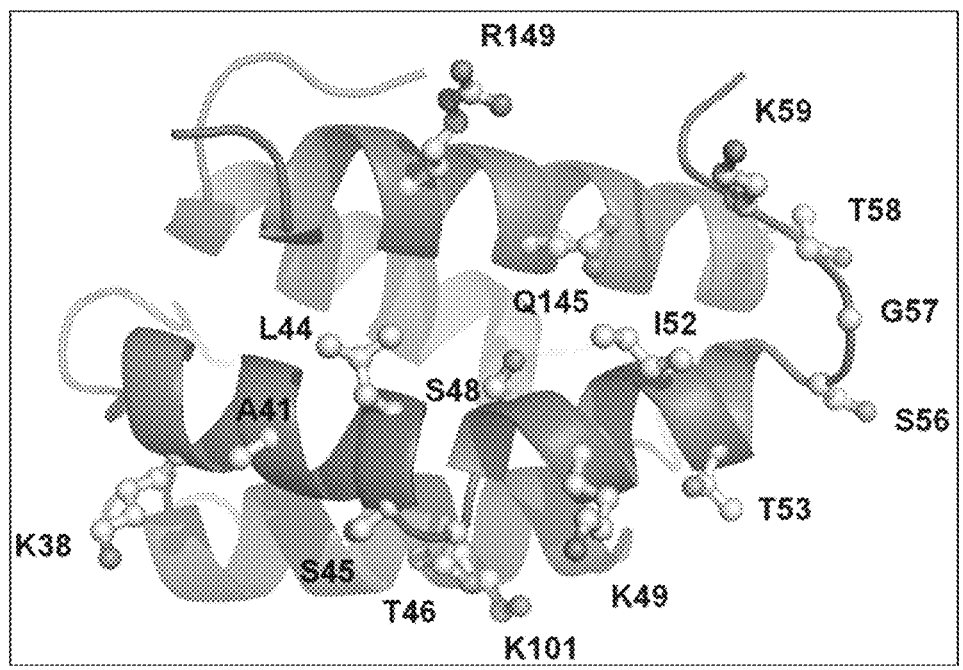
FIG. 9 shows the antibody view of the TSLP epitope. TSLP is shown in ribbon-type cartoon representation. All amino acid residues involved in direct contacts to the Fab1 (4.0 Å distance cut-off) are shown in ball-and-stick representation.

TSLP residues located at the binding interface were identified from the crystallographic coordinates by calculating (i) intermolecular contacts between non-hydrogen atoms less than 4.0 Å, and (ii) the reduction in solvent-accessible surface upon complex formation. The results were shown graphically in FIG. 8, and an antibody view of the TSLP epitope was provided in FIG. 9. As can be seen from these two figures, helix $\alpha_A$, together with the first four residues of the $\alpha_A$-$\alpha_B$ loop, formed the core of the epitope, and contributed 82% of the total number of intermolecular contacts and of the buried solvent-accessible surface on TSLP. Moreover, the vast majority of the key epitope residues were found in this region: Lys49, Ile52, Gly57 and Lys59. In comparison, helices $\alpha_C$ and $\alpha_D$ contributed very few epitope residues: Lys101 ($\alpha_C$), Gln145 and Arg149 ($\alpha_D$).

Figure 10A:
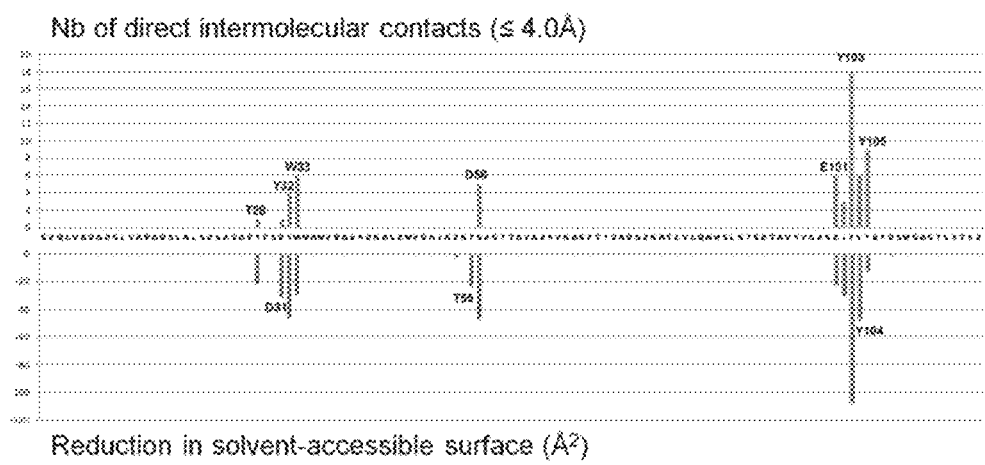
FIGS. 10A and 10B show the heavy-chain (SEQ ID NO: 42) (A) and light chain (SEQ ID NO: 43) (B) paratope of anti-TSLP Fab1. The upper part of the figure shows the number of direct intermolecular contacts (≤4.0 Å) between non-hydrogen atoms, the lower part shows the reduction in solvent-accessible surface upon complex formation. The amino-acid sequence of the heavy- or light-chain variable domain is displayed on the horizontal axis.
Figure 10B:
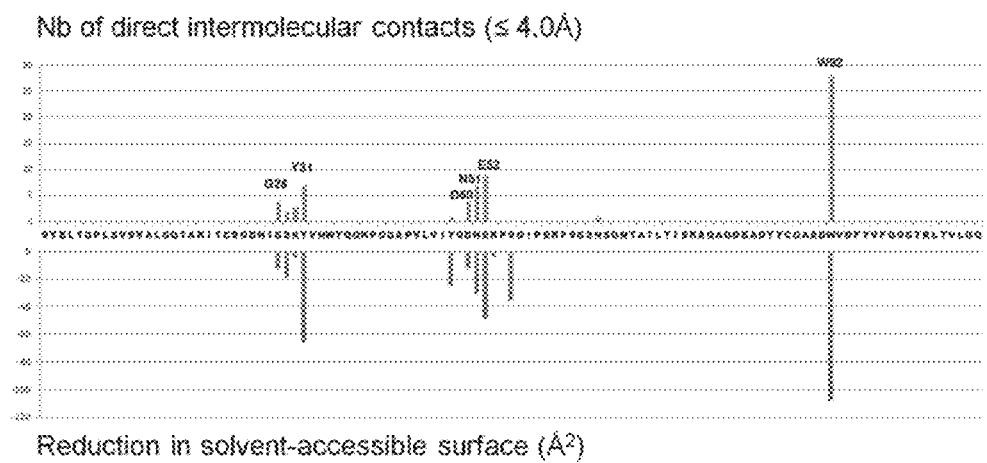

All six complementarity-determining regions (CDRs) of anti-TSLP Fab1 contributed to the binding interface, as evidenced by a reduction in their solvent-accessible surface upon antigen binding and their contributions to direct intermolecular contacts (FIGS. 10A and 10B). In addition, Asn65L of the third framework region of the light-chain (L-FR3) was also located at the antigen-binding interface, but it only made a weak (3.6 Å) H-bonded interaction to Lys59 of TSLP.

The H-CDR3 loop played a particularly important role. Glu101H made the critical salt-bridge interaction with Lys49 of TSLP, and the three consecutive tyrosines located at the tip of the loop, Tyr103H, Tyr104H and Tyr105H, contributed collectively 58% of the contacts made by the whole heavy-chain. Trp33H of H-CDR1 and Asp56H of H-CDR2 were also important paratope residues, which contributed to the binding of Lys49 and Lys101 of TSLP, respectively.

Trp92L was the only L-CDR3 residue that made direct contacts with the antigen. This residue is located at the tip of L-CDR3 and it did not adopt a defined conformation in the crystal structure of the free anti-TSLP Fab1. In the TSLP complex, however, the side-chain had well-defined electron-density, and made extensive contacts to the $\alpha_A$-$\alpha_B$ loop, its contribution amounting to 42% of the contacts made by the whole light-chain. Asp50L of L-CDR2 and Tyr31L of L-CDR1 were two other important paratope residues provided by the light-chain. The former made a very short (2.8 Å) electrostatic interaction with Lys59 of TSLP. The latter contributed binding interactions with Ile52, Lys59, and Gln145 of TSLP, and also stabilized the bound conformation of the H-CDR3 loop through π-π interactions with Tyr103H and Tyr104H.

Mode of Action of Anti-TSLP Fab1

TSLP signaling requires the assembly of a ternary complex comprising TSLP, the cognate TSLPR chain and the shared IL-7Rα chain. The formation of the TSLP-TSLPR binary complex is a prerequisite for the recruitment of the IL-7Rα chain. Human TSLP-Fab1 complex was superimposed onto the mouse TSLP-TSLPR-IL-7Rα ternary complex, based on all TSLP Cα atoms. The structural overlay demonstrated that the anti-TSLP Fab1 blocked TSLP binding to both TSLPR and IL-7Rα. Helix $\alpha_A$ of TSLP was the central element of anti-TSLP Fab1 epitope (FIG. 11B), and this helix also played a central role in binding to both TSLPR and IL-7Rα (FIG. 11A). In addition, helix $\alpha_C$ was engaged in IL-7Rα binding and helix $\alpha_D$ was part of the TSLPR binding interface. Since these two helices also contributed to anti-TSLP Fab1 epitope, the steric interference between anti-TSLP Fab1 and the two receptor chains was extensive. The antibody light-chain overlapped extensively with the D2 domain of the TSLPR, while the heavy-chain overlaped with the IL-7Rα D2 domain and also with some of the cytokine binding loops of the D1 domain (FIG. 11C). The data demonstrated that anti-TSLP Fab1 neutralized TSLP by scavenging the cytokine and preventing its binding to the TSLPR receptor, thus blocking the formation of the high affinity signaling complex with IL-7Rα.

In summary, the high resolution crystal structures of the anti-TSLP Fab1 in the free state or in complex with refolded recombinant human TSLP were determined. Anti-TSLP Fab1 was found to bind mainly to helix αA (amino acid residues Lys 38 to Thr 53) of human TSLP, with few but important contributions from helices αC (Lys101) and αD (Gln145, Arg149) and from the αA-αB loop (amino acid residues Ser 56 to Lys 59). A structural overlay of human TSLP in complex with anti-TSLP Fab1 onto the published mouse TSLP complex with the IL-7RA and TSLPR extracellular domains showed that anti-TSLP Fab1 competes with both IL-7RA and TSLPR for TSLP binding. Anti-TSLP Fab1-bound TSLP cannot bind TSLPR and the recruitment of IL7Rα receptor is also inhibited due to extensive steric hindrance between the Fab and the IL-7α receptor.

Example 10: Spray-Drying Process and Formulation of Anti-TSLP Fab1

Spray-Drying Equipment and Operations

A custom-built spray dryer was used to spray dry a feedstock. The spray-dryer configuration comprises a single-nozzle twin-fluid atomizer, a drying chamber, a cyclone, an adaptor, an isolation valve, and a 1-liter collector in a temperature-controlled jacket. In the embodiments described herein, the spray spray-drying process may include an atomization process, a drying process, and a particle collection process.

An exemplary atomization process may include the following steps: (A1) a formulated feedstock fluid may be fed through a peristaltic pump (Watson Marlow) at a controlled flow rate to a single-nozzle, air-assisted atomizer mounted in the spray dryer; (A2) compressed dry air with a controlled flow rate is fed to a concentric, convergent gas nozzle; and (A3) expansion of the air at the nozzle tip atomizes the feedstock stream into a fine droplet spray.

The drying process may include the following steps: (B1) drying air heated with an electrical heater is fed to the drying chamber at a set temperature and a controlled flow rate; (B2) the hot drying air interacts with the fine droplet spray from Step A3. The solvent (water) in the droplets evaporates, resulting in solid particles; and (B3) particles and solvent vapor/air exit the drying chamber at a pre-determined temperature.

The particle collection process may include the following steps: (C1) particles and non-solvent vapor/air from Step B3 enter the cyclone at high tangential speed; (C2) particles are separated from the air mixture by centrifugal force and are collected at the bottom of the cyclone in a temperature-controlled collection vessel; and (C3) the exhaust non-solvent vapor/air passes through a filter and vents to the atmosphere inside the isolator.

Process and Formulation of Respirable Powders of Anti-TSLP Fab1

This part provides a formulation and spray-drying process used to prepare respirable powders comprising particles of anti-TSLP Fab1 formulated with various excipients. This involved spray drying a single-phase, aqueous feedstock comprising the protein (anti-TSLP Fab1) and excipients that principally function either as dispersibility-enhancing agents (e.g., trileucine) or glass-forming agents (e.g., saccharides, buffer salts). The pH of the feedstock was controlled with a histidine-HCl buffer at a target pH of pH5.0-pH5.5. Through application of particle engineering principles, the excipients and composition were selected to create a powder that comprised rugous particles—each with a core of protein stabilized within a glassy matrix surrounded by a shell of hydrophobic excipient that improved powder dispersibility and protected the active agent.

TABLE 5

Anti-TSLP Fab1 Formulations

| Lot # | Anti-TSLP Fab1 % w/v | Histidine % w/v | Trehalose % w/v | Mannitol % w/v | Trileucine % w/v |
|---|---|---|---|---|---|
| 569-38-01 | 80 | 20 | 0 | 0 | 0 |
| 569-38-02 | 90 | 10 | 0 | 0 | 0 |
| 569-38-03 | 60 | 10 | 30 | 0 | 0 |
| 569-38-04 | 60 | 5 | 20 | 5 | 10 |
| 569-38-05 | 40 | 5 | 35 | 0 | 20 |
| 569-38-06 | 40 | 5 | 30 | 5 | 20 |

Figure 12:
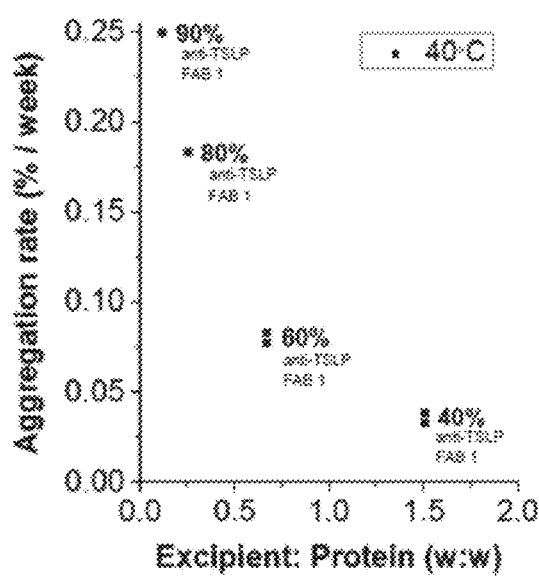
FIG. 12 is a scatter plot illustrating formulations at higher excipient:protein ratios improve the physicochemical stability of anti-TSLP Fab1, as shown by the reduction in the protein aggregation rate.

FIG. 12 shows formulations with higher excipient: protein ratio improved the physicochemical stability of anti-TSLP Fab1 and reduced in the aggregation rate of anti-TSLP Fab1.

PulmoSol Formulation Comprising Anti-TSLP Fab1

This part provides the composition of feedstocks formulated at different total solids concentration and trileucine content to increase the manufacturing throughput and to optimize the shell formation. A high solids concentration increases the powder production throughput. In this example, the TSLP Fab1 content is fixed at 50%, with one exception, compared with the previous example.

TABLE 6

Formulations comprising anti-TSLP Fab1 and trileucine

| Lot # | Solid content % w/v | Anti-TSLP Fab1 % w/w | Histidine % w/w | Trileucine % w/w | Trehalose % w/w | Molar ratio Sugar:Drug |
|---|---|---|---|---|---|---|
| 728-06-01 | 1.5% | 50.0% | 5.89% | 20.0% | 24.1% | 70.4 |
| 728-06-02 | 2.0% | 50.0% | 5.89% | 15.0% | 29.1% | 85.0 |
| 728-06-03 | 2.5% | 50.0% | 5.89% | 10.0% | 34.1% | 99.6 |
| 728-06-04 | 2.0% | 50.0% | 5.89% | 10.0% | 34.1% | 99.6 |
| 728-06-05 | 1.5% | 40.0% | 4.71% | 20.0% | 30.3% | 110.6 |

Formulations Comprising Anti-TSLP Fab1 and 15% Trileucine

This part highlights several formulations designed to accommodate the limited aqueous solubility of trileucine while maintaining an acceptable pH of the feedstock and resulting particles. Here, the trileucine was dissolved in aqueous HCl and back-titrated using various basic media to attain the target pH of the feedstock solution (pH5.0-pH5.5). Approximately, a 1:1 molar ratio of the HCl to trileucine was required to fully dissolve the trileucine.

TABLE 7

Formulations comprising anti-TSLP Fab1 and 15% trileucine

| Batch No. | ANTI-TSLP FAB1 % w/v | Histidine % w/w | Trehalose % w/w | Trileucine % w/w | Acid, HCl % w/w | Base % w/w | |
|---|---|---|---|---|---|---|---|
| 569-60-01 | 50.0% | 5.64% | 26.8% | 15.0% | 2.56% | N/A | |
| 569-60-02 | 50.0% | 5.64% | 19.4% | 15.0% | 2.56% | Histidine | 7.40% |
| 569-60-03 | 50.0% | 5.64% | 24.1% | 15.0% | 2.56% | KOH | 2.69% |
| 569-60-04 | 50.0% | 5.64% | 26.8% | 15.0% | 2.56% | NH$_4$OH | 2.70% |

Example 11: Binding Affinities of the Anti-TLSP Fab1 to Human and Cyno TSLP Proteins Determined by Solution Equilibrium Titration (SET)

Solution equilibrium titration (SET) measurements were carried out to determine the binding affinities of anti-TSLP Fab1 to human and cyno TSLP proteins. The Fab was incubated at a constant concentration with serial dilutions of the respective antigens. The binding affinity was extracted from a competition curve which was generated by plotting the read-out of the concentration of unbound antibody against the applied antigen concentration. Anti-TSLP Fab1 showed binding affinities in the low picomolar (pM) range for all human and cyno TSLP proteins.

Assay Procedure

Twenty-two serial 1.6" dilutions of the human TSLP (produced in HEK cells) and cyno TSLP antigens were prepared in sample buffer and a constant concentration of Fab1 was added. A volume of 60 µl/well of each antigen-Fab mix was distributed in duplicates to a 384-well polypropylene microtiter plate (MTP). Sample buffer served as negative control and a sample containing only Fab1 as positive control (Bmax). The plate was sealed and incubated overnight (o/n, at least 16 h) at room temperature (RT) on a shaker.

A 384-well MSD array MTP was coated o/n at 4° C. with 30 µl/well of hsTSLP (produced in *E. coli*) diluted in PBS at 5 µg/ml, then washed three times with 70 µl/well of wash buffer and blocked with 50 µl/well of blocking buffer for 1 h at RT on a shaker. After washing, a volume of 30 µl/well of the equilibrated antigen-Fab mix was transferred from the polypropylene MTP to the coated MSD plate and incubated for 20 min at RT.

After an additional wash step, 30 µl of sulfo-tagged detection antibody diluted in sample buffer at 1.8 µg/ml were added to each well and incubated for 30 min at RT on a shaker. The MSD plate was washed and 35 µl/well of 1×MSD read buffer were added and incubated for 5 min at RT. ECL signals were generated and measured by the MSD Sector Imager 6000.

Three independent experiments were performed for each antigen and demonstrated stable assay conditions. From these experiments the mean values for the dissociation equilibrium constants $K_D$ and standard deviations were calculated as shown below.

TABLE 8

Affinity Constants ($K_D$) for Fab1 binding to human and cyno TSLP proteins

| FAB | Antigen | $K_D$ (pM) | No of experiments |
| --- | --- | --- | --- |
| Fab1 | human TSLP (HEK) | 5.0 ± 2.0 | 3 |
| Fab1 | cyno TSLP | 1.4 ± 0.6 | 3 |

Example 12: Two Week Inhalation Dose Range Finding Study in the Cynomolgus Monkey In this non-GLP study, the objective was to determine the potential toxicity of Fab1, an anti-thymic stromal lymphopoietin (TSLP) Fab, when administered to cynomolgus monkeys by the inhalation route once daily for 14 days or, as a single dose IV injection on Day 1, followed by a 13 day non-dosing period and a single inhaled dose on Day 15. In addition, the pharmacokinetic/pharmacodynamic (PK/PD) profile and immunogenicity (IG) of Fab1 were investigated.

The study was conducted as two separate components of the single study.

Inhalation only: Fab1 PulmoSol powder, 39.7% Fab1 in PulmoSol, was administered by inhalation to 3 groups (3 males/group) of cynomolgus monkeys at targeted daily doses of 1.0, 10.0 and 20.0 mg Fab1/kg/day. Another group of monkeys (2 males) received Placebo PulmoSol powder and served as a control. An additional single male animal received air only and acted as an air control. Fab1 PulmoSol and Placebo PulmoSol aerosols were generated using a rotating brush generator device (RBG1000). The animals were exposed to an aerosol of Fab1 PulmoSol powder (Groups 3 to 5) or Placebo PulmoSol powder (Group 2) for a target 60 minutes once daily for 14 days, using a close fitting oro-nasal mask. The single Group 1 male animal was exposed to filtered dry air only for the same target duration using the same equipment set up. The overall administered mean aerosol concentrations of Fab1 were 0.036, 0.31 and 0.66 mg/L for Groups 3, 4 and 5, respectively. The overall mean (estimated total) delivered doses were 1.1, 9.6 and 19.9 mg Fab1/kg/day for Groups 3, 4 and 5, respectively. The mass median aerodynamic diameter (MMAD) confirmed that the generated Fab1 aerosols were respirable to the monkeys and that acceptable pulmonary deposition would be achieved for the test species.

Intravenous/Inhalation: Fab1 was administered to a group of 3 male animals (Group 6) as a single intravenous bolus injection via the saphenous vein on Day 1. The target dose was 1 mg Fab1/kg. The animals were then allowed a 13 day non-dosing period before being administered with Fab1 PulmoSol powder, 39.7% Fab1 in PulmoSol, by inhalation on Day 15. The target dose was 20 mg Fab1/kg. Fab1 PulmoSol aerosol was generated using a rotating brush generator device (RBG1000). The animals were exposed to an aerosol of Fab1 PulmoSol powder for a target 60 minutes on a single occasion, using a close fitting oro-nasal mask. Animals were then retained for 6 days before being euthanized on Day 21. The overall administered mean aerosol concentration of Fab1 was 0.60 mg/L. The overall mean estimated total delivered dose was 16.3 mg Fab1/kg/day. The mass median aerodynamic diameter (MMAD) confirmed that the generated Fab1 aerosol was respirable to the monkeys and that acceptable pulmonary deposition would be achieved for the test species.

The following parameters and endpoints were evaluated in this study: clinical signs, body weight, body weight changes, clinical pathology parameters (haematology, coagulation and clinical chemistry), bioanalysis for Fab1 and TSLP concentrations and toxicokinetic parameters (serum, bronchoalveolar lavage (BAL) fluid, lung tissue extracts), anti-Fab1 antibodies (serum and BAL fluid), gross necropsy findings, organ weights and histopathologic examinations (Groups 1 to 5 only).

The administration of Fab1 for 14 days, via inhalation dosing, resulted in apparent changes within the nasal cavity (increased mucous cells within the respiratory epithelium), lungs (diffuse alveolar macrophages accumulation, increased bronchiolo-alveolar lymphoid cellularity and mixed alveolar inflammatory-cell infiltration) and bronchial lymph node (increased general cellularity) of male cynomolgus monkeys. These changes were evident amongst animals from all treated groups. The severity of the findings was minimal to mild in all cases and the observations were not considered adverse.

Overall, exposure to Fab1 was demonstrated in all animals treated with Fab1 based on concentration data in serum, bronchoalveolar (BAL) and lung extracts; whereas no Fab1 was detected in any of the samples from the air or Placebo PulmoSol control animals. Bioavailability was calculated to be approximately 0.2% after the inhalation dose on Day 15. Anti-Fab1 antibodies in serum were detected only in one Group 4 animal at pre-dose on Day 1 and one Group 5 animal at Day 14, but the observed signals were considered not to have apparent impact on the exposure to Fab1 in these animals. Overall no overt immunogenicity to Fab1 was detected in the study. Total TSLP was not detected in serum, BAL or lung tissue in the majority of the samples, except for some very low signals detected in the first wash samples (collected during the BAL procedure from three Fab1-treated animals).

In conclusion, administration of Fab1 to 3 cynomolgus monkeys as a single intravenous bolus injection on Day 1, followed by a 13 day non-dosing period and a single inhaled dose on Day 15 resulted in no adverse effects. Inhalation administration of Fab1 to the cynomolgus monkey for 14 days was associated with apparent changes within the nasal cavity, lungs and bronchial lymph node of animals from all treated groups. The severity of the findings was minimal to mild in all cases and the observations were considered not to be adverse. All animals receiving Fab1 were systemically exposed to the test item.

Example 13: Thirteen Week Inhalation Toxicity Study in Cynomolgus Monkeys

The objectives of this study were to determine the potential toxicity of Fab1, an anti-thymic stromal lymphopoietin (TSLP) Fab, when given by the inhalation route once daily for at least 92 consecutive days (13 weeks) to cynomolgus monkeys, and to evaluate the potential reversibility of any findings following a 42 day (6 week) recovery period. In addition, the toxicokinetic and immunogenic characteristics of Fab1 were determined.

Fab1 PulmoSol powder was administered by inhalation to 3 groups (3/sex/group) of cynomolgus monkeys at target daily doses of 3, 10 and 22 mg/kg/day. Another group of monkeys (3/sex) received placebo PulmoSol powder and served as controls. An additional 2 animals (2/sex) in the Placebo and 22 mg/kg/day groups were maintained on study for a 6 week recovery period. Fab1 PulmoSol and placebo PulmoSol aerosols were generated using a rotating brush generator device (RBG1000). The animals were exposed to an aerosol of Fab1 PulmoSol powder (Groups 2 to 4) or placebo PulmoSol powder (Group 1) for a target 60 minutes once daily for at least 92 consecutive days, using a close-fitting oro-nasal mask.

The following parameters and end points were evaluated in this study: clinical signs, body weights, body weight changes, ophthalmic examinations, neurological exams (including respiratory rate), electrocardiology, clinical pathology parameters (haematology, coagulation, clinical chemistry and urinalysis), peripheral blood lymphocyte immunophenotyping (flow cytometry), immune function (T cell dependent antibody response (TDAR) to keyhole limpet hemacyanin (KLH)), bioanalysis for Fab1 concentrations and toxicokinetic parameters (serum and lung tissue extracts), anti-Fab1 antibodies (serum), gross necropsy findings, organ weights, and histopathologic examinations.

The overall administered mean aerosol concentrations of Fab1 were 0.10, 0.33 and 0.72 mg/L for Groups 2, 3 and 4, respectively. The estimated overall mean achieved total delivered doses (sexes combined) were 3.0, 10.1 and 22.2 mg/kg/day Fab1 for Groups 2, 3 and 4, respectively. The mass median aerodynamic diameter (MMAD) confirmed that the generated Fab1 aerosols were respirable to the monkeys and that acceptable pulmonary exposure would be achieved for the test species.

There were no overt test item-related effects observed for any of the cardiovascular parameters following administration of Fab1 at achieved doses of 3, 10 or 22 mg/kg/day.

Results for the immune function (TDAR) investigations indicated a trend toward decreased anti-KLH IgG antibody levels at achieved doses of ≥10.1 mg/kg/day. At the last sampling time point (study day 78), decreased anti-KLH IgG and IgM antibody levels were noted at achieved doses ≥3 mg/kg/day. This effect was most pronounced in the males at all timepoints and in the females on Day 78, but less prominent in females on other sampling occasions. The trend toward a decrease in anti-KLH response was not considered adverse. The anti-KLH IgG and IgM antibody levels in Group 4 (22.2 mg/kg/day) recovery animals were higher on all occasions when compared to the concurrent control (Group 1) recovery values and similar to the control (Group 1) main study results, supportive of a recovery of the decreased anti-KLH antibody response. The administration of Fab1 for at least 92 days, via inhalation dosing, resulted in increased cellularity of the lymphoid tissue within the lungs at achieved doses 3 mg/kg/day. The severity of the finding was minimal to mild in all cases and considered not to be adverse. After a 6 week recovery period, the finding was absent in 2/4 (50%) of the recovery animals and observed in 2/4 (50%) of the high dose animals at minimal severity. The same finding was also present in one control recovery female (mild) confirming that this change may occasionally be found sporadically among control animals. Fab1 was not detected in any of the serum or lung tissue samples from the placebo PulmoSol control group (Group 1) animals. Overall, exposure to Fab1 was demonstrated throughout the dosing period in animals treated with Fab1, with a dose-related increase in both serum and lung tissue. Systemic exposure in serum was also demonstrated during recovery for up to 14-28 days post the last dose on day 92, whilst the lung tissue concentrations were undetectable in all recovery animals by the time of necropsy on Day 135 (42 days post the last dose). There was a marked accumulation in serum exposure to Fab1 from Study Day 1 to Study Day 91 following repeated daily doses across all dose groups. No apparent gender-related differences in exposure were observed. Low but detectable anti-drug antibodies (ADA) signals were observed in two placebo PulmoSol control animals at both pre-dose baseline and post-dose timepoints, likely due to pre-existing antibodies that were not specific for Fab1. ADA signals were not detected in any other control animals. All Fab1-treated animals developed post-dose signals of ADAs as early as study Day 28 onwards. The strong ADA signals in three animals were apparently associated with loss of exposure to Fab1 in serum, but lung exposure to Fab1 was still demonstrated in these animals at the time of necropsy (1~6 hours post the last dose). in conclusion, inhalation administration of Fab1 to the cynomolgus monkey for 13 weeks was well tolerated at respirable achieved dose levels up to 22.2 mg/kg/day. All animals receiving Fab1 were confirmed to have exposure to Fab1 both systemically and in the lung. Anti-Fab1 antibodies were present in all treated animals as early as Day 28 onwards and were associated with much lower exposure in 3 individuals compared to the rest of the treated animals, Microscopic evaluation confirmed. increased cellularity of lung lymphoid tissue for the majority of all Fab1 treated animals, which was observed in 50% of the high-dose recovery animals following a 6-week recovery period. The severity of the finding was minimal to mild in all cases and was considered to be non-adverse.

Example 14: Preparation of Simple Spray-Dried Formulations of a Monoclonal Antibody Fragment The monoclonal antibody fragment Fab1 described herein has a molecular weight of 46.6 kDa. Dry powder formulations are described for local lung delivery in the treatment of asthma. In this context, the use of the term "simple" refers to formulations of active pharmaceutical ingredient (Fab1) and buffer only.

A series of simple antibody formulations comprising 89.5% active pharmaceutical ingredient and 10.5% histidine buffer were manufactured from feedstocks comprising various ethanol/water solvent compositions (Table 9). The ethanol content was varied between 5% and 20% w/w. The feedstocks were spray-dried on the NSD spray-dryer with an inlet temperature of 105° C., an outlet temperature of 70° C., a drying gas flow rate of 595 L/min, an atomizer gas flow rate of 20 L/min, a liquid feed rate of 8.0 mL/min, and an ALR of $2.5 \times 10^3$ v/v. The solids content was fixed at 2% w/v.

TABLE 9

Impact of process parameters on micromeritic properties of simple antibody formulations comprising 89.5% API in histidine buffer.

| Lot # | API (% w/w) | Trileucine (% w/w) | Solids (% w/v) | EtOH (% w/w) | PPSD (μm) ×10 | PPSD (μm) ×50 | PPSD (μm) ×90 | Tapped Density (g/cm³) |
|---|---|---|---|---|---|---|---|---|
| 761-22-07 | 89.5 | 0 | 2 | 0 | 0.55 | 1.34 | 3.24 | 0.347 |
| 761-02-09 | 89.5 | 0 | 2 | 5 | 0.66 | 1.93 | 5.64 | 0.178 |
| 761-02-06 | 89.5 | 0 | 2 | 10 | 0.73 | 2.48 | 7.19 | 0.142 |
| 761-02-07 | 89.5 | 0 | 2 | 20 | 0.69 | 1.94 | 6.04 | 0.135 |

Example 15: Micromeritic Properties of Simple Spray-Dried Formulations of Antibody The micromeritic properties of the spray-dried antibody formulations of Example 14 are presented in Table 9. All of the simple formulations comprising just API and buffer, produced particles with a smooth particle surface (i.e., no surface corrugation). The addition of small amounts of ethanol to the aqueous feedstock decreased the bulk and tapped density of the powders, (observed also for insulin formulations). The particles were also relatively large in terms of their primary particle size distribution (PPSD).

Example 16: Aerosol Performance of Simple Spray-Dried Formulations of Antibody The DD and TLD determined for the powders delineated in Example 15 are presented in Table 10. The primary particles had a calculated median aerodynamic diameter, $D_a$, between 0.71 and 0.93 μm (calculated from the tapped density and ×50 measurements using the equation: $d_a = d_g \sqrt{\rho_p}$).

The Concept1 dry powder inhaler is a low resistance capsule-based device (R=0.07 cm $H_2O)^{1/2}$/(L/min)).

TABLE 10

Aerosol performance of simple antibody formulations. Aerosol performance was assessed with the Concept1 Inhaler (20 mg fill mass) at a flow rate of 90 L/min and a total volume of 2 L (n = 5).

| Lot # | Tapped Density (g/cm³) | ×50 (μm) | $D_a$ (calc) (μm) | Morphology | DD (% ND) | TLD (% DD) |
|---|---|---|---|---|---|---|
| 761-22-07 | 0.347 | 1.34 | 0.79 | Smooth | 64.9 | 65.0 |
| 761-02-09 | 0.178 | 1.93 | 0.81 | Smooth | 77.0 | 57.1 |
| 761-02-06 | 0.142 | 2.48 | 0.93 | Smooth | 81.2 | 43.7 |
| 761-02-07 | 0.135 | 1.94 | 0.71 | Smooth | 74.3 | 57.7 |

It is clear from the data in Table 10 that decreasing density alone is insufficient to enable formation of particles that effectively bypass deposition in the mouth-throat. In order to achieve this, particle morphology must be modified to increase surface rugosity (corrugation), and decreases in primary particle size would be desirable.

It is interesting to note that while peptides and small proteins naturally adopt a corrugated morphology in the absence of a shell-forming excipient, formulation of the antibody requires the addition of a shell-forming excipient to enable formation of corrugated particles. In this regard, the shell-forming excipient and addition of ethanol perform similar functions in modifying the wall thickness and density of the spray-dried particles. Hence the impact of addition of ethanol is smaller in the presence of a shell former.

Example 17: Preparation and Micromeritic Properties of Platform Spray-Dried Formulations of Antibody In this series of spray-dried powders, the spray-drying conditions were held constant, and the impact of the addition of a shell-forming excipient (i.e., trileucine, 0-15% w/w) was assessed for antibody formulations. These formulations also contain trehalose as a glass-former (about 29-44% w/w depending on trileucine content) and histidine buffer (5.9% w/w, pH 5.0).

Powders were spray-dried on the custom NSD spray dryer with an inlet temperature of 105° C., an outlet temperature of 70° C., a drying gas flow rate of 595 L/min, an atomizer gas flow rate of 25 L/min, a liquid feed rate of 10.0 mL/min, and an ALR of $2.5 \times 10^3$ v/v. The solids content was held constant at 2% w/w. All of the powders had a corrugated morphology with the exception of lot 761-02-12, which was spray dried in the absence of a shell former and produced smooth particles similar to those observed in Example 16.

Results are shown in Table 11. In some embodiments, the dry powder formulation of the present invention comprises core-shell particles comprising: a shell-forming excipient, and a core comprising the API, glass-forming excipients, and a buffer, sometimes also referred to herein as the platform formulation.

TABLE 11

Impact of process parameters on micromeritic properties of 'platform' antibody formulations comprising 50.0% w/w API, 5.9% histidine buffer, trehalose and trileucine.

| Lot # | API (% w/w) | Trileucine (% w/w) | EtOH (% w/w) | PPSD (µm) ×10 | ×50 | ×90 | Tapped Density (g/cm³) |
|---|---|---|---|---|---|---|---|
| 728-06-04 | 50.0 | 10.0 | 0 | 0.55 | 2.28 | 5.14 | 0.366 |
| 728-06-02 | 50.0 | 15.0 | 0 | 0.64 | 2.06 | 4.83 | 0.197 |
| 761-02-12 | 50.0 | 0.0 | 10 | 0.48 | 1.60 | 4.87 | 0.158 |
| 761-22-06 | 50.0 | 5.0 | 10 | 0.50 | 1.63 | 3.85 | 0.268 |
| 761-02-11 | 50.0 | 10.0 | 10 | 0.63 | 2.25 | 5.75 | 0.176 |
| 761-02-10 | 50.0 | 15.0 | 10 | 0.67 | 2.30 | 5.27 | 0.112 |

Example 18: Aerosol Performance of 'Platform' Spray-Dried Formulations of Antibody with Varying Trileucine Content The DD and TLD determined for the powders described in Example 17 are presented in Table 12.

TABLE 12

Impact of process parameters on micromeritic properties and aerosol performance of platform antibody formulations. Aerosol performance was assessed with the Concept1 Inhaler (20 mg fill mass) at a flow rate of 90 L/min and a total volume of 2 L (n = 5).

| Lot # | Ethanol/ Solids | Tapped Density (g/cm³) | ×50 (µm) | $D_a$ (calc) (µm) | Morphology | DD (% ND) | TLD (% DD) |
|---|---|---|---|---|---|---|---|
| 728-06-04 | 0 | 0.366 | 2.28 | 1.38 | Corrugated | 90.0 | 83.3 |
| 728-06-02 | 0 | 0.197 | 2.06 | 0.91 | Corrugated | 90.0 | 80.0 |
| 761-02-12 | 5 | 0.158 | 1.60 | 0.64 | Smooth | 69.0 | 66.2 |
| 761-22-06 | 5 | 0.268 | 1.63 | 0.84 | Corrugated | 89.2 | 79.1 |
| 761-02-11 | 5 | 0.176 | 2.25 | 0.94 | Corrugated | 92.3 | 84.8 |
| 761-02-10 | 5 | 0.112 | 2.30 | 0.77 | Corrugated | 93.1 | 83.0 |

Significant improvements in DD and TLD are observed for antibody formulations with a corrugated particle morphology. In embodiments of the invention, the desired corrugated morphology results from the presence of the shell-forming excipient trileucine on the particle surface.

In embodiments of the invention, physicochemical properties of the material on the surface of the particles influence particle morphology. For large proteins (such as certain proteins above 20,000 Daltons) a shell forming excipient such as trileucine is preferred to achieve the desired morphology. In embodiments of the invention particles forming the formulation and composition have a corrugated morphology to reduce cohesive forces between particles, such that the size of the agglomerates is small enough that the agglomerates are respirable.

When ethanol is added, it lowers the particle density of (otherwise) corrugated particles by decreasing the wall thickness. This, in turn, lowers the tapped density enabling smaller primary particles in accord with desired aerodynamic properties. In some embodiments particles should have a lowered density, such that the primary particles, and the agglomerates, are respirable.

Significant reductions in tapped density are noted for paired formulations 728-06-04 and 761-02-11 and 728-06-02 and 761-02-10 when the ethanol content is increased from 0% to 10% w/w. For the specific formulations in this Example, addition of 10% ethanol alone did not afford the target improvement in aerosol performance over what is provided by the shell-forming excipient. The TLD is excellent (>80% of the DD), but remains below the desired target of 90% w/w of the DD, in large part because the particles are too large and dense. For the corrugated particles the calculated primary aerodynamic diameter, $D_a$, ranges from 0.77 to 1.38 µm.

Example 19: Impact of Modified Process Parameters (Solids Content and Co-Solvent Addition) on Micromeritic Properties of Platform Antibody Formulations Formulations comprising 50.0% w/w API, 5.9% w/w histidine buffer (pH 5.0), about 14% w/w or 29% w/w trehalose and 15% w/w or 30% w/w trileucine. Powders were spray dried on a custom NSD spray dryer with an inlet temperature of 105° C., an outlet temperature of 70° C., a drying gas flow rate of 595 L/min, an atomizer gas flow rate of 30 L/min, a liquid feed rate of 4.0 mL/min, and an ALR of 7.5×10³ v/v. The solids content was reduced to 1% w/w. These modifications in the spray drying process were designed to reduce the primary particle size. In embodiments of the invention, significant reductions in the primary particle size distribution were observed.

TABLE 13

Impact of process parameters on micromeritic properties of 'platform' antibody formulations comprising 50.0% w/w API, 5.9% histidine buffer, trehalose and trileucine.

| Lot # | API (% w/w) | Solids (% w/v) | Trileucine (% w/w) | EtOH (% w/w) | PPSD (µm) ×10 | ×50 | ×90 | Tapped Density (g/cm³) |
|---|---|---|---|---|---|---|---|---|
| 761-22-01 | 50.0 | 1.0 | 15.0 | 5 | 0.39 | 1.33 | 2.59 | 0.282 |
| 761-22-02 | 50.0 | 1.0 | 15.0 | 10 | 0.51 | 1.31 | 2.59 | 0.232 |
| 761-22-03 | 50.0 | 1.0 | 15.0 | 20 | 0.53 | 1.36 | 2.94 | 0.151 |
| 761-02-04 | 50.0 | 1.0 | 15.0 | 30 | 0.55 | 1.44 | 3.15 | 0.162 |
| 761-22-05 | 50.0 | 1.0 | 30.0 | 20 | 0.64 | 1.58 | 2.94 | 0.122 |

Example 20: Impact of Modified Process Parameters (Solids Content and Co-Solvent Addition) on Aerosol Performance of Platform Antibody Formulations The impact of reductions in solids content and increases in ALR on aerosol performance of platform antibody formulations are presented in Table 14. Significant reductions in the median aerodynamic diameter of the primary particles were observed relative to the particles in Example 18. This translates into TLD between about 94% and 98% of the DD, i.e., within a desired, preferred or optimal target range of performance.

TABLE 14

Impact of process parameters on micromeritic properties and aerosol performance of platform antibody formulations. Aerosol performance was assessed with the Concept1 Inhaler (20 mg fill mass) at a flow rate of 90 L/min and a total volume of 2 L (n = 5).

| Lot # | Ethanol/ Solids | Tapped Density (g/cm³) | ×50 (µm) | Morphology | $D_a$ (calc) (µm) | DD (% ND) | TLD (% DD) |
|---|---|---|---|---|---|---|---|
| 761-22-01 | 5 | 0.282 | 1.33 | Corrugated | 0.71 | 92.4 | 97.8 |
| 761-22-02 | 10 | 0.232 | 1.31 | Corrugated | 0.63 | 93.9 | 95.1 |
| 761-22-03 | 20 | 0.151 | 1.36 | Corrugated | 0.53 | 92.1 | 95.6 |
| 761-02-04 | 30 | 0.162 | 1.44 | Corrugated | 0.58 | 93.7 | 95.0 |
| 761-22-05 | 20 | 0.122 | 1.58 | Corrugated | 0.55 | 95.0 | 93.7 |

Unless defined otherwise, the technical and scientific terms used herein have the same meaning as they usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein.

Unless indicated otherwise, each of the references cited herein is incorporated in its entirety by reference.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

The invention claimed is:

1. A molecule that specifically binds human thymic stromal lymphopoietin (TSLP) selected from any one of the following:

a) a molecule that comprises:
   a heavy chain variable region comprising:
   a heavy chain complementarity determining region 1 (HCDR1) comprising the amino acid sequence of SEQ ID NO: 4;
   a heavy chain complementarity determining region 2 (HCDR2) comprising the amino acid sequence of SEQ ID NO: 2; and
   a heavy chain complementarity determining region 3 (HCDR3) comprising the amino acid sequence of SEQ ID NO: 3; and
   a light chain variable region comprising:
   a light chain complementarity determining region 1 (LCDR1) comprising the amino acid sequence of SEQ ID NO: 11;
   a light chain complementarity determining region 2 (LCDR2) comprising the amino acid sequence of SEQ ID NO: 12; and
   a light chain complementarity determining region 3 (LCDR3) comprising the amino acid sequence of SEQ ID NO: 13;

b) a molecule that comprises:
   a heavy chain variable region comprising:
   a HCDR1 comprising the amino acid sequence of SEQ ID NO: 5;
   a HCDR2 comprising the amino acid sequence of SEQ ID NO: 6; and
   a HCDR3 comprising the amino acid sequence of SEQ ID NO: 3; and
   a light chain variable region comprising:
   a LCDR1 comprising the amino acid sequence of SEQ ID NO: 14;
   a LCDR2 comprising the amino acid sequence of SEQ ID NO: 15; and
   a LCDR3 comprising the amino acid sequence of SEQ ID NO: 16;

c) a molecule that comprises a heavy chain variable region comprising the amino acid sequence of SEQ ID NO: 7, and a light chain variable region comprising the amino acid sequence of SEQ ID NO: 17;

d) a molecule that comprises a heavy chain comprising the amino acid sequence of SEQ ID NO: 22, and a light chain comprising the amino acid sequence of SEQ ID NO: 25;

e) a molecule that comprises a heavy chain comprising the amino acid sequence of SEQ ID NO: 9, and a light chain comprising the amino acid sequence of SEQ ID NO: 19;

f) an antibody fragment that binds human TSLP and comprises
   a heavy chain variable region comprising:
   a HCDR1 comprising the amino acid sequence of SEQ ID NO: 4;
   a HCDR2 comprising the amino acid sequence of SEQ ID NO: 2; and
   a HCDR3 comprising the amino acid sequence of SEQ ID NO: 3; and
   a light chain variable region comprising:
   a LCDR1 comprising the amino acid sequence of SEQ ID NO: 11;
   a LCDR2 comprising the amino acid sequence of SEQ ID NO: 12; and
   a LCDR3 comprising the amino acid sequence of SEQ ID NO: 13;
and g) an antibody fragment that binds human TSLP and comprises:
   a heavy chain variable region comprising:
   a HCDR1 comprising the amino acid sequence of SEQ ID NO: 5;
   a HCDR2 comprising the amino acid sequence of SEQ ID NO: 6; and
   a HCDR3 comprising the amino acid sequence of SEQ ID NO: 3; and
   a light chain variable region comprising:
   a LCDR1 comprising the amino acid sequence of SEQ ID NO: 14;
   a LCDR2 comprising the amino acid sequence of SEQ ID NO: 15; and a LCDR3 comprising the amino acid sequence of SEQ ID NO: 16.

2. The molecule of claim 1, wherein the molecule is a monoclonal antibody.

3. The molecule of claim 1, wherein the molecule is an antibody fragment selected from a Fab, Fab', F(ab')2, scFv, minibody, or diabody.

4. The molecule of claim 3, wherein the molecule is a Fab.

5. The molecule of claim 4, wherein the molecule is a human or humanized Fab.

6. The molecule of claim 1, wherein the molecule is a human immunoglobulin.

7. The molecule of claim 1, wherein the molecule binds human TSLP with a dissociation constant ($K_D$) of less than 100 pM.

8. The molecule of claim 1, wherein the molecule binds human TSLP with a dissociation constant ($K_D$) of less than 10 pM.

9. A pharmaceutical composition comprising the molecule of claim 1 and at least one pharmaceutically acceptable excipient.

10. The pharmaceutical composition of claim 9, wherein the molecule is about 5% to about 95%, or about 10% to about 90%, or about 15% to about 85%, or about 20% to about 80%, or about 25% to about 75%, or about 30% to about 70%, or about 40% to about 60%, or about 40-50% (w/w) of the composition.

11. The pharmaceutical composition of claim 9, wherein the composition comprises a shell-forming agent.

12. The pharmaceutical composition of claim 11, wherein the shell-forming agent is trileucine or leucine.

13. The pharmaceutical composition of claim 12, wherein the trileucine or leucine is about 10-75% (w/w) of the composition.

14. The pharmaceutical composition of claim 13, wherein the trileucine is about 10-30% (w/w) of the composition, or wherein the leucine is about 50-75% (w/w) of the composition.

15. The pharmaceutical composition of claim 9, wherein the composition comprises at least one glass-forming excipient.

16. The pharmaceutical composition of claim 15, wherein the glass-forming excipient is selected from histidine, trehalose, mannitol, sucrose, or sodium citrate.

17. The pharmaceutical composition of claim 16, wherein the at least one glass-forming excipient is selected from trehalose or a mixture of trehalose and mannitol.

18. The pharmaceutical composition of claim 15, wherein the glass-forming excipient is about 15-35% (w/w) of the composition.

19. The pharmaceutical composition of claim 9, wherein the composition comprises a buffer.

20. The pharmaceutical composition of claim 19, wherein the buffer is selected from a histidine, glycine, acetate, or phosphate buffer.

21. The pharmaceutical composition of claim 19, wherein the buffer is about 5-13% of the composition.

22. The pharmaceutical composition of claim 9, wherein the composition is formulated as a dry powder formulation.

23. The pharmaceutical composition of claim 22, wherein the composition is formulated as a dry powder formulation suitable for inhalation.

24. The pharmaceutical composition of claim 9, wherein the composition comprises: spray-dried particles comprising a shell and a core, wherein the shell comprises trileucine or leucine and the core comprises:

i) the molecule, trehalose, mannitol, and a buffer; or ii) the molecule, trehalose, buffer, and HCl.

25. The pharmaceutical composition of claim 24, wherein the buffer is selected from a histidine, glycine, acetate, or phosphate buffer.

26. A pharmaceutical composition comprising spray-dried particles comprising:

i) a core comprising trehalose, mannitol, histidine, and a thymic stromal lymphopoietin (TSLP)-binding molecule, or a core comprising trehalose, histidine, HCl, and a TSLP-binding molecule, wherein the TSLP-binding molecule is an antibody Fab fragment comprising:

a) a heavy chain variable region comprising:
a heavy chain complementarity determining region 1 (HCDR1) comprising the amino acid sequence of SEQ ID NO: 4;
a heavy chain complementarity determining region 2 (HCDR2) HCDR2 comprising the amino acid sequence of SEQ ID NO: 2; and
a heavy chain complementarity determining region 3 (HCDR3) HCDR3 comprising the amino acid sequence of SEQ ID NO: 3; and
a light chain variable region comprising:
a light chain complementarity determining region 1 (LCDR1) comprising the amino acid sequence of SEQ ID NO: 11;
a light chain complementarity determining region 2 (LCDR2) comprising the amino acid sequence of SEQ ID NO: 12; and
a light chain complementarity determining region 3 (LCDR3) comprising the amino acid sequence of SEQ ID NO: 13;

or b) a heavy chain variable region comprising:
a HCDR1 comprising the amino acid sequence of SEQ ID NO: 5;
a HCDR2 comprising the amino acid sequence of SEQ ID NO: 6; and
a HCDR3 comprising the amino acid sequence of SEQ ID NO: 3; and
a light chain variable region comprising:
a LCDR1 comprising the amino acid sequence of SEQ ID NO: 14;
a LCDR2 comprising the amino acid sequence of SEQ ID NO: 15; and
a LCDR3 comprising the amino acid sequence of SEQ ID NO: 16; and ii) a shell comprising trileucine or leucine.

27. The pharmaceutical composition of claim 26 comprising:

a) 40% (w/w) TSLP-binding molecule, 25% (w/w) trileucine, 30% (w/w) combined weight of trehalose and mannitol, and 5% (w/w) histidine;

b) 50% (w/w) TSLP-binding molecule, 15% (w/w) trileucine, 2.6% (w/w) HCl, 5.6% (w/w) histidine, and 26.8% (w/w) combined weight of trehalose and a base; or c) 50% (w/w) TSLP-binding molecule, 15% (w/w) trileucine, 19.4% (w/w) trehalose, 13.04% (w/w) histidine, and 2.56% (w/w) HCl.

28. A kit comprising the molecule of claim 1, or the pharmaceutical composition of claim 9, and a device for delivering the molecule or pharmaceutical composition to a subject.

29. The kit of claim 28, wherein the device delivers the molecule or pharmaceutical composition in an aerosolized form.

30. The kit of claim 28, wherein the device is a dry powder inhaler.

31. The pharmaceutical composition of claim 9, wherein the excipient:molecule mass ratio is greater than 0.5.

* * * * *

SEQUENCE LISTING

<160> NUMBER OF SEQ ID NOS: 43

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Phe Ser Asp Tyr Trp Met His
1               5                   10

```
<210> SEQ ID NO 2
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

His Ile Lys Ser Lys Thr Asp Ala Gly Thr Thr Asp Tyr Ala Ala Pro
1               5                   10                  15

Val Lys Gly

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Glu Ile Tyr Tyr Tyr Ala Phe Asp Ser
1               5

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Asp Tyr Trp Met His
1               5

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Phe Thr Phe Ser Asp Tyr
1               5

<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Lys Ser Lys Thr Asp Ala Gly Thr
1               5

<210> SEQ ID NO 7
```

```
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Gly His Ile Lys Ser Lys Thr Asp Ala Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Ile Tyr Tyr Tyr Ala Phe Asp Ser Trp Gly Gln
            100                 105                 110

Gly Thr Leu Val Thr Val Ser Ser
        115                 120

<210> SEQ ID NO 8
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
gaggttcagc tggtggaatc aggcggcgga ctggttaagc ctggcggtag ccttagactt    60
agctgcgctg ctagtggctt cacctttagc gactactgga tgcactgggt tagacaggcc   120
cctggtaaag gcttggagtg ggtcggacac attaagtcta agaccgacgc cggcactacc   180
gactacgccg ctcccgttaa gggccggttc actatctcta gggacgactc taagaacacc   240
ctctaccttc aaatgaatag ccttaagacc gaggacaccg ccgtctacta ctgcgctaga   300
gaaatctact actacgcctt cgatagctgg ggtcaaggca ccctcgtgac cgtgtctagc   360

<210> SEQ ID NO 9
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45
```

```
Gly His Ile Lys Ser Lys Thr Asp Ala Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Arg Glu Ile Tyr Tyr Ala Phe Asp Ser Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145             150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450
```

-continued

```
<210> SEQ ID NO 10
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
gaggttcagc tggtggaatc aggcggcgga ctggttaagc ctggcggtag ccttagactt      60
agctgcgctg ctagtggctt cacctttagc gactactgga tgcactgggt tagacaggcc     120
cctggtaaag gcttggagtg ggtcggacac attaagtcta agaccgacgc cggcactacc     180
gactacgccg ctcccgttaa gggccggttc actatctcta gggacgactc taagaacacc     240
ctctaccttc aaatgaatag ccttaagacc gaggacaccg ccgtctacta ctgcgctaga     300
gaaatctact actacgcctt cgatagctgg ggtcaaggca ccctcgtgac cgtgtctagc     360
gctagcacta agggcccaag tgtgtttccc ctggcccca gcagcaagtc tacttccggc      420
ggaactgctg ccctgggttg cctggtgaag gactacttcc ccgagcccgt gacagtgtcc     480
tggaactctg ggctctgac ttccggcgtg cacaccttcc ccgccgtgct gcagagcagc      540
ggcctgtaca gcctgagcag cgtggtgaca gtgccctcca gctctctggg aacccagacc     600
tatatctgca acgtgaacca caagcccagc aacaccaagg tggacaagag agtggagccc     660
aagagctgcg acaagaccca cacctgcccc cctgcccag ctccagaact gctgggaggg      720
ccttccgtgt tcctgttccc ccccaagccc aaggacaccc tgatgatcag caggaccccc     780
gaggtgacct gcgtggtggt ggacgtgtcc cacgaggacc cagaggtgaa gttcaactgg     840
tacgtggacg gcgtggaggt gcacaacgcc aagaccaagc ccagagagga gcagtacaac     900
agcacctaca gggtggtgtc cgtgctgacc gtgctgcacc aggactggct gaacggcaaa     960
gaatacaagt gcaaagtctc caacaaggcc ctgccagccc caatcgaaaa gacaatcagc    1020
aaggccaagg gccagccacg ggagccccag gtgtacaccc tgcccccag ccgggaggag     1080 atgaccaaga accaggtgtc cctgacctgt ctggtgaagg gcttctaccc cagcgatatc    1140
gccgtggagt gggagagcaa cggccagccc gagaacaact acaagaccac cccccccagtg   1200 ctggacagcg acggcagctt cttcctgtac agcaagctga ccgtggacaa gtccaggtgg    1260
cagcagggca acgtgttcag ctgcagcgtg atgcacgagg ccctgcacaa ccactacacc    1320
cagaagtccc tgagcctgag ccccggcaag                                      1350

<210> SEQ ID NO 11
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser Gly Asp Asn Ile Gly Ser Lys Tyr Val His
1               5                   10

<210> SEQ ID NO 12
<211> LENGTH: 7
<212> TYPE: PRT
<213> ORGANISM: Artificial Sequence
<220> FEATURE:
<221> NAME/KEY: source
```

-continued

```
<223> OTHER INFORMATION: /note="Description of Artificial Sequence:
      Synthetic peptide"

<400> SEQUENCE: 12

Gly Asp Asn Glu Arg Pro Ser
1               5

<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gln Ala Ala Asp Trp Val Asp Phe Tyr Val
1               5                   10

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asp Asn Ile Gly Ser Lys Tyr
1               5

<210> SEQ ID NO 15
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Asp Asn
1

<210> SEQ ID NO 16
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ala Asp Trp Val Asp Phe Tyr
1               5

<210> SEQ ID NO 17
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17
```

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser Lys Tyr Val
            20                  25                  30

His Trp Tyr Gln Gln Lys Pro Gly Gln Ala Pro Val Leu Val Ile Tyr
                35                  40                  45

Gly Asp Asn Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ala Ala Asp Trp Val Asp Phe Tyr
                85                  90                  95

Val Phe Gly Gly Gly Thr Lys Leu Thr Val Leu
            100                 105

<210> SEQ ID NO 18
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
agctacgagc tgactcagcc ccttagcgtt agcgtggccc tgggtcaaac cgctagaatc      60
acctgtagcg gcgataatat cggctctaaa tacgttcact ggtatcagca gaagcccggt     120
caagcccccg tgctcgtgat ctacggcgat aacgagcggc ctagcggaat ccccgagcgg     180
tttagcggct ctaatagcgg taacaccgct accctgacta tctctagggc tcaggccggc     240
gacgaggccg actactactg tcaggccgcc gactgggtgg acttctacgt gttcggcgga     300
ggcactaagc tgaccgtgct g                                               321

<210> SEQ ID NO 19
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser Lys Tyr Val
            20                  25                  30

His Trp Tyr Gln Gln Lys Pro Gly Gln Ala Pro Val Leu Val Ile Tyr
                35                  40                  45

Gly Asp Asn Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ala Ala Asp Trp Val Asp Phe Tyr
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 20
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
agctacgagc tgactcagcc ccttagcgtt agcgtggccc tgggtcaaac cgctagaatc      60
acctgtagcg gcgataatat cggctctaaa tacgttcact ggtatcagca gaagcccggt     120
caagcccccg tgctcgtgat ctacggcgat aacgagcggc ctagcggaat ccccgagcgg     180
tttagcggct ctaatagcgg taacaccgct accctgacta tctctagggc tcaggccggc     240
gacgaggccg actactactg tcaggccgcc gactgggtgg acttctacgt gttcggcgga     300
ggcactaagc tgaccgtgct gggtcaacct aaggctgccc ccagcgtgac cctgttcccc     360
cccagcagcg aggagctgca ggccaacaag gccaccctgg tgtgcctgat cagcgacttc     420
tacccaggcg ccgtgaccgt ggcctggaag gccgacagca gccccgtgaa ggccggcgtg     480
gagaccacca cccccagcaa gcagagcaac aacaagtacg ccgccagcag ctacctgagc     540
ctgacccccg agcagtggaa gagccacagg tcctacagct gccaggtgac ccacgagggc     600
agcaccgtgg aaaagaccgt ggccccaacc gagtgcagc                            639

<210> SEQ ID NO 21
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
gaggtgcagc tggtggaatc aggcggcgga ctggtcaagc ctggcggtag cctgagactg      60
agctgcgctg ctagtggctt caccttttagc gactactgga tgcactgggt cagacaggcc    120
cctggtaaag gctggagtg gtcggacac attaagtcta agaccgacgc cggcactacc       180
gactacgccg ctcctgtgaa gggccggttc actatctcta ggacgactc taagaacacc      240 ctgtacctgc agatgaatag cctgaaaacc gaggacaccg ccgtctacta ctgcgctaga     300
gagatctact actacgcctt cgatagctgg ggtcagggca ccctggtcac cgtgtctagc     360

<210> SEQ ID NO 22
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Gly His Ile Lys Ser Lys Thr Asp Ala Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Ile Tyr Tyr Ala Phe Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys
    210                 215                 220
```

<210> SEQ ID NO 23
<211> LENGTH: 669
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
gaggtgcagc tggtggaatc aggcggcgga ctggtcaagc ctggcggtag cctgagactg      60
agctgcgctg ctagtggctt cacctttagc gactactgga tgcactgggt cagacaggcc     120
cctggtaaag gcctggagtg ggtcggacac attaagtcta agaccgacgc cggcactacc     180
gactacgccg ctcctgtgaa gggccggttc actatctcta gggacgactc taagaacacc     240
ctgtacctgc agatgaatag cctgaaaacc gaggacaccg ccgtctacta ctgcgctaga     300
gagatctact actacgcctt cgatagctgg ggtcagggca ccctggtcac cgtgtctagc     360
gctagcacta agggcccctc cgtgttccct ctggccccct ccagcaagtc tacctctggc     420
```

```
ggcaccgctg ctctgggctg cctggtgaag gactacttcc ctgagcctgt gacagtgtcc      480
tggaactctg gcgccctgac ctccggcgtg cacaccttcc ctgccgtgct gcagtcctcc      540
ggcctgtact ccctgtcctc cgtggtgaca gtgccttcct ccagcctggg cacccagacc      600
tatatctgca acgtgaacca caagccttcc aacaccaagg tggacaagcg ggtggagcct      660
aagtcatgc                                                              669

<210> SEQ ID NO 24
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
agctacgagc tgactcagcc cctgagcgtc agcgtggccc tgggtcagac cgctagaatc       60
acctgtagcg gcgataatat cggctctaaa tacgtgcact ggtatcagca gaagcccggt      120
caggcccccg tgctggtgat ctacggcgat aacgagcggc ctagcggaat ccccgagcgg      180
tttagcggct ctaatagcgg taacaccgct accctgacta tctctagggc tcaggccggc      240
gacgaggccg actactactg tcaggccgcc gactgggtgg acttctacgt gttcggcgga      300
ggcactaagc tgaccgtgct g                                                321

<210> SEQ ID NO 25
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser Lys Tyr Val
            20                  25                  30

His Trp Tyr Gln Gln Lys Pro Gly Gln Ala Pro Val Leu Val Ile Tyr
        35                  40                  45

Gly Asp Asn Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ala Ala Asp Trp Val Asp Phe Tyr
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175
```

```
Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 26
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
agctacgagc tgactcagcc cctgagcgtc agcgtggccc tgggtcagac cgctagaatc      60
acctgtagcg gcgataatat cggctctaaa tacgtgcact ggtatcagca gaagcccggt    120
caggcccccg tgctggtgat ctacggcgat aacgagcggc ctagcggaat ccccgagcgg    180
tttagcggct ctaatagcgg taacaccgct accctgacta tctctagggc tcaggccggc    240
gacgaggccg actactactg tcaggccgcc gactgggtgg acttctacgt gttcggcgga    300
ggcactaagc tgaccgtgct gggtcagcct aaggctgccc ccagcgtgac cctgttcccc    360
cccagcagcg aggagctgca ggccaacaag gccaccctgg tgtgcctgat cagcgacttc    420
tacccaggcg ccgtgaccgt ggcctggaag gccgacagca gccccgtgaa ggccggcgtg    480
gagaccacca cccccagcaa gcagagcaac aacaagtacg ccgccagcag ctacctgagc    540 ctgaccccg agcagtggaa gagccacagg tcctacagct gccaggtgac ccacgagggc    600
agcaccgtgg aaaagaccgt ggccccaacc gagtgcagc                          639

<210> SEQ ID NO 27
<211> LENGTH: 159
<212> TYPE: PRT
<213> ORGANISM: Homo sapiens

<400> SEQUENCE: 27

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
    130                 135                 140
```

Gln Gly Leu Trp Arg Arg Phe Asn Arg Pro Leu Leu Lys Gln Gln
145                 150                 155

<210> SEQ ID NO 28
<211> LENGTH: 2629
<212> TYPE: DNA
<213> ORGANISM: Homo sapiens

<400> SEQUENCE: 28

| | | | | |
|---|---|---|---|---|
| gcagccagaa agctctggag catcagggag actccaactt aaggcaacag catgggtgaa | | | | 60 |
| taagggcttc ctgtggactg gcaatgagag gcaaaacctg gtgcttgagc actggcccct | | | | 120 |
| aaggcaggcc ttacagatct cttacactcg tggtgggaag agtttagtgt gaaactgggg | | | | 180 |
| tggaattggg tgtccacgta tgttcccttt gccttacta tatgttctgt cagtttcttt | | | | 240 |
| caggaaaatc ttcatcttac aacttgtagg gctggtgtta acttacgact tcactaactg | | | | 300 |
| tgactttgag aagattaaag cagcctatct cagtactatt tctaaagacc tgattacata | | | | 360 |
| tatgagtggg accaaaagta ccgagttcaa caacaccgtc tcttgtagca atcggccaca | | | | 420 |
| ttgccttact gaaatccaga gcctaacctt caatcccacc gccggctgcg cgtcgctcgc | | | | 480 |
| caaagaaatg ttcgccatga aaactaaggc tgccttagct atctggtgcc caggctattc | | | | 540 |
| ggaaactcag ataaatgcta ctcaggcaat gaagaagagg agaaaaagga agtcacaac | | | | 600 |
| caataaatgt ctggaacaag tgtcacaatt acaaggattg tggcgtcgct tcaatcgacc | | | | 660 |
| tttactgaaa caacagtaaa ccatctttat tatggtcata tttcacagca ccaaaataaa | | | | 720 |
| tcatctttat taagtagatg aaacattaac tctaactgtg acaaagaaga ccacaaatag | | | | 780 |
| ttatctttta attacagaag agtttcttaa cttacttttg taagttttta ttgtgtaagt | | | | 840 |
| ttataatgca ggggaagtac tactcctcaa atgttgaggg aagcttccat aacattgatg | | | | 900 |
| actggcttca tggcagtaat tctcggctgt agttgcataa gcattgctca agaggaaaat | | | | 960 |
| ccaaaagtgc agcaggagaa ctctttttccc tgaaaaagga aaatattga actcaatgat | | | | 1020 |
| agcacctaaa cttacatttta aaagacagac attccttcta catgtaatga cacttcttgt | | | | 1080 |
| gttaaactaa aaatttacaa gagaagaaag tgaaagcaaa tggggtttca caaatagttg | | | | 1140 |
| taaatatagt gaagcaattt gaaataattt tcaagcaaag tattgtgaaa gtattctaag | | | | 1200 |
| ccaagtttta aatattatct aacagacaag agtggtatat acaagtagat cctgagaagt | | | | 1260 |
| accttttgtta cagctactat aaatatacat ataaattata gaatctactt taatttattt | | | | 1320 |
| tgtgaacact tttgaaaatg tacatgttcc tttgtaattg acactatata tttcttaata | | | | 1380 |
| aaataattct caaatttgtt tcttatgaat catctctcaa atctagttag acaatttgca | | | | 1440 |
| cacatacttt tctaagggac attatcttcc ttcaggtttt tacctccact catccttaga | | | | 1500 |
| gcccactgac tgctccccctt tatacctgtt ggccctgcct ataggagaga atatttggag | | | | 1560 |
| ataggcagct tcaggatgca ttgcaatcat ccttttctta aattatgtca ctagtctttt | | | | 1620 |
| attttttccc ctcttgaact ttcctcacac ctggaagaaa caaagtagga aaaagtgaac | | | | 1680 |
| aggggatgtc aaatcgattc ttgaattccc gctgcaagct agagccgcag gcaccctctc | | | | 1740 |
| actcaatttc cactcagaac cctataaaca ccagtgggaa gggcaaccca ctgcacgtgg | | | | 1800 |
| gaatgcactg attttttccta ggagtagaca tgttcctcta attactccct gagggttagt | | | | 1860 |
| tggggctaaa ccatgacaga agtggggaag ttcaatgtcc ttaaatccat cttacttgcc | | | | 1920 |
| aacaggtaag aggaagctta cattacatgt ccagtccaca tttaaagagc acttactgtg | | | | 1980 |
| gaacaagcct tcagccaaac aatggggata gaaaagtagg taagactcag cctttgtcca | | | | 2040 |

| | | | | |
|---|---|---|---|---|
| gagaagctca | gggtatagct | gaataggcag | tttcttttgt | cctgaggaaa atcaggacat | 2100 |
| gcctgctttc | taaaaatctt | cctctgaaga | cctgacccaa | gctcttaaat gctattgtaa | 2160 |
| gagaaatttc | tttgtctatt | aactccattt | tagtagggat | tcactgacta gattttactg | 2220 |
| aactatgaaa | ataaatacac | ataattttc | acaaaatttt | gggcccaatt cccctaaaag | 2280 |
| aattgaggat | tagggagaaa | ggagacaact | caaagtcatc | ccattaagtg cagtttcttt | 2340 |
| gaatcttctg | ctttatcttt | aaaaatttgt | ataatttata | tatttttattc tatgtgttcc | 2400 |
| atagatatct | taatgtaaaa | ttagtcattt | aaattacact | gtcaattaaa agtaatgggc | 2460 |
| aagagattgc | atcatactaa | tttagtaaga | acgttcccaa | atgttgtaac aatgtggatc | 2520 |
| atacatctct | ggtttttaa | atgtattgag | gctttcttgg | tggactagta tagtatacgg | 2580 |
| tcagttatgt | caatgtttca | tggtcaataa | aaaggaagtt | gcaaattgt | 2629 |

<210> SEQ ID NO 29
<211> LENGTH: 63
<212> TYPE: PRT
<213> ORGANISM: Homo sapiens

<400> SEQUENCE: 29

Met Phe Ala Met Lys Thr Lys Ala Ala Leu Ala Ile Trp Cys Pro Gly
1               5                   10                  15

Tyr Ser Glu Thr Gln Ile Asn Ala Thr Gln Ala Met Lys Lys Arg Arg
            20                  25                  30

Lys Arg Lys Val Thr Thr Asn Lys Cys Leu Glu Gln Val Ser Gln Leu
        35                  40                  45

Gln Gly Leu Trp Arg Arg Phe Asn Arg Pro Leu Leu Lys Gln Gln
    50                  55                  60

<210> SEQ ID NO 30
<211> LENGTH: 2411
<212> TYPE: DNA
<213> ORGANISM: Homo sapiens

<400> SEQUENCE: 30

| | | | | |
|---|---|---|---|---|
| accctcgcca | cgcccctgct | ccccgcggt | tggttcttcc | ttgctctact caaccctgac | 60 |
| ctcttctctc | tgactctcga | cttgtgttcc | ccgctcctcc | ctgaccttcc tccctcccc | 120 |
| tttcactcaa | ttctcaccaa | ctctttctct | ctctggtgtt | ttctcctttt ctcgtaaact | 180 |
| ttgccgccta | tgagcagcca | cattgcctta | ctgaaatcca | gagcctaacc ttcaatccca | 240 |
| ccgccggctg | cgcgtcgctc | gccaaagaaa | tgttcgccat | gaaaactaag gctgccttag | 300 |
| ctatctggtg | cccaggctat | tcggaaactc | agataaatgc | tactcaggca atgaagaaga | 360 |
| ggagaaaaag | gaaagtcaca | accaataaat | gtctggaaca | agtgtcacaa ttacaaggat | 420 |
| tgtggcgtcg | cttcaatcga | cctttactga | acaacagta | aaccatcttt attatggtca | 480 |
| tatttcacag | caccaaaata | aatcatcttt | attaagtaga | tgaaacatta actctaactg | 540 |
| tgacaaagaa | gaccacaaat | agttatcttt | taattacaga | agagtttctt aacttacttt | 600 |
| tgtaagtttt | tattgtgtaa | gtttataatg | caggggaagt | actactcctc aaatgttgag | 660 |
| ggaagcttcc | ataacattga | tgactggctt | catggcagta | attctcggct gtagttgcat | 720 |
| aagcattgct | caagaggaaa | atccaaaagt | gcagcaggag | aactcttttc cctgaaaaag | 780 |
| gaaaaatatt | gaactcaatg | atagcaccta | aacttacatt | taaaagacag acattccttc | 840 |
| tacatgtaat | gacacttctt | gtgttaaact | aaaaatttac | aagagaagaa agtgaaagca | 900 |
| aatggggttt | cacaaatagt | tgtaaatata | gtgaagcaat | ttgaaataat tttcaagcaa | 960 |

```
agtattgtga aagtattcta agccaagttt taaatattat ctaacagaca agagtggtat    1020
atacaagtag atcctgagaa gtacctttgt tacagctact ataaatatac atataaatta    1080
tagaatctac tttaatttat tttgtgaaca cttttgaaaa tgtacatgtt cctttgtaat    1140
tgacactata tatttcttaa taaaataatt ctcaaatttg tttcttatga atcatctctc    1200
aaatctagtt agacaatttg cacacatact tttctaaggg acattatctt ccttcaggtt    1260
tttacctcca ctcatcctta gagcccactg actgctcccc tttatacctg ttggccctgc    1320
ctataggaga gaatatttgg agataggcag cttcaggatg cattgcaatc atccttttct    1380
taaattatgt cactagtctt ttattttttc ccctcttgaa ctttcctcac acctggaaga    1440
aacaaagtag gaaaagtga acaggggatg tcaaatcgat tcttgaattc ccgctgcaag    1500
ctagagccgc aggcaccctc tcactcaatt tccactcaga accctataaa caccagtggg    1560
aagggcaacc cactgcacgt gggaatgcac tgattttttcc taggagtaga catgttcctc    1620
taattactcc ctgagggtta gttggggcta aaccatgaca gaagtgggga agttcaatgt    1680
ccttaaatcc atcttacttg ccaacaggta agaggaagct tacattacat gtccagtcca    1740
catttaaaga gcacttactg tggaacaagc cttcagccaa acaatgggga tagaaaagta    1800
ggtaagactc agcctttgtc cagagaagct cagggtatag ctgaataggc agtttctttt    1860
gtcctgagga aaatcaggac atgcctgctt tctaaaaatc ttcctctgaa gacctgaccc    1920
aagctcttaa atgctattgt aagagaaatt tctttgtcta ttaactccat tttagtaggg    1980
attcactgac tagattttac tgaactatga aaataaatac acataatttt tcacaaaatt    2040
ttgggcccaa ttcccctaaa agaattgagg attagggaga aaggagacaa ctcaaagtca    2100
tcccattaag tgcagtttct ttgaatcttc tgctttatct ttaaaaattt gtataattta    2160 tatatttttat tctatgtgtt ccatagatat cttaatgtaa aattagtcat ttaaattaca    2220
ctgtcaatta aaagtaatgg gcaagagatt gcatcatact aatttagtaa gaacgttccc    2280
aaatgttgta acaatgtgga tcatacatct ctggtttttt aaatgtattg aggctttctt    2340
ggtggactag tatagtatac ggtcagttat gtcaatgttt catggtcaat aaaaaggaag    2400
ttgcaaattg t                                                        2411
```

<210> SEQ ID NO 31
<211> LENGTH: 131
<212> TYPE: PRT
<213> ORGANISM: Macaca fascicularis

<400> SEQUENCE: 31

Tyr Asp Phe Thr Asn Cys Asp Phe Glu Lys Ile Glu Ala Asp Tyr Leu
1               5                   10                  15

Arg Thr Ile Ser Lys Asp Leu Ile Thr Tyr Met Ser Gly Thr Lys Ser
            20                  25                  30

Thr Asp Phe Asn Asn Thr Val Ser Cys Ser Asn Arg Pro His Cys Leu
        35                  40                  45

Thr Glu Ile Gln Ser Leu Thr Phe Asn Pro Thr Pro Arg Cys Ala Ser
    50                  55                  60

Leu Ala Lys Glu Met Phe Ala Arg Lys Thr Lys Ala Thr Leu Ala Leu
65                  70                  75                  80

Trp Cys Pro Gly Tyr Ser Glu Thr Gln Ile Asn Ala Thr Gln Ala Met
                85                  90                  95

Lys Lys Arg Arg Lys Arg Lys Val Thr Thr Asn Lys Cys Leu Glu Gln
            100                 105                 110

Val Ser Gln Leu Leu Gly Leu Trp Arg Arg Phe Ile Arg Thr Leu Leu
            115                 120                 125

Lys Lys Gln
    130

<210> SEQ ID NO 32
<211> LENGTH: 393
<212> TYPE: DNA
<213> ORGANISM: Macaca fascicularis

<400> SEQUENCE: 32
tacgacttca ccaactgcga cttcgagaag atcgaggccg actacctgag aaccatcagc     60
aaggacctga tcacctacat gagcggcacc aagagcaccg acttcaacaa caccgtgtcc    120
tgcagcaaca gaccccactg cctgaccgag atccagagcc tgaccttcaa ccccaccccc    180
agatgtgcca gcctggccaa agagatgttc gccagaaaga ccaaggccac cctggccctg    240
tggtgtcccg gctacagcga gacacagatc aacgccacac aggccatgaa gaagcggcgg    300
aagcggaaag tgaccaccaa caagtgcctg aacaggtgt cacagctgct ggggctgtgg    360
cggcggttca tccggaccct gctgaagaag cag                                 393

<210> SEQ ID NO 33
<211> LENGTH: 140
<212> TYPE: PRT
<213> ORGANISM: Mus musculus

<400> SEQUENCE: 33

Met Val Leu Leu Arg Ser Leu Phe Ile Leu Gln Val Leu Val Arg Met
1               5                   10                  15

Gly Leu Thr Tyr Asn Phe Ser Asn Cys Asn Phe Thr Ser Ile Thr Lys
            20                  25                  30

Ile Tyr Cys Asn Ile Ile Phe His Asp Leu Thr Gly Asp Leu Lys Gly
        35                  40                  45

Ala Lys Phe Glu Gln Ile Glu Asp Cys Glu Ser Lys Pro Ala Cys Leu
    50                  55                  60

Leu Lys Ile Glu Tyr Tyr Thr Leu Asn Pro Ile Pro Gly Cys Pro Ser
65                  70                  75                  80

Leu Pro Asp Lys Thr Phe Ala Arg Arg Thr Arg Glu Ala Leu Asn Asp
                85                  90                  95

His Cys Pro Gly Tyr Pro Glu Thr Glu Arg Asn Asp Gly Thr Gln Glu
            100                 105                 110

Met Ala Gln Glu Val Gln Asn Ile Cys Leu Asn Gln Thr Ser Gln Ile
        115                 120                 125

Leu Arg Leu Trp Tyr Ser Phe Met Gln Ser Pro Glu
    130                 135                 140

<210> SEQ ID NO 34
<211> LENGTH: 1143
<212> TYPE: DNA
<213> ORGANISM: Mus musculus

<400> SEQUENCE: 34
cacgttcagg cgacagcatg gttcttctca ggagcctctt catcctgcaa gtactagtac     60
ggatggggct aacttacaac ttttctaact gcaacttcac gtcaattacg aaaatatatt    120
gtaacataat ttttcatgac ctgactggag atttgaaagg ggctaagttc gagcaaatcg    180
aggactgtga gagcaagcca gcttgtctcc tgaaaatcga gtactatact ctcaatccta    240

```
tccctggctg ccccttcactc cccgacaaaa catttgcccg gagaacaaga gaagccctca      300
atgaccactg cccaggctac cctgaaactg agagaaatga cggtactcag gaaatggcac      360
aagaagtcca aaacatctgc ctgaatcaaa cctcacaaat tctaagattg tggtattcct      420
tcatgcaatc tccagaataa aattagcttt cagcttctgc tatgaaaatc tctatcttgg      480
ttttagtgga cagaatacta agggtgtgac acttagagga ccactggtgt ttattcttta      540
attacagaag ggattcttaa cttattttt ggcatatcgc ttttttcagt ataggtgctt      600
taaatgggaa atgagcaata gaccgttaat ggaaatatct gtactgttaa tgaccagctt      660
ctgagaagtc tttctcacct cccctgcaca caccttactc tagggcaaac ctaactgtag      720
taggaagaga attgaaagta gaaaaaaaa attaaaacca atgacagcat ctaaaccctg      780
tttaaaaggc aaggattttt ctacctgtaa tgattcttct aacattccta tgctaagatt      840
ttaccaaaga gaaaatgac agttcgggca gtcactgcca tgatgaggtg gtctgaaaga      900
agattgtgga atctgggaga aactgctgag atcatattgc aaatccagct gtcaaagggt      960
tcagacccag gacagtacaa ttcgtgagca gatctcaaga gccttgcaca tctacgagat      1020
atatatttaa agttgtagat aatgaatttc taatttattt tgtgagcact tttggaaata      1080
tacatgctac tttgtaatga atacatttct gaataaagta attctcaagt ttgaaaaaaa      1140
aaa                                                                   1143

<210> SEQ ID NO 35
<211> LENGTH: 1146
<212> TYPE: DNA
<213> ORGANISM: Mus musculus

<400> SEQUENCE: 35
actcttgcca ggcacctccc tcctgtgggt tgattccgtt ttcctcttct caactgactc       60
tggattctga taccagacac cttcctggtg tctttccctc ctatccccat ccccttccct      120
gtccctttca ttcaatttt aatatctggc gggttttttt tttttttct ctctctctga       180 actgtgccgc ttgtgagcag ccagcttgtc tcctgaaaat cgagtactat actctcaatc      240
ctatccctgg ctgcccttca ctccccgaca aaacatttgc ccggagaaca agagaagccc      300
tcaatgacca ctgcccaggc taccctgaaa ctgagagaaa tgacggtact caggaaatgg      360
cacaagaagt ccaaaacatc tgcctgaatc aaacctcaca aattctaaga ttgtggtatt      420
ccttcatgca atctccagaa taaaattagc tttcagcttc tgctatgaaa atctctatct      480
tggttttagt ggacagaata ctaagggtgt gacacttaga ggaccactgg tgtttattct      540
ttaattacag aagggattct taacttattt tttggcatat cgcttttttc agtataggtg      600
ctttaaatgg gaaatgagca atagaccgtt aatggaaata tctgtactgt taatgaccag      660
cttctgagaa gtctttctca cctcccctgc acacaccctta ctctagggca aacctaactg      720
tagtaggaag agaattgaaa gtagaaaaaa aaaattaaaa ccaatgacag catctaaacc      780
ctgtttaaaa ggcaaggatt tttctacctg taatgattct tctaacattc ctatgctaag      840 atttaccaa agaagaaaat gacagttcgg gcagtcactg ccatgatgag gtggtctgaa      900
agaagattgt ggaatctggg agaaactgct gagatcatat tgcaaatcca gctgtcaaag      960
ggttcagacc caggacagta caattcgtga gcagatctca agagccttgc acatctacga     1020
gatatatatt taagttgta gataatgaat ttctaatta ttttgtgagc acttttggaa      1080
atatacatgc tactttgtaa tgaatacatt tctgaataaa gtaattctca agtttgaaaa     1140
``` aaaaaa                                                                      1146

<210> SEQ ID NO 36
<211> LENGTH: 136
<212> TYPE: PRT
<213> ORGANISM: Rattus norvegicus

<400> SEQUENCE: 36

Met Val Leu Phe Arg Tyr Leu Phe Ile Leu Gln Val Val Arg Leu Ala
1               5                   10                  15

Leu Thr Tyr Asn Phe Ser Asn Cys Asn Phe Glu Met Ile Leu Arg Ile
            20                  25                  30

Tyr His Ala Thr Ile Phe Arg Asp Leu Leu Lys Asp Leu Asn Gly Ile
        35                  40                  45

Leu Phe Asp Gln Ile Glu Asp Cys Asp Ser Arg Thr Ala Cys Leu Leu
    50                  55                  60

Lys Ile Asp His His Thr Phe Asn Pro Val Pro Gly Cys Pro Ser Leu
65                  70                  75                  80

Pro Glu Lys Ala Phe Ala Leu Lys Thr Lys Ala Ala Leu Ile Asn Tyr
                85                  90                  95

Cys Pro Gly Tyr Ser Glu Thr Glu Arg Asn Gly Thr Leu Glu Met Thr
            100                 105                 110

Arg Glu Ile Arg Asn Ile Cys Leu Asn Gln Thr Ser Gln Ile Leu Gly
        115                 120                 125

Leu Trp Leu Ser Cys Ile Gln Ser
    130                 135

<210> SEQ ID NO 37
<211> LENGTH: 1125
<212> TYPE: DNA
<213> ORGANISM: Rattus norvegicus

<400> SEQUENCE: 37
tcaggcaaca gcatggttct tttcaggtac ctctttatcc tgcaagtggt acggctggca      60
ctaacttaca acttttctaa ctgtaacttc gagatgattt tgagaatata tcatgcaaca     120
attttccgtg acctgcttaa agatttgaat gggatcttgt tcgaccaaat cgaggactgt     180
gacagcagga cagcttgtct cctgaaaatc gaccaccata ccttcaatcc tgtccctggc     240
tgcccgtcac tccccgagaa agcgttcgct ttgaaaacga aagcggccct cattaactac     300
tgcccaggct actctgaaac tgagagaaat ggtactctgg aaatgacacg agaaatcaga     360
aacatctgcc tgaatcaaac ctcacaaatt ctaggattgt ggctttcctg cattcaatct     420
tgaagaaaaa attagctttt ggattatatt atgaaaatat atatcttgtt tttagtagat     480
ataatactaa gggtgtgaca cttaaaagaa cactaatgtt tattctttaa ttatagaagg     540
gattcttaac ttatttttgg catatcgttg tttagtgtag gcgctttaaa tggaaaatga     600
gcattacccc tttaatggaa ataaccgtgc tgttaatgat tggcttcggc ttctgagcag     660
tctttctcac ctcacctgag acactttact ctagggcaaa cctaactgta gtaggaagaa     720
aatcaaaagt agaaaaacag ttgaaaccaa tgacaggatc tatactccat ttaaaaggca     780 agaattttg tacctgtaat gattcttcta acattcctac gctaagattt tactaaagaa     840 gaaataaca gcagaggaaa gtgttcaggc agtcactgcc atgatgaagc tgtcagaatc     900
tgagagctac tgctgcaact gatcgtgtag taaatccagc tgtaaagggg atcttaaccc     960
accacagtgg gatgcacagg cagatcccca agggcattgt gcagctgtga gatatatatt    1020
taaagttgta tataatgatt ttctaattta ttccgtgagc accttttgaaa atatacatgt    1080 cgctgtgtaa caaatacact tctgaataaa gtaattctca agttc    1125

<210> SEQ ID NO 38
<211> LENGTH: 149
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Gly Ser Ser His His His His His His Leu Glu Val Leu Phe Gln
1               5                   10                  15

Gly Pro Tyr Asp Phe Thr Asn Cys Asp Phe Glu Lys Ile Lys Ala Ala
            20                  25                  30

Tyr Leu Ser Thr Ile Ser Lys Asp Leu Ile Thr Tyr Met Ser Gly Thr
        35                  40                  45

Lys Ser Thr Glu Phe Asn Asn Thr Val Ser Cys Ser Asn Arg Pro His
    50                  55                  60

Cys Leu Thr Glu Ile Gln Ser Leu Thr Phe Asn Pro Thr Ala Gly Cys
65                  70                  75                  80

Ala Ser Leu Ala Lys Glu Met Phe Ala Met Lys Thr Lys Ala Ala Leu
                85                  90                  95

Ala Ile Trp Cys Pro Gly Tyr Ser Glu Thr Gln Ile Asn Ala Thr Gln
            100                 105                 110

Ala Met Lys Lys Arg Arg Lys Arg Lys Val Thr Thr Asn Lys Cys Leu
        115                 120                 125

Glu Gln Val Ser Gln Leu Gln Gly Leu Trp Arg Arg Phe Asn Arg Pro
    130                 135                 140

Leu Leu Lys Gln Gln
145

<210> SEQ ID NO 39
<211> LENGTH: 4
<212> TYPE: PRT
<213> ORGANISM: Unknown
<220> FEATURE:
<221> NAME/KEY: source
<223> OTHER INFORMATION: /note="Description of Unknown: Potential
      furin cleavage site"

<400> SEQUENCE: 39

Arg Arg Lys Arg
1

<210> SEQ ID NO 40
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 40

His His His His His His
1               5

<210> SEQ ID NO 41
<211> LENGTH: 131

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Tyr Asp Phe Thr Asn Cys Asp Phe Glu Lys Ile Lys Ala Ala Tyr Leu
1               5                   10                  15

Ser Thr Ile Ser Lys Asp Leu Ile Thr Tyr Met Ser Gly Thr Lys Ser
            20                  25                  30

Thr Glu Phe Asn Asn Thr Val Ser Cys Ser Asn Arg Pro His Cys Leu
        35                  40                  45

Thr Glu Ile Gln Ser Leu Thr Phe Asn Pro Thr Ala Gly Cys Ala Ser
    50                  55                  60

Leu Ala Lys Glu Met Phe Ala Met Lys Thr Lys Ala Ala Leu Ala Ile
65                  70                  75                  80

Trp Cys Pro Gly Tyr Ser Glu Thr Gln Ile Asn Ala Thr Gln Ala Met
                85                  90                  95

Lys Lys Arg Arg Lys Arg Lys Val Thr Thr Asn Lys Cys Leu Glu Gln
            100                 105                 110

Val Ser Gln Leu Gln Gly Leu Trp Arg Arg Phe Asn Arg Pro Leu Leu
        115                 120                 125

Lys Gln Gln
    130

<210> SEQ ID NO 42
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Gly His Ile Lys Ser Lys Thr Asp Ala Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Ile Tyr Tyr Ala Phe Asp Ser Trp Gly Gln
            100                 105                 110

Gly Thr Leu Val Thr Val Ser
        115

<210> SEQ ID NO 43
<211> LENGTH: 109
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
    Synthetic polypeptide"

<400> SEQUENCE: 43

```
Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser Lys Tyr Val
            20                  25                  30

His Trp Tyr Gln Gln Lys Pro Gly Gln Ala Pro Val Leu Val Ile Tyr
        35                  40                  45

Gly Asp Asn Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ala Ala Asp Trp Val Asp Phe Tyr
                85                  90                  95

Val Phe Gly Gly Gly Thr Lys Leu Thr Val Leu Gly Gln
                100                 105
```